US008193330B2

(12) United States Patent
German

(10) Patent No.: US 8,193,330 B2

(45) Date of Patent: *Jun. 5, 2012

(54) POLYNUCLEOTIDES COMPRISING NEUROGENIN3 PROMOTER AND BHLH ENCODING DOMAINS

(75) Inventor: Michael S. German, Daly City, CA (US)

(73) Assignee: The Regents of the University of California, Oakland, CA (US)

( * ) Notice: Subject to any disclaimer, the term of this patent is extended or adjusted under 35 U.S.C. 154(b) by 1754 days.

This patent is subject to a terminal disclaimer.

(21) Appl. No.: 10/642,093

(22) Filed: Aug. 14, 2003

(65) Prior Publication Data

US 2004/0106555 A1 Jun. 3, 2004

Related U.S. Application Data

(63) Continuation-in-part of application No. PCT/US02/11166, filed on Mar. 20, 2002, and a continuation-in-part of application No. 09/817,360, filed on Mar. 20, 2001, now Pat. No. 6,967,019, which is a continuation-in-part of application No. 09/535,145, filed on Mar. 24, 2000, now Pat. No. 6,703,220.

(60) Provisional application No. 60/128,180, filed on Apr. 6, 1999.

(51) Int. Cl.
*C07H 21/00* (2006.01)
*C12N 15/85* (2006.01)

(52) U.S. Cl. .................................... 536/24.1; 435/320.1

(58) Field of Classification Search .................. 536/23.1
See application file for complete search history.

(56) References Cited

U.S. PATENT DOCUMENTS

| | | | |
|---|---|---|---|
| 5,695,995 | A | 12/1997 | Weintraub et al. |
| 5,795,723 | A | 8/1998 | Tapscott et al. |
| 5,830,730 | A | 11/1998 | German et al. |
| 6,127,598 | A | 10/2000 | German et al. |
| 2002/0015696 | A1 | 2/2002 | German |
| 2003/0082810 | A1 | 5/2003 | Serup |

FOREIGN PATENT DOCUMENTS

| | | |
|---|---|---|
| JP | 5115296 A2 | 5/1993 |
| WO | WO 96/34093 | 10/1996 |
| WO | WO 98/13491 | 4/1998 |
| WO | WO 00/09676 | 2/2000 |
| WO | WO 00/59936 | 10/2000 |
| WO | WO 01/01130 | 1/2001 |

OTHER PUBLICATIONS

LeClerc et al., Nature 297:596-597 (1982).*

Sommer et al, Molecular and Cellular Neuroscience 8: 221-241 (1996).*

Gradwohl, et al. "Neurogenin3 is required for the development of the four endocrine cell lineages of the pancreas", *Proc. Natl. Acad. Sci. USA.*, (2000) vol. 97(4): 1607-1611.

Huang, et al. "Transcription factors involved in pancreatic islet development", *J. Biomedical Sci.*, (2000) vol. 7(1): 27-34.

Jensen, et al. "Independent development of pancreatic alpha and beta cells from neurogenin3—expressing precursors: A role for the Notch pathway in repression of premature differentiation", *Diabetes*, (2000) vol. 49(2): 163-176.

Ravassard, et al. "Relax, a novel rat bHLH transcriptional regulator transiently expressed in the ventricular proliferating zone of the developing central nervous system", *Canadian J. Chem.*, (1997) vol. 48(2): 146-158.

Ravassard, et al. "*Homo sapiens* gene for neurogenin3", *Database EMBL Online*, (1999) Database accession No. AJ33776.

Rudinger. "Characteristics of the amino acids as components of a peptide hormone sequence" in *Peptide Hormones* (ed. J.A. Parson), (1976) pp. 1-7, University Park Press, Baltimore.

Sommer, et al., "*Neurogenins*, a novel family of atonal-related bHLH transcription factors, are putative mammalian neuronal determination genes that reveal progenitor cell heterogeneity in the developing CNS and PNS," *Molecular and Cellular Neuroscience*, (1996) vol. 8: 221-241.

GenBank Accession No. U76208, deposited Feb. 5, 1997.

GenBank Accession No. Y09167, deposited Nov. 14, 1997.

GenBank Accession No. Y10619, deposited May 6, 1997.

GenBank Accession No. AJ133776.1, deposited Jun. 19, 1999.

GenBank Accession No. NM_020999, deposited Nov. 29, 2000.

Furuta et al. (Aug. 1998), "Beta-Cell Transcription Factors and Diabetes." *Diabetes*, vol. 47:1356-1358.

Goldfine et al. (Dec. 1997), "The Endocrine Secretion of Human Insulin and Growth Hormone by Exocrine Glands of the Gastrointestinal Tract." *Nature Biotechnology*, vol. 15:1378-1382.

Horikawa et al. (Nov. 2000), "Beta-Cell Transcription Factors and Diabetes." *Diabetes*, vol. 49:1955-1957.

Iannotti et al. (1997), "Identification of a Human LMX1 (LMX1.1)-Related Gene, LMX1.2:Tissue Specific Expression and Linkage Mapping of Chromosome 9." *Genomics*, vol. 43:520-524.

Inoue et al. (1997), "Isolation, Characterization, and Chromosomal Mapping of the Human Nkx6.1 Gene (NKX6A), a New Pancreatic Islet Homeobox Gene." *Genomics*, vol. 40:367-370.

Mirmira et al. (May 12, 2000), "Beta-Cell Differentiation Factor Nkx6.1 Contains Distinct DNA Binding Interference and Transcriptional Repression Domains." *The Journal of Biochemistry*, vol. 275(19):14743-14751.

Odagiri et al. (Jan. 26, 1996), "Function of the Human Insulin Promoter in Primary Cultured Islet Cells." *The Journal of Biochemistry*, vol. 271(4):1909-1915.

Ogata et al. (Mar. 2001), "Mutations in the Coding Region of Neurogenin 3 Gene (NEUROG3) are no Common Cause of Maturity-Onset Diabetes in Japanese Subject." *Diabetes*, vol. 50(3):694-696.

Rudnick et al. (Dec. 1994), "Pancreatic Beta Cells Express a Diverse Set of Homeobox Genes." *Proc. Natl. Acad. Sci. USA*, vol. 91:12203-12207.

(Continued)

*Primary Examiner* — Robert C Hayes

(74) *Attorney, Agent, or Firm* — James S. Keddie; Bozicevic, Field & Francis, LLP

(57) ABSTRACT

The present invention features polypeptides having activity of human neurogenin3 (hNgn3), and nucleic acid encoding such polypeptide. The invention also features use of islet transcription factors such as hNgn3 to facilitate production of pancreatic islet cells from progenitor cells, and to facilitate insulin delivery by production of islet cells so produced.

4 Claims, 26 Drawing Sheets

OTHER PUBLICATIONS

Sander et al. (Sep. 1998), "A Novel Glucose-Responsive Element in the Human Insulin Gene Function as Uniquely in Primary Cultured Islets." *Proc. Natl. Acad. Sci. USA*, vol. 95:11572-11577.
Sander et al. (1997), "The beta Cell Transcription Factors and Development of the Pancreas." *J. Mol. Med.*, vol. 75:327-340.
Sander et al. (1997), "Genetic Analysis Reveals that PAX6 is Required for Normal Transcription of Pancreatic Hormone Genes and Islet Development." *Genes and Development*, vol. 11:1662-1673.
Sander et al. (2000), "Homeobox Gene Nkx6.1 Lies Downstream of Nkx2.2 in the Major Pathway of Beta-Cell Formation in the Pancreas." *Development*, vol. 127:5533-5540.
Schwizgebel et al. (2000), "Expression of Neurogenenin3 Reveals an Islet Cell Precursor Population in the Pancreas." *Development*, vol. 127:3533-3542.
Sussel et al. (1998), "Mice Lacking the Homeodomain Transcription Factor Kkx2.2 Have Diabetes due to Arrested Differentiation of Pancreatic Beta Cells." *Development*, vol. 125:2213-2221.
Wang et al. (Apr. 1997), "Regulation of Insulin preRNA Splicing by Glucose." *Proc. Natl. Acad. Sci. USA.*, vol. 94:4360-4365.
Watada et al. (2000), "Transcriptional and Translational Regulation of Beta-Cell Differentiation Factor Nkx6.1." *The Journal of Biological Chemistry*, vol. 275(44):34224-34230.
Huang, H-P. et al., Regulation of the Pancreatic Islet-Specific Gene BETA2 (neuroD) by Neurogenein 3. Molecular and Cellular Biology. May 200, vol. 20, 3292-3307 (May 2000).
Malecki, M.T. et al., Mutations in Neurod1 are Associated with the Development of Type 2 Diabetes Mellitus, Nature Genetics. Nov. 1999, vol. 23, pp. 323-328.
Schmied, B.M. et al, Differentiation of Islet Cells in Long-Term Culture. Pancreas. vol. 20, No. 4, pp. 337-347 (2000).
Xu, W, et al., Isolation and Characterization of the Mouse Beta2/neuroD Gene Promoter. Biochemical and Biophysical Research Communications. 1998, vol. 247, pp. 814-818.
Black, B., et al., "Multiple Roles for the MyoD basic region in transmission of transcriptional activation signals and interaction with MEF2," (1998) *Molecular and Cellular Biology*, 18(1):69-77.
Brownlie, P., et al., "The crystal structure of an Intact human Max-DNA complex: new insights into mechanisms of transcriptional control," (1997) *Structure*, 5(4):509-520.
Ellenberger, T., et al., "Crystal structure of transcription factor E47: E-box recognition by a basic region helix-loop-helix dimer," (1994) *Genes & Development*, 8:970-980.
Ferré-D'Amaré, A., et al., "Recognition by Max of its cognate DNA through a dimeric b/HLH/Z domain," (1993) *Nature*, 363:38-45.
Ferré-D'Amaré, A., et al., "Structure and function of the b/HLH/Z domain of USF," (1994) *The EMBO Journal*, 13(1):180-189.
Ma, P., et al., "Crystal structure of MyoD bHLH domain-DNA complex: perspectives on DNA recognition and implications for transcriptional activation," (1994) Cell, 77:451-459.
Morgenstern, B., et al., "Evolution of bHLH transcription factors: modular evolution by domain shuffling?" (1999) *Molecular Biology and Evolution*, 16(12):1654-1663.
Párraga, A., et al., "Co-crystal structure of sterol regulatory element binding protein 1a at 2.3 Å resolution," (1998) *Structure*, 6:661-672.
Shimizu, T., et al., "Crystal structure of PHO4 bHLH domain-DNA complex: flanking base recognition," (1997) *The EMBO Journal*, 16(15):4689-4697.
Mak et al, *Examination of mammalian basic helix-loop-helix transcription factors using a yeast one-hybrid system*. DNA Cell Biol. (1996) 15:1-8.
Lemercier et al, *Mist1: A novel basic helix-loop-helix transcription factor exhibits a developmentally regulated expression pattern*. Dev. Biol. (1997) 182:101-13.
Garriga-Canut et al, *The basic helix-loop-helix protein, sharp-1, represses transcription by a histone deacetylase-dependent and histone deacetylase-independent mechanism*. J. Biol. Chem. (2001) 276:14821-8.
Taylor et al, *E1A-mediated inhibition of myogenesis correlates with a direct physical interaction of E1A12S and basic helix-loop-helix proteins* Mol. Cell Biol. (1993) 13:4714-27.
Jimenez et al, *A chimeric enhancer-of-split transcriptional activator drives neural development and achaete-scute expression* Mol. Cell Biol. (1997) 17:4355-62.
Black et al, *Multiple roles for the MyoD basic region in transmission of transcriptional activation signals and interaction with MEF2*. Mol. Cell Biol. (1998) 18:69-77.
Chakraborty et al, *Inefficient homooligomerization contributes to the dependence of myogenin on E2A products for efficient DNA binding* M. Cell Biol. (1991) 11: 3633-3641.
Yin et al, *Lack of transcriptional repression by max homodimers*. Oncogene. (1998) 16:2629-2370.
Jacquemin, P., et al. Transcription factor hepatocyte nuclear factor 6 regulates pancreatic endocrine cell differentiation and controls expression of the proendocrine gene ngn3. Molecular and Cellular Biology. 2000, vol. 20, No. 12, pp. 4445-4454.
Gasa, R., et al. Proendocrine genes coordinate the pancreatic islet differentiation program in vitro. PNAS. 2004, vol. 101, No. 36, pp. 13245-13250.
Naya, F., et al. Tissue-specific regulation of the insulin gene by a novel basic helix-loop-helix transcription factor. Genes & Development. 1995, vol. 9, pp. 1009-1019.

* cited by examiner

FIG. 6
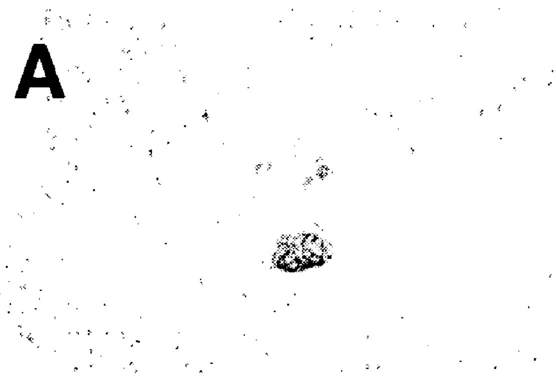
WT
FIG. 7
B
pdx1-
ngn3
FIG. 8
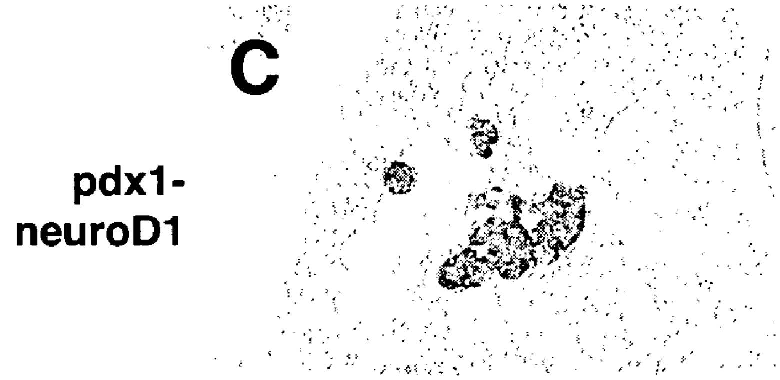

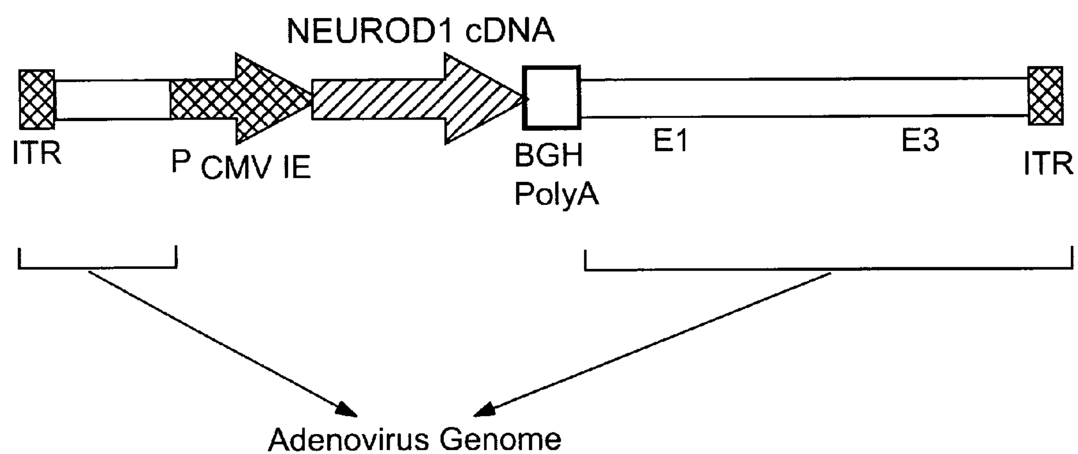
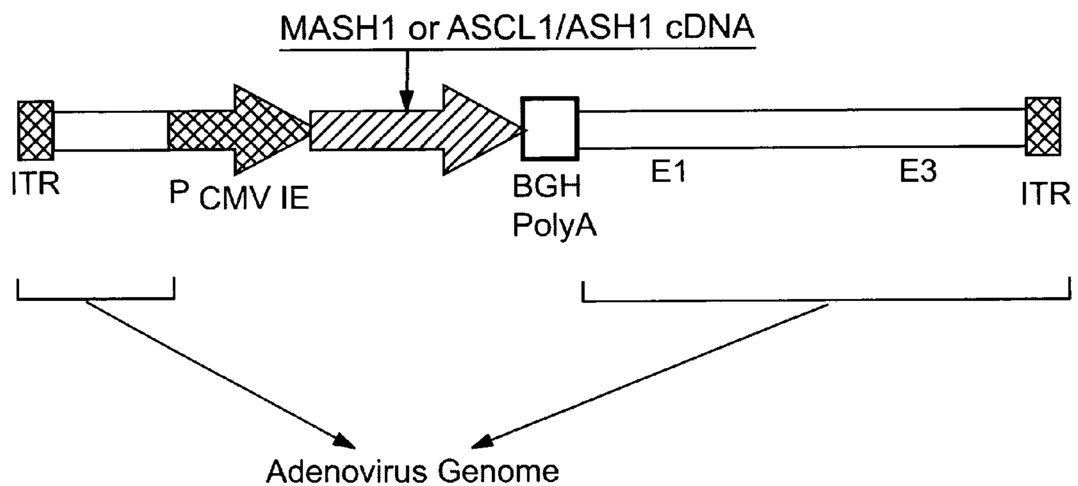
FIG. 9

-0.5 kb
-1.7 kb
-2.6 kb
-5.7 kb
RSV
CHO
3T3
mPAC
βTC
αTC
ND
50
100
150
200
250
Relative Luciferase Activity 3T3 Cells
ngn3-Luc
Luc
RSV-Luc
Relative Lucif rase Activity
2.5
2.0
1.5
1.0
0.5
0.0
<0.01
<0.01
0 ng
30 ng
60 ng
90 ng
Co-transfected HES1 expression plasmid 3T3 Cells
-5.7 kb Ngn3
Luc
-2.6 kb
-1.7 kb
-0.5 kb
RSV
-5.7 kb Ngn3
-2.6 kb
-1.7 kb
-0.5 kb
RSV
- HES1
+ HES1
0
1
2
3
4
Relative Luciferase Activity -250bp Ngn3
LUC
-4kb to -250bp Ngn3
TK
TK
RSV
3T3
αTC1.6
0
5
10
15
20
25
Fold repression by HES1.

Proximal Promoter

-124 bp

CGGGCTCGCGTGGCGCGGCCCCAGGGCCCCGGCGCTGATTGGCCGGTGGC
N1

GCGGGCAGCAGCCGGGCAGGCACGCTCCTGGCCCGGGCGAAGCA*GATAA*
N2 TATAA Box

AGCGTGCCAAGGGGCACACGACTTGCT
N3 N4 +1 bp

FIG. 28

Formatted Alignments

| | 10 | 20 | 30 |
|---|---|---|---|
| hNGN3p | M T P Q P S G A P T | V Q V T R E T E R S | F P R A S E D E V T |
| rNGN3p | M A P H P L D A P T | I Q V S Q E T Q Q P | F P G A S D H E V L |
| mNGN3p | M A P H P L D A L T | I Q V S P E T Q Q P | F P G A S D H E V L |

| | 40 | 50 | 60 |
|---|---|---|---|
| hNGN3p | C P T S A P P S P T | R T R G N C A E A E | E G G C R G A P R K |
| rNGN3p | S S N S T P P S P T | L V P R D C S E A E | A G D C R G T S R K |
| mNGN3p | S S N S T P P S P T | L I P R D C S E A E | V G D C R G T S R K |

| | 70 | 80 | 90 |
|---|---|---|---|
| hNGN3p | L R A R R G G R S R | P K S E L A L S K Q | R R S R R K K A N D |
| rNGN3p | L R A R R G G R N R | P K S E L A L S K Q | R R S R R K K A N D |
| mNGN3p | L R A R R G G R N R | P K S E L A L S K Q | R R S R R K K A N D |

| | 100 | 110 | 120 |
|---|---|---|---|
| hNGN3p | R E R N R M H N L N | S A L D A L R G V L | P T F P D D A K L T |
| rNGN3p | R E R N R M H N L N | S A L D A L R G V L | P T F P D D A K L T |
| mNGN3p | R E R N R M H N L N | S A L D A L R G V L | P T F P D D A K L T |

| | 130 | 140 | 150 |
|---|---|---|---|
| hNGN3p | K I E T L R F A H N | Y I W A L T Q T L R | I A D H S L Y A L E |
| rNGN3p | K I E T L R F A H N | Y I W A L T Q T L R | I A D H S F Y G P E |
| mNGN3p | K I E T L R F A H N | Y I W A L T Q T L R | I A D H S F Y G P E |

| | 160 | 170 | 180 |
|---|---|---|---|
| hNGN3p | P P A P H C G E L G | S P G G - S P G D W | G S L Y S P V S Q A |
| rNGN3p | P P V P - C G E L G | S P G G G S S G D W | G S I Y S P V S Q A |
| mNGN3p | P P V P - C G E L G | S P G G G S N G D W | G S I Y S P V S Q A |

| | 190 | 200 | 210 |
|---|---|---|---|
| hNGN3p | G S L S P A A S L E | E R P G L L G A T S | S A C L S P G S L A |
| rNGN3p | G S L S P T A S L E | E F P G L Q V P S S | P S C L L P G T L V |
| mNGN3p | G N L S P T A S L E | E F P G L Q V P S S | P S Y L L P G A L V |

| | 220 | 230 | 240 |
|---|---|---|---|
| hNGN3p | F S D F L | | |
| rNGN3p | F S D F L | | |
| mNGN3p | F S D F L | | |

FIG. 29

```
hNGN3bHLH vs. mNGN1bHLH

   Aligned Length = 57   Gaps = 0
   Identities = 49 (85%)

hNGN3bHLH   82 RSRRKKANDRERNRMHNLNSALDALRGVLPTFPDDAKLTKIETLRFAHNYIWALTQT 138
mNGN1bHLH   92 RSRRVKANDRERNRMHNLNAALDALRSVLPSFPDDTKLTKIETLRFAYNYIWALAET 148
               **** ************** ****** *** **** *********** ******  *


hNGN3bHLH vs. mNGN2bHLH

   Aligned Length = 57   Gaps = 0
   Identities = 49 (85%)

hNGN3bHLH   82 RSRRKKANDRERNRMHNLNSALDALRGVLPTFPDDAKLTKIETLRFAHNYIWALTQT 138
mNGN2bHLH  111 KTRRLKANNRERNRMHNLNAALDALREVLPTFPEDAKLTKIETLRFAHNYIWALTET 167
                 ** *** ********** ****** ****** ********************* *
```

POLYNUCLEOTIDES COMPRISING NEUROGENIN3 PROMOTER AND BHLH ENCODING DOMAINS

CROSS-REFERENCE TO RELATED APPLICATIONS

This application is 1) a continuation-in-part of PCT application serial no. PCT/US02/11166, filed Mar. 20, 2002 designating the United States and published in English, and 2) a continuation-in-part of U.S. application Ser. No. 09/817,360, filed Mar. 20, 2001, which application is a continuation-in-part of U.S. application Ser. No. 09/535,145, filed Mar. 24, 2000, which application is entitled to the benefit of U.S. Provisional Application Ser. No. 60/128,180, filed Apr. 6, 1999. The disclosures of each of these applications are incorporated herein by reference in their entireties.

This invention was made with Government support under contract AR049737 awarded by the National Institutes of Health. The Government has certain rights in this invention.

FIELD OF THE INVENTION

The invention relates generally to the field of delivery of insulin to a subject by production of islet cells, particularly insulin producing beta cells, and to islet transcription factors useful in such delivery (e.g., human neurogenin3).

BACKGROUND OF THE INVENTION

Diabetes mellitus is the third leading cause of death in the U.S. and the leading cause of blindness, renal failure, and amputation. Diabetes is also a major cause of premature heart attacks and stroke and accounts for 15% of U.S. health care costs. Approximately 5% of Americans, and as many as 20% of those over the age of 65, have diabetes.

Diabetes results from the failure of the β-cells in the islets of Langerhans in the endocrine pancreas to produce adequate insulin to meet metabolic needs. Diabetes is categorized into two clinical forms: Type 1 diabetes (or insulin-dependent diabetes) and Type 2 diabetes (or non-insulin-dependent diabetes). Type 1 diabetes is caused by the loss of the insulin-producing β-cells. Type 2 diabetes is a more strongly genetic disease than Type 1 (Zonana & Rimoin, 1976 N. Engl. J. Med. 295:603), usually has its onset later in life, and accounts for approximately 90% of diabetes in the U.S. Affected individuals usually have both a decrease in the capacity of the pancreas to produce insulin and a defect in the ability to utilize the insulin (insulin resistance). Obesity causes insulin resistance, and approximately 80% of individuals with Type 2 diabetes are clinically obese (greater than 20% above ideal body weight). Unfortunately, about one-half of the people in the U.S. affected by Type 2 diabetes are unaware that they have the disease. Clinical symptoms associated with Type 2 diabetes may not become obvious until late in the disease, and the early signs are often misdiagnosed, causing a delay in treatment and increased complications. While the role of genetics in the etiology of type 2 diabetes is clear, the precise genes involved are largely unknown.

Insulin is made exclusively by the β-cells in the islets of Langerhans in the pancreas. During development, the islet cells, including the β-cells, develop from an undifferentiated precursor within the growing pancreatic bud. As the bud grows, the undifferentiated cells form into ducts, and it is these cells that function as precursors. Duct cells appear to retain the capacity to differentiate into islet cells throughout life, and in some circumstances when the pancreas is damaged, new islet cells can form from the duct cells. Unfortunately, islet cell regeneration does not appear to occur when the islet cells alone are damaged, such as in type 1 diabetes.

This developmental process is clinically relevant for several reasons. First, the formation of islet cells and especially β-cells is necessary in order to make insulin and control energy metabolism. If the process of β-cell development is in anyway impaired, it predisposes that individual to the later development of diabetes. Therefore genes involved in this process are candidate genes for neonatal diabetes, maturity onset diabetes of the young (MODY) or type 2 diabetes. The sequence of these genes could be used to identify individuals at risk for the development of diabetes, or to develop new pharmacological agents to prevent and treat diabetes.

Second, as discussed above, insulin production is impaired in individuals with diabetes. In type 1 diabetes the impairment is caused by the destruction of the β-cells, while in type 2 diabetes, insulin production is intact, but inadequate. Treatment of type 1 diabetes, as well as many cases of type 2 diabetes, may involve replacement of the β-cells. While replacement of β-cells may be accomplished in several ways, the development of new β-cells from precursor cells, either in culture or in vivo in the patient, would be the most physiologic. To do this, the molecules that control β-cell differentiation are needed.

For these reasons, the diabetes field has spent considerable effort in attempts to identify islet precursor cells, and to develop methods for differentiating beta-cells in vitro. To date this has been largely unsuccessful. The present invention addresses this problem.

LITERATURE

- A cloned fragment of mouse Ngn3 is described in Sommer et al. 1996 Mol. Cell. Neurosci. 8:221.
- cDNA and amino acid sequences of murine Ngn3 and murine mammalian atonal homology 4B (MATH4B) are described at GenBank Accession Nos. U76208 and Y09167, respectively. The human ngn3 gene and mRNA are described at GenBank Accession Nos. AJ133776 and NM_020999, respectively.
- cDNA and amino acid sequences of the rat relax transcriptional regulator are described at GenBank Accession No. Y10619.

SUMMARY OF THE INVENTION

The present invention features polypeptides having activity of human neurogenin3 (hNgn3), and nucleic acid encoding such polypeptide. The invention also features use of islet transcription factors such as hNgn3 to facilitate production of pancreatic islet cells from progenitor cells, and to facilitate insulin delivery by production of islet cells so produced.

BRIEF DESCRIPTION OF THE DRAWINGS

FIGS. 6-8 are photographs showing the expression of the islet hormone in transgenic mice at embryonic day 12.5. Immunohistochemical staining is shown for glucagons in pancreases of a non-transgenic littermate (FIG. 6) and transgenic fetuses expressing ngn3 (FIG. 7) or neuroD1/BETA2 (FIG. 8).

FIG. 9 is a map of the Adeno-X.NeuroD1 and Adeno-X.MASH1 viral construct, which contain the NeuroD1 and Mas1 sequences operably linked to the CMV promoter, respectively.

FIG. 12 is a schematic representation of the promoter shows the relative positions of the transcription start site and the 5' ends of promoter fragments used in the Examples. Some potential sites for transcription factor binding are indicated, including a cluster of sites in the distal promoter. The TATAA box (actual sequence GATAA) is shown 30 by upstream of the transcription start site. FIG. 13 The DNA sequence between positions −3728 and −3653 of the promoter corresponding to cluster 1 is shown (SEQ ID NO:19). Again, potential sites for transcription factor binding are indicated. Two sequences that could potentially function as binding sites for homeodomain proteins of the Hox and related classes are indicated by dashed lines.

FIG. 15A shows an electromobility shift assay demonstrating the binding of transcription factor HNF3β, to the H3-1 probe of the human ngn3 promoter. FIG. 15B shows an electromobility shift assay demonstrating that a proximal site and a distal site in the human Ngn3 promoter can compete equally for binding of HNF3β.

FIG. 17A shows results with NIH3T3 cells transfected with the reporter construct indicated, and co-transfected with the indicated amount of expression plasmid containing the HES1 cDNA ligated downstream of the CMV promoter (vector pBAT12). The luciferase activity is expressed relative to the activity in cells transfected with the reporter plasmid alone. FIG. 17B shows the relative activity of various fragments of the Ngn3 promoter and the Rous Sarcoma virus (RSV) promoter ligated upstream of luciferase in the presence or absence of co-transfection with 90 ng/million cells of the HES1 expression plasmid. FIG. 17C shows fold repression by cotransfected HES1 of luciferase activity from the indicated promoters in NIH 3T3 cells and αTC1.6 cells. Fold repression is the inverse of relative luciferase activity. Transfections were performed in triplicate on at least 3 separate occasions. Errors are shown as +/−the standard error of the mean.

FIG. 18B shows an electromobility shift assay demonstrating that bacterially produced HES1 can bind to the N boxes in the proximal promoter, as well as to a previously characterized site from the mouse HES1 promoter (H1P). Either GST-HES1 or GST protein was incubated with the indicated probes. The far right hand lane shows that the HES1 complex is supershifted by addition of HES1 antiserum. FIG. 18C shows an electromobility shift assay demonstrating the relative ability of HES1 binding sites to compete for binding of the GST-HES1 protein. All three ngn3 promoter sites bind with higher affinity than the previously described HES1 binding site from the HES1 promoter (H1P). In contrast, a 200-fold excess of oligonucleotide E1 (an unrelated E box sequence from the proximal promoter) has no effect on complex formation.

FIG. 19A shows the effect of expression of these vectors on NgN3, ND1, Mash1, MyoD, and β-actin RNA level. FIG. 19B shows the effect of expression of these vectors on glucagon, somatostatin, insulin, IAPP, glucokinase, glucose-transporter 2, and β-actin RNA level. FIG. 19C shows the effect of expression of these vectors on Pax4, Pax6, Nkx2.2, Nkx6.1, Isl-1, and Pdx-1 RNA level.

FIG. 28 is an alignment of the amino acid sequences of hNgn3, murine Ngn3 (mNgn3), and rat Ngn3 (rNgn3) (SEQ ID NOS: 2, 4 and 6).

FIG. 29 provides alignments of the bHLH domain of hNgn3 with bHLH domains of murine Ngn1 (mNgn1) and murine Ngn2 (mNgn2) (SEQ ID NOS: 54-56).

DETAILED DESCRIPTION OF THE INVENTION

Figure 1:
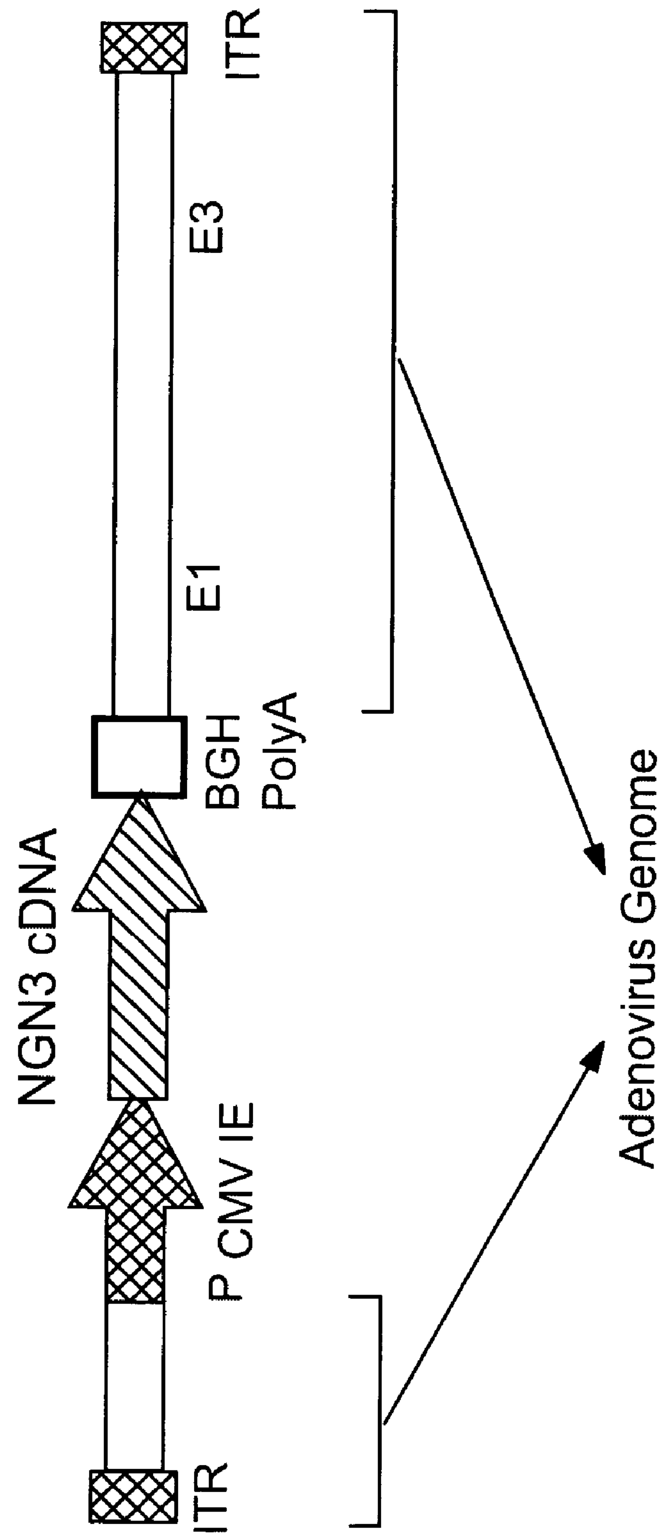
FIG. 1 is a map of the Adeno-X.NGN3 viral construct, which contains the murine neurogenin3 sequence operably linked to the CMV promoter.

Before the present compositions and methods for islet cell and insulin production are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural referents unless the context clearly dictates otherwise. Thus, for example, reference to "an islet transcription factor" includes a plurality of such islet transcription factors and functional equivalents thereof, and reference to "the polynucleotide" includes reference to one or more polynucleotides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

DEFINITIONS

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a Ngn3 polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide, including polynucleotides having substantial sequence similarity or sequence identity relative to the sequences provided herein.

Similarly, "polypeptide" as used herein refers to an oligopeptide, peptide, or protein. Where "polypeptide" is recited herein to refer to an amino acid sequence of a naturally-occurring protein molecule, unless specifically indicated "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein. "Polypeptide" encompasses such molecules without limitation as to method of making, and thus encompasses polypeptides made by recombinant and nonrecombinant methods. "Artificial polypeptides" encompass polypeptides that are not naturally-occurring. "Native" and "naturally-occurring" are used interchangeably herein to refer to polypeptides and nucleic acids having the sequence of a polypeptide or nucleic acid found in nature.

As used herein, "polypeptide" refers to an amino acid sequence of a recombinant or nonrecombinant polypeptide having an amino acid sequence of i) a native polypeptide, ii) a biologically active fragment of a polypeptide, iii) biologically active polypeptide analogs of a polypeptide, or iv) a biologically active variant of a polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, "human Ngn3 polypeptide", "human ND1 polypeptide", or "human Mash1 polypeptide" refers to the amino acid sequences of isolated human Ngn3, ND1, or Mash1 polypeptide, respectively, obtained from a human, and is meant to include all naturally-occurring allelic variants, and is not meant to limit the amino acid sequence to the complete, native amino acid sequence associated with the recited protein molecule.

As used herein, "Ngn3 polypeptide" refers to a recombinant or nonrecombinant polypeptide having an activity of a naturally occurring Ngn3 polypeptide. Ngn3 polypeptides include a polypeptide having an amino acid sequence of i) a native Ngn3 polypeptide, ii) a biologically active fragment of an Ngn3 polypeptide, iii) biologically active polypeptide analogs of an Ngn3 polypeptide, or iv) a biologically active variant of an Ngn3 polypeptide. Ngn3 polypeptides can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, "Human Ngn3 polypeptide" refers to a polypeptide having all or a portion of an amino acid sequence of an Ngn3 polypeptide obtainable from a human, and is meant to include all naturally-occurring allelic variants, and is not meant to limit the amino acid sequence to the complete, native amino acid sequence associated with the recited protein molecule.

The term "basic helix-loop-helix domain" or "bHLH domain" is used herein to describe a polypeptide domain comprised of bipartite domains capable of DNA-binding and protein-protein interactions. The first portion of the bHLH domain, referred to as "the basic domain", contains a high proportion of basic amino acids and directs bHLH proteins to bind to DNA molecules containing the consensus sequence CANNTG (termed an "E box" sequence). The second portion of the bHLH domain, referred to as "the helix-loop-helix domain" or "the HLH domain", contains a high proportion of hydrophobic amino acids, forms two amphipathic alpha-helices separated by a loop of variable length, and allows the protein to interact with and form dimers with other proteins containing helix-loop-helix domains. Together, the bHLH domain also can interact with many other proteins, including, but not limited to, other HLH-containing proteins and other non-bHLH transcription factors.

A "variant" of a polypeptide is defined as a polypeptide that is altered by one or more amino acid residues relative to a reference sequence, e.g., a naturally occurring polypeptide. Such alterations include amino acid substitutions, deletions or insertions, or a combination thereof. Variants of a polypeptide, such as Ngn3, particularly those that have conservative amino acid substitutions, usually retain their basic structural features and biological activity in promoting differentiation of a cell to an islet cell Guidance in determining which and how many amino acid residues may be substituted, inserted or deleted (e.g., without abolishing activity) may be found by comparing the sequence of a polypeptide to the sequence of a polypeptide with a related structure and function e.g., sequences from other sources (e.g., comparison between sequences from mammalian sources, e.g., human, rat, mouse, and the like). Methods for determining activity of a variant in promoting differentiation of a to an islet cell are described herein, and provide for ready assessment of variants.

A "substitution" results from the replacement of one or more amino acids or nucleotides by different amino acids or nucleotides, respectively as compared to an amino acid sequence or polypeptide or nucleic acid. In the context of polypeptides, if a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: gly, ala; val, ile, leu; asp, glu; asn, gln; ser, thr; lys, arg; and phe, tyr. It is understood that, for example, Ngn3 and other transcription factors discussed herein may have conservative amino acid substitutions which have substantially no effect on their activity in promoting differentiation of a cell into an islet cell. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide and polypeptide element amino acid or polynucleotide sequence, a deletion can involve deletion of about 2, about 5, about 10, up to about 20, up to about 30 or up to about 50 or more amino acids. A polypeptide according to the invention may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition to one or more residues within an sequence of a polypeptide or nucleic acid, while "addition" can be an insertion or refer to amino acid residues added at the N- or C-termini of a polypeptide or to nucleotides added to the 5' or 3' ends of a nucleic acid. An insertion or addition may be of up to about 10, up to about 20, up to about 30 or up to about 50 or more amino acids.

The term "biologically active", refers to the activity of a polypeptide, and is normally described with reference to a naturally-occurring polypeptide. For example, a polypeptide that has the biological activity of a human Ngn3 polypeptide has the regulatory or biochemical functions of a naturally occurring human Ngn3 polypeptide in, for example, promoting differentiation of a cell to an islet cell.

The term "derivative" as used herein refers to the chemical modification of a nucleic acid or polypeptide. In the context of nucleic acids, exemplary modifications would be replacement of hydrogen by an alkyl, acyl, or amino group. A nucleic acid derivative would encode a polypeptide which retains essential biological characteristics of a natural polypeptide.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

As used herein, "degenerate variant" refers to a polynucleotide sequence which encodes the same polypeptide as a given polynucleotide sequence, but differs in coding sequence due to the degeneracy of the genetic code. The genetic code is "degenerate" in that two or more different codons can encode the same amino acid.

By "antisense polynucleotide" is mean a polynucleotide having a nucleotide sequence complementary to a given polynucleotide sequence (e.g., a polynucleotide sequence encoding an Ngn3 polypeptide) including polynucleotide sequences associated with the transcription or translation of the given polynucleotide sequence (e.g., a promoter of a polynucleotide encoding an Ngn3 polypeptide), where the antisense polynucleotide is capable of hybridizing to an Ngn3 polypeptide-encoding polynucleotide sequence.

By "nucleic acid of interest" is meant any nucleic acid (e.g., DNA) which encodes a protein or other molecule which is desirable for administration to a mammalian subject. In general, the nucleic acid is operatively linked to other sequences which are needed for its expression, such as a promoter.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

By "transformation" or "transfection" is meant a permanent or transient genetic change induced in a cell following incorporation of new nucleic acid (e.g., DNA or RNA exogenous to the cell). Genetic change can be accomplished either by incorporation of the new nucleic acid into the genome of the host cell, or by transient or stable maintenance of the new DNA as an episomal element.

By "recombinant cell" is meant a cell into which (or into an ancestor of which) has been introduced, by means of recombinant DNA techniques, a DNA molecule encoding a protein of interest.

By "construct" is meant a recombinant nucleic acid, generally recombinant DNA, that has been generated for the purpose of the expression of a specific nucleotide sequence(s), or is to be used in the construction of other recombinant nucleotide sequences.

By "operably linked" or "operably joined" in the context of nucleic acid means that a DNA sequence and a regulatory sequence(s) are connected in such a way as to permit gene expression when the appropriate molecules (e.g., transcriptional activator proteins) are bound to the regulatory sequence(s). "Operably linked" or "operably joined" in the context of a polypeptide means that the portions of the polypeptide are present so as to provide for a polypeptide having a desired biological activity (e.g., promotion of transcriptional activation).

By "heterologous" refers to the situation where a first material is associated with a second material, where the first and second materials are not associated in this manner in nature. For example, where a polypeptide has an activation domain of a human Ngn3 and a bHLH domain of a polypeptide other than human Ngn3, the bHLH domain is heterologous to the activation domain (and vice versa).

By "promoter" is meant at least a minimal sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA.

By "delivery vehicle" or "vector" in the context of recombinant techniques is meant any compound, biological or chemical, which facilitates recombinant modification of a target cell with a DNA of interest. Exemplary biological vectors include viruses, particularly attenuated and/or replication-deficient viruses. Exemplary chemical vectors include lipid complexes and naked DNA constructs.

By "naked DNA" or "naked nucleic acid" or DNA sequence and the like is meant a nucleic acid molecule that is not contained within a viral particle. While not necessary in all applications, naked nucleic acid can optionally be associated (e.g. formulated) with means for facilitating delivery of the nucleic acid to the site of the target cell (e.g., means that facilitate travel into the cell, protect the nucleic acid from nuclease degradation, and the like) and/or to the surface of the target epithelial cell (e.g., adhesive microparticles, ligand-delivery complexes, and the like).

By "pancreas" is meant a large, elongated, racemose gland situated transversely behind the stomach, between the spleen and the duodenum. The pancreas is composed of an endocrine portion (the pars endocrina) and an exocrine portion (the pars exocrina). The pars endocrina, which contains the islets of Langerhans, produces and secretes proteins, including insulin, directly into the blood stream. The pars exocrina contains secretory units and produces and secretes a pancreatic juice, which contains enzymes essential to protein digestion, into the duodenum.

By "euglycemia" or "euglycemic state" is meant a state associated with a level of blood glucose that is normal or nearly normal, particularly relative to the levels of blood glucose in a subject having a disease or condition associated with hyperglycemia. In humans, euglycemia correlates with blood glucose levels in the range of 70 mg/dl to 130 mg/dl.

By "precursor cell" or "progenitor cell" is meant any cell that is capable of developing into an islet cell, particularly upon expression of an islet transcription factor according to the present invention. Such cells include, but are not limited to, fetal pancreatic epithelial cells, adult pancreatic cells (e.g., pancreatic duct cells, acinar cells and pancreatic stem cells), gut epithelial cells, gut stem cells or crypt cells, stem cells from other tissues (such as integumentary, neural, salivary, hematopoietic, mesenchymal or hepatic stem cells), hepatic cells (hepatocytes and hepatic duct cells), multipotent adult progenitor cells from bone marrow (MAPC), embryonic stem cells, germ-line stem cells, cord blood stem cells, and cells derived by somatic cell nuclear transfer.

By "target cell" is meant any cell selected for incorporating DNA encoding a transcription factor nucleotide sequence, including immortalized mammalian cell lines or primary cultured mammalian cells, such as precursor cells, fetal pancreatic epithelial cells, adult pancreatic cells (e.g., pancreatic duct cells, acinar cells and pancreatic stem cells), gut epithelial cells, gut stem cells or crypt cells, stem cells from other tissues (such as hematopoietic, skin, or hepatic stem cells), hepatic cells (hepatocytes and hepatic duct cells), salivary gland cells, neural stem cells, muscle stem cells, and embryonic stem cells, in vivo or in vitro. The use of "target cell" throughout the specification is for convenience only, and is not meant to imply that, for example, accomplishing introduction of a nucleic acid of interest requires the use of targeting techniques (e.g., targeting molecules that preferentially direct the material to be introduced to a particular cell or cell type).

By "islet transcription factor" is meant any transcription factor involved in the differentiation, development, and/or function of islet cells, the expression of which contributes to the production of a cell having an islet cell phenotype, e.g., a cell that produces insulin or other markers characteristic of islet cells, as well as functionally equivalent homologues. Of particular interest are the class B basic helix-loop-helix (bHLH) transcription factors involved in the development of islet cells, which include the neurogenins (neurogeninl, neurogenin2 and neurogenin3), the neuroD factors (NeuroD1/BETA2, neuroD2, and NeuroD4/Math3) and the Mash factor, Mash1, as well as functionally equivalent homologues of these transcription factors.

As used herein, the term "islet transcription factor regulatory pathway" refers to a set of proteins, including signaling molecules and transcription factors, that, in concert through a cascade of activation and deactivation events, regulate the development of pancreatic islet cells and determine the phenotype of the islet cells. A positive regulator of an islet transcription factor pathway is one that promotes expression of a particular islet transcription factor or its downstream effectors and thus positively affects the induction of the islet cell phenotype. A negative regulator of the islet transcription factor pathway is one that inhibits expression of a particular islet transcription factor or its downstream effectors, and thus negatively affects the induction of the islet cell phenotype. Positive regulators include factors that inhibit activity or expression of negative regulators.

As used herein, the term "neurogenin3 (Ngn3) regulatory pathway" refers to a set of proteins, including signaling molecules and transcription factors, that, in concert through a cascade of activation and deactivation events, promote Ngn3 activity and thus direct a cell toward development into a pancreatic islet cells, and facilitates the development or maintenance of the islet cell phenotype. A positive regulator of the Ngn3 pathway is one that promotes expression of Ngn3 or its downstream effectors (e.g., Mash1, NeuroD1, etc.) and thus positively affects the induction of the islet cell phenotype. A negative regulator of the Ngn3 pathway is one that inhibits expression of Ngn3 or its upstream or downstream effectors (e.g., HES1), and thus negatively affects the induction of the islet cell phenotype. Positive regulators of the Ngn3 pathway include factors that inhibit activity or expression of negative regulators of the Ngn3 pathway, or which promote expression of Ngn3. Nucleic acids that encode Ngn3 are examples of positive regulators of the Ngn3 pathway, since these provide for increased expression of Ngn3, and thus promote Ngn3 pathway activity. The HNF transcription factors (e.g., HNF1, HNF3, and HNF6) are further examples of positive regulators of the Ngn3 pathway, since these transcription factors promote (positively regulate) expression of Ngn3.

As used herein, the term "NeuroD1 regulatory pathway" refers to a set of proteins, including signaling molecules and transcription factors, that, in concert through a cascade of activation and deactivation events, promote NeuroD1 activity and thus direct a cell toward development into a pancreatic islet cells, and facilitates the development or maintenance of the islet cell phenotype. A positive regulator of the NeuroD1 pathway is one that promotes expression of NeuroD1 or its downstream effectors (e.g., Mash1, Ngn3, etc.) and thus positively affects the induction of the islet cell phenotype. A negative regulator of the NeuroD1 pathway is one that inhibits its expression of NeuroD1 or its upstream or downstream positive effectors, and thus negatively affects the induction of the islet cell phenotype. Positive regulators of the NeuroD1 pathway include factors that inhibit activity or expression of negative regulators of the NeuroD1 pathway, or which promote expression of NeuroD1. Nucleic acids that encode NeuroD1 are examples of positive regulators of the NeuroD1 pathway, since these provide for increased expression of NeuroD1, and thus promote NeuroD1 pathway activity. Positive regulators include factors that inhibit activity or expression of negative regulators and include nucleic acids that encode NeuroD1. We note that the NeuroD1 regulatory pathway overlaps with the Ngn3 regulatory pathway, in that NeuroD1 acts downstream of Ngn3. Thus Ngn3, as well as positive regulators of Ngn3, are also positive regulators of the NeuroD1 pathway.

As used herein, the term "Mash1 regulatory pathway" refers to a set of proteins, including signaling molecules and transcription factors, that, in concert through a cascade of activation and deactivation events, promote Mash1 activity and thus direct a cell toward development into a pancreatic islet cells, and facilitates the development or maintenance of the islet cell phenotype. A positive regulator of the Mash1 pathway is one that promotes expression of Mash1 or its downstream effectors (e.g., Ngn3, NeuroD1, etc.) and thus positively affects the induction of the islet cell phenotype. A negative regulator of the Mash1 pathway is one that inhibits expression of Mash1 or its upstream or downstream effectors, and thus negatively affects the induction of the islet cell phenotype. Positive regulators include factors that inhibit activity or expression of negative regulators of the Mash1 regulatory pathway, or which promote expression of Mash1. Nucleic acids that encode Mash1 are examples of positive regulators of the Mash1 pathway, since these provide for increased expression of Mash1, and thus promote Mash1 pathway activity. We note that the Mash1 regulatory pathway overlaps with the Ngn3 and NeuroD1 regulatory pathways, in that Mash1 acts upstream of the NeuroD1 and Ngn3 transcription factors. Thus Mash1 is a positive regulator of the NeuroD1 and of the Ngn3 regulatory pathways.

By "islet cell" is meant a cell having a phenotype similar to the hormone-producing cells normally comprising the pancreatic islets of Langerhans, and generally characterized by the expression of markers that normally distinguishing the cells in the pancreatic islets of Langerhans from other pancreatic cells, such as insulin, glucagon, somatostatin, pancreatic polypeptide, or islet amyloid polypeptide.

By "β cell" is meant a pancreatic islet cell having a phenotype characterized by the expression of markers that normally distinguish the beta-cells from the other pancreatic islets cells, such as insulin, Nkx6.1 or glucokinase.

By "α cell" is meant a pancreatic islet cell having a phenotype characterized by the expression of markers that normally distinguish the α-cells from the other pancreatic islets cells, such as proglucagon or glucagons.

By "subject" or "patient" is meant any mammalian subject for whom therapy is desired, particularly humans. Other subjects may include cattle, dogs, cats, guinea pigs, rabbits, rats, mice, horses, and so on. Of particular interest are subjects having an insulin-associated disorder that is amenable to treatment (e.g., to mitigate symptoms associated with the disorder) by expression of either a islet transcription factor-encoding nucleic acid in a cell of the subject (e.g., by introduction of a islet transcription factor-encoding nucleic acid into the subject in vivo, or by implanting cells expressing a islet transcription factor (e.g., β-cell precursors) or nearly developed or mature β-cells cultured from cells expressing a islet transcription factor into the subject, which cells produce insulin).

The terms "treatment", "treating", "treat" and the like are used herein to generally refer to obtaining a desired pharmacologic and/or physiologic effect. The effect may be prophylactic in terms of completely or partially preventing a disease, disorder, or symptom thereof and/or may be therapeutic in terms of a partial or complete stabilization or cure for a disease or disorder and/or any adverse effect attributable to the disease or disorder. "Treatment" as used herein covers any treatment of a disease or disorder in a mammal, particularly a human, and includes: (a) preventing the disease, disorder, or symptom from occurring in a subject which may be predisposed to the disease, disorder or symptom but has not yet been diagnosed as having it; (b) inhibiting the disease, disorder, or symptom, i.e., arresting its development; or relieving the disease, disorder, or symptom, i.e., causing regression of the disease, disorder, or symptom. Thus "treatment of diabetes" thus encompasses one or more of reduction of blood glucose levels, increase in insulin production, and the like.

By "insulin-associated disorder" is meant a disease, disorder, or condition that is caused by or involves, either directly or indirectly, a change in level of insulin production or a change in ability of a subject to utilize insulin, for example, to modulate blood glucose levels. Insulin-associated disorders include, but are not limited to, type 1 diabetes, type 2 diabetes, impaired glucose tolerance, hyperglycemia, hypoglycemia, and the like. Of particular interest are insulin-associated disorder that are amenable to treatment (e.g., to mitigate symptoms associated with the disorder) by expression of either an islet transcription factor-encoding nucleic acid in a cell of the subject (e.g., by introduction of a islet transcription factor-encoding nucleic acid into the subject in vivo, or by implanting cells expressing an islet transcription factor (e.g., β-cell precursors) or nearly developed or mature β-cells cultured from cells expressing an islet transcription factor into the subject, which cells produce insulin).

For sake of clarity, the following table provides a cross-reference of names of transcription factors useful in the present invention, and as used in the present specification with names of the same factors as referred to in the literature as well as the official name of the corresponding human gene.

| Name as used herein | Other names in the literature | Official human gene name* |
|---|---|---|
| neurogenin1 | ngn1; math4C; neuroD3 | NEUROG1 |
| neurogenin2 | ngn2; math4A; ATOH4 | NEUROG2 |
| neurogenin3 | ngn3; math4B; ATOH5; relax | NEUROG3 |
| neuroD1 | BETA2; BHF1; neuroD | NEUROD1 |
| neuroD2 | NDRF; rat4; KW8 | NEUROD2 |
| neuroD4 | math3; neuroM; ath3; ATOH3 | NEUROD4 |
| math2 | ath2; nex1; dlx3; atoh6; ATOH2 | NEUROD6 |
| mash1 | ASH1; HASH1 | ASCL1 |
| mash2 | ASH2; HASH2 | ASCL2 |
| ascl3 | mash5; Sgn-1 | ASCL3 |
| ascl4 | | ASCL4** |
| ascl5 | | ASCL5** |

-continued

| Name as used herein | Other names in the literature | Official human gene name* |
|---|---|---|
| math1 | HATH1 | ATOH1 |
| math5 | HATH5; math7 | ATOH7 |
| math6 | ATOH6; okadin | HATH6** |
| olig1 | Bhlhb6 | OLIG1 |
| olig2 | Bhlhb1; RACK17; RK17; PRKCBP2 | OLIG2 |
| olig3 | Bhlhb7 | OLIG3 |
| bhlhb4 | BETA4; | BHLHB4 |
| bhlhb5 | BETA3; CAGL85; TNRC20 | BHLHB5 |
| ptf1a | p48 | PTF1A** |
| mist1 | Bhlhb8 | MIST1** |
| bhlhf42 | | BHLHF42** |

*As accepted by the Human Gene Nomenclature Committee.

**Approval of name pending.

Other bHLH transcription factors referred to in this application include the myogenic class B bHLH protein myoD, and the ubiquitous class A bHLH protein E47 which is a product of the human E2A gene (official human gene name TCF3). For reviews, see, e.g., McLellan et al., "Exhaustive identification of human class II basic helix-loop-helix proteins by virtual library screening." Gene Expr Patterns. 2002 December; 2(3-4):329-35.

OVERVIEW OF THE INVENTION

The present invention features 1) isolated human neurogenin3 (Ngn3) polypeptide, its encoding nucleic acid, and its associated promoter, as well as human Ngn3 variants that retain activity in promoting differentiation of a progenitor cell into an islet cell; and 2) methods of producing cells having the phenotype of pancreatic islet cells, including insulin-producing β-cells, by expression of an islet transcription factor, such as Ngn3, in a progenitor cell. Providing for increased neurogenin3 (Ngn3) activity in a mature pancreatic cell (a non-beta cell), provides for development of the non-beta pancreatic cell into a cell with the pancreatic beta cell phenotype (e.g., production of insulin).

The nucleotide and amino acid sequences of human Ngn3 are provided as SEQ ID NOS: 1 and 2, respectively. The human Ngn3 polypeptide contains a) a basic helix-loop-helix (bHLH) domain (e.g., residues 82-138 of SEQ ID NO:2) that dimerizes with other bHLH proteins and binds to the consensus DNA sequence CANNTG (an "E box" sequence) and b) an activation domain that, when present in a protein complex that binds to DNA (e.g., residues 190-214 of SEQ ID NO:2), promotes transcription of a DNA sequence operably linked to a promoter containing a protein-binding site (e.g., a site where a transcription factor binds to promoter transcription). That the activation domain is sufficient to promote transcription when present in a DNA-binding polypeptide is evidenced by the GAL4 one hybrid assays, as described in the Examples below. This same assay, or other such similar assays, can be used to optimize the activation domain sequence and to identify variants, as desired. Polypeptides contemplated by the invention include polypeptides characterized by having a bHLH domain similar to that of human Ngn3 (e.g., at least or greater than 85% identical), and having an overall amino acid sequence similarity or identity to human Ngn3, where the polypeptide can lack up to 75 amino acid residues of the N-terminal sequence of SEQ ID NO:2 (native human Ngn3).

Figure 27:
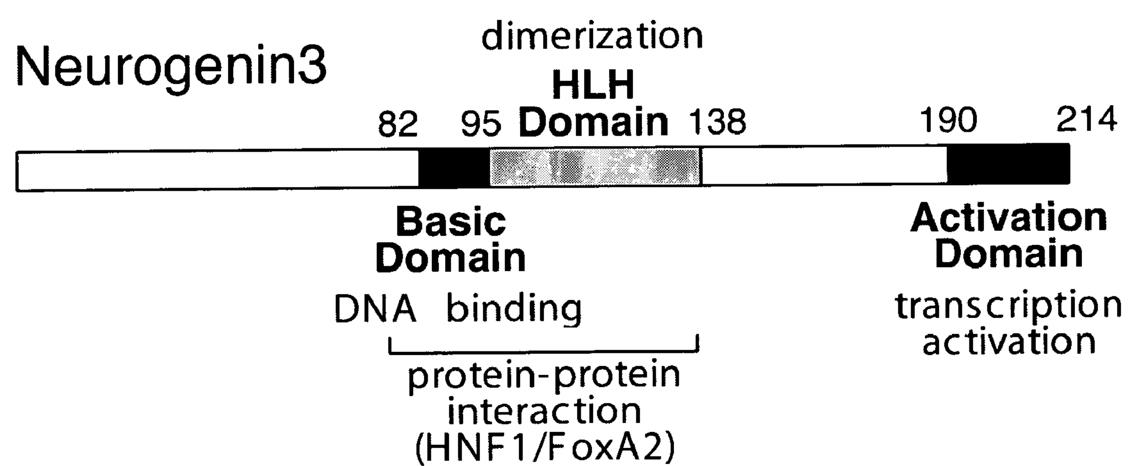
FIG. 27 is a schematic showing the bHLH and activation domains of hNgn3, as well as the minimal portion of hNgn3 required for transcriptional activity.

The invention also contemplates artificial polypeptides (e.g., polypeptides that contain amino acid sequences that from heterologous polypeptides) which contain a bHLH domain similar to that of hNgn3, an activation domain similar to that of hNgn3, or both, linked to heterologous amino acid sequences, where the heterologous sequences can include DNA-binding domains, protein-protein interaction domains, transcription activation domains, or other peptide domains. Such recombinant polypeptides are described in more detail below. FIG. 27 is a schematic showing the domains of hNgn3, and the minimal portion of hNgn3 required for transcriptional activity. These features of hNgn3 are discussed in more detail below.

Islet transcription factors such as Ngn3 are involved in the differentiation and development of islet cells. Islet transcription factors include members of the class B basic helix-loop-helix (bHLH) family of transcription factors, a family of factors known to regulate growth and differentiation of numerous cell types. Islet cells and the developing pancreas express a broad group of class B bHLH genes, among the most abundant being Ngn3, NeuroD1/BETA2, neuroD2, NeuroD4/Math3 and Mash1. NeuroD1 has been shown to be involved in the early differentiation of islet cells and the regulation of insulin transcription in pancreatic beta cells. Neurogenin3 activates the expression of NeuroD1/BETA2 during pancreatic development and therefore neurogenin3 lies upstream of neuroD1 in the hierarchy of islet transcription factors activated during islet cell differentiation. Mash1 can activate Ngn3, and therefore Mash1 can lie upstream of Ngn3 in the hierarchy of islet transcription factors activated during islet cell differentiation.

Ngn3 is expressed in islet cell progenitors and functions as a pro-endocrine gene, driving islet cell differentiation. Ngn3 is expressed early on in the development of all four islet cell types and is involved in the regulation of other islet transcription factors such as Pax4, Pax6, Isl1, and Nkx2.2 as well as NeuroD1/BETA1. Early and ectopic expression of Ngn3 can cause early and ectopic differentiation of islet cells. Other islet transcription factors also include non-bHLH factors such as the homeodomain factors, e.g. Pax4, Pax6, Isl1, Nkx2.2 and Nkx6.1. These factors are immediately downstream (e.g., Pax4, Pax6, Isl1, and Nkx2.2) or upstream of Ngn3 and are involved in islet cell development. The pou-homeodomain factor HNF1 and the winged-helix factor HNF3 lie upstream of Ngn3, and along with the cut-homeodomain factor HNF6 have been implicated in islet cell differentiation and are further examples of islet transcription factors in accordance to the present invention.

An increase in islet transcription factor activity can be accomplished by, for example, directly introducing an islet transcription factor into a cell; introducing an islet transcription factor-encoding polynucleotide into a cell to provide for islet transcription factor expression (which may be in addition to endogenous islet transcription factor expression in the cell); providing for increased levels of expression of a positive regulator of an islet transcription factor (e.g., by introducing a polynucleotide encoding a second transcription factor that positively regulates the islet transcription factor expression, or otherwise increasing activity or expression of such islet transcription factor positive regulators); inhibiting activity (e.g., by inhibiting expression) of a negative regulator or inhibitor of islet transcription factor expression or activity); increasing expression of a downstream effector which is positively regulated by an islet transcription factor; and other variations that will be readily apparent to the ordinarily skilled artisan upon reading the present specification. Modulating of transcription factor expression or activity (e.g., increasing islet transcription factor activity or decreasing expression or activity of an inhibitor of islet transcription factor expression) can also be accomplished by use of signaling molecules (receptors, ligands, intracellular effectors), as well as synthetic and natural small molecule regulators of the pathway.

In one embodiment, an increase in Ngn3 activity can be accomplished by, for example, introducing an Ngn3-encoding polynucleotide into a cell to provide for Ngn3 expression (which may be in addition to endogenous Ngn3 expression in the cell); providing for increased levels of expression of a positive regulator of Ngn3 (e.g., by introducing a polynucleotide encoding a transcription factor that positively regulates Ngn3 expression (e.g., Mash1, HNF1, HNF3, HNF6, etc), or otherwise increasing activity or expression of such Ngn3 positive regulators); inhibiting activity (e.g., by inhibiting expression) of a negative regulator or inhibitor of Ngn3 expression or activity); increasing expression of a downstream effector which is positively regulated by Ngn3 (e.g., neuroD1); and other variations that will be readily apparent to the ordinarily skilled artisan upon reading the present specification. Modulating of Ngn3 expression or activity (e.g., increasing Ngn3 activity or decreasing expression or activity of an inhibitor of Ngn3 expression) can also be accomplished by use of signaling molecules (receptors, ligands, intracellular effectors), as well as synthetic and natural small molecule regulators of the pathway.

In another embodiment, an increase in NeuroD1 activity can be accomplished by, for example, introducing a NeuroD1-encoding polynucleotide into a cell to provide for NeuroD1 expression (which may be in addition to endogenous NeuroD1 expression in the cell); providing for increased levels of expression of a positive regulator of NeuroD1 (e.g., by introducing a polynucleotide encoding a transcription factor that positively regulates NeuroD1 expression (e.g., Mash1, Ngn3, HNF1, HNF3, HNF6, etc.), or otherwise increasing activity or expression of such NeuroD1 positive regulators); inhibiting activity (e.g., by inhibiting expression) of a negative regulator or inhibitor of NeuroD1 expression or activity); increasing expression of a downstream effector which is positively regulated by NeuroD1; and other variations that will be readily apparent to the ordinarily skilled artisan upon reading the present specification. Modulating of NeuroD1 expression or activity (e.g., increasing NeuroD1 activity or decreasing activity or expression of an inhibitor of NeuroD1 expression) can also be accomplished by use of signaling molecules (receptors, ligands, intracellular effectors), as well as synthetic and natural small molecule regulators of the pathway.

In another embodiment, an increase in Mash1 activity can be accomplished by, for example, introducing a Mash1-encoding polynucleotide into a cell to provide for Mash1 expression (which may be in addition to endogenous Mash1 expression in the cell); providing for increased levels of expression of a positive regulator of Mash1 (e.g., by introducing a polynucleotide encoding a transcription factor that positively regulates Mash1 expression, or otherwise increasing activity or expression of such Mash1 positive regulators); inhibiting activity (e.g., by inhibiting expression) of a negative regulator or inhibitor of Mash1 expression or activity); increasing expression of a downstream effector which is positively regulated by Mash1 (e.g., Ngn3, NeuroD1, etc.); and other variations that will be readily apparent to the ordinarily skilled artisan upon reading the present specification. Modulating of Mash1 activity or expression (e.g., increasing Mash1 activity or decreasing expression or activity of an inhibitor of Mash1 expression) can also be accomplished by use of signaling molecules (receptors, ligands, intracellular effectors), as well as synthetic and natural small molecule regulators of the pathway.

The invention generally involves providing for increased expression of at least one islet transcription factor selected from the neurogenic basic helix-loop-helix factors (bHLH) including the neurogenins (neurogenin 1/NEUROG1/MATH4C/NeuroD3, neurogenin2/NEUROG2/MATH4A or neurogenin3/NEUROG3/MATH4B), the neuroD factors (NeuroD1/BETA2/BHF1, NeuroD2/NDRF, MATH2/NEX1/DLX3, NeuroD4/Math3), the Mash factors (Mash1 and Mash2), and the atonal-related factors (MATH1/ATOH1), as well as combinations thereof or combinations with other genes, to provide for induction of pancreatic beta cells. Ngn3 is of particular interest.

Figure 11:
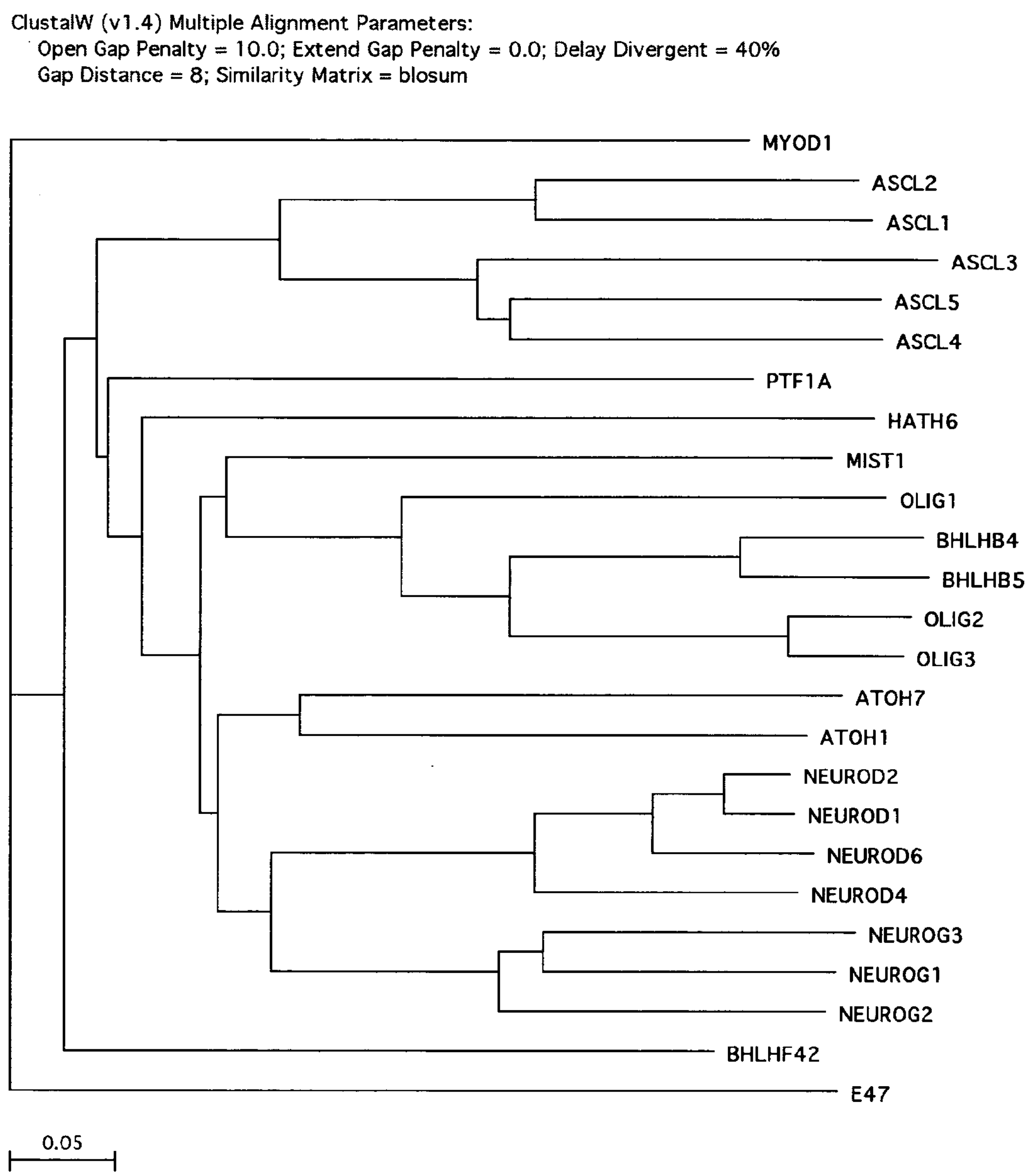
FIG. 11 is a graphical representation of the phylogenetic tree of bHLH proteins. All sequences are human and consist of the bHLH domain plus 10 flanking amino acids on each end of the bHLH domain.

FIG. 11 is a schematic representation of an alignment tree for class B neuroendocrine bHLH proteins, plus myoD (a myogenic class B bHLH protein), and E47 (a class A (ubiquitous) bHLH protein). All are based on human amino acid sequences and are limited to the bHLH domain plus the 10 flanking amino acids on both ends of the bHLH domain. Mouse and human full length sequences exhibit similar alignment profiles. The sequences were aligned using the multiple sequence alignment algorithm Clustal-W as supplied in the MacVector6.5.1 sequence analysis program (Oxford Molecular). The definition of class A and B is based on the classification of Murre et al. (Murre, et al. (1989) Cell 58(3), 537-44). The term "class B bHLH factor" is equivalent to "class II bHLH factor" as used by McLellan et al., Gene Expr Patterns. 2002 December; 2(3-4):329-35.

While Ngn3 is referred to throughout the specification in the context of islet cell production, such reference is not intended to be limiting. Rather Ngn3 is only exemplary of islet transcription factors useful in the invention, and reference to it alone is for clarity and ease in review of the specification. Furthermore, reference to Ngn3 or hNgn3 in this same context is not meant to be limiting to, for example, a naturally-occurring human Ngn3, but is also meant to encompass Ngn3 and hNgn3 variants, which contain at least a minimal sequence of Ngn3 or hNgn3 required to facilitate islet cell production.

We first describe hNgn3 and variants thereof, then the use of islet transcription factors such as hNgn3 in the production of pancreatic beta cells.

Human Ngn3 Polynucleotides, Human Ngn3 Polypeptides, and Variants Thereof

The invention features in one embodiment isolated human Ngn3 (hNgn3) polypeptides, variants thereof, and polynucleotides encoding such polypeptides as well as human and murine Ngn3 promoters.

The DNA and amino acid sequence of a naturally occurring hNgn3 is provided as SEQ ID NOS:1 and 2, respectively. Human Ngn3 polypeptides and variants thereof include both isolated naturally occurring polypeptides, as well as polypeptides having all or a portion(s) of the amino acid sequence of a human Ngn3 polypeptide. Variant polypeptides include, but are not necessarily limited to, polypeptides having at least a DNA-binding bHLH domain, an activation domain, or both. Variant Ngn3 polypeptides include fragments of human Ngn3 polypeptide which retain activity in induction of insulin gene transcription when expressed in a mammalian cell.

It should be noted that the invention contemplates the hNgn3 polypeptides and variants thereof described herein, as well as nucleic acids encoding such variants. When provided with guidance as to the amino acid sequence of a polypeptide—and particularly where exemplary sequences are provided as SEQ ID NOS:1 and 2—the ordinarily skilled artisan can readily design an encoding nucleic acid with reference to the genetic code, which is well known in the art along with methods for production of such encoding nucleic acids.

FIG. 27 is a schematic showing the bHLH and activation domains of hNgn3, as well as the minimal portion of hNgn3 required for transcriptional activity. For example, the 75 N-terminal amino acid residues are not required for hNgn3 activity, and thus can be omitted or be of a different amino acid sequence in the polypeptides of the invention.

The bHLH domain of hNgn3 is about 57 amino acids (171 nts; residues 82 to 138 of SEQ ID NO:2) and has about 85% amino acid sequence identity with the bHLH domains of murine Ngn1 and murine Ngn2 (see FIG. 29). In general, the bHLH domain comprises an amino acid sequence sufficient to provide for dimerizing with other HLH proteins and for binding DNA sequences containing an E box, having the consensus sequence CANNTG.

The activation domain is that portion of hNgn3 that is sufficient to promote transcription of an gene operably linked to a promoter containing a protein binding site when the activation domain is present in a protein or protein complex that binds to that binding site in the promoter. The activation domain of hNgn3 is about 25 amino acids (75 nucleotides) in length (residues 190 to 214 of SEQ ID NO:2). That the activation domain is sufficient to promote transcription when present in a DNA-binding polypeptide is evidenced by the GAL4 one hybrid assays, as described in the Examples below. This same assay, or other such similar assays, can be used to optimize the activation domain sequence and to identify variants, as desired. Guidance for making variants is provided by comparing the amino acid sequences of homologs in non-human Ngn3 proteins, and identifying those residues that are different relative to the hNgn3 activation domain amino acid sequence (see, e.g., the alignment provided in FIG. 28.

FIG. 27 can also provide general guidance as to the overall structure of exemplary polypeptides within the scope of the invention. For example, artificial polypeptides contemplated by the invention include those having an overall structural formula of, from N- to C-terminus, $X_1$-bHLH-$X_2$-AD-$X_3$, where $X_1$, $X_2$, and $X_3$ can be zero or a stretch of amino acid residues of a desired length. For example, $X_1$ in FIG. 27 is about 81 amino acid residues, however from the examples below it is apparent that the first 75 amino acid residues can be eliminated without affecting hNgn3 transcriptional activity. X2 in FIG. 27 (from the C-terminus of the bHLH domain to the N-terminus of the activation domain) is about is about 53 amino acid residues; however, the examples below indicate that this stretch of amino acids can be eliminated without affecting hNgn3 transcriptional activity, and thus X2 could also be, for example, zero (e.g., an hNgn3 polypeptide that lacks residues 139-189). Finally, X3 in FIG. 27 is zero. However, artificial polypeptides in which X1, X2, and X3 are independently 0, 1, 5, 10, 15, 20, 25, 30, 35, 40, 45, 50, 55, 60, 65, 70, 75, 80, 85, 90, 95, or 100 or more amino acid residues are also contemplated by the invention.

Moreover, because various domains of transcription factors can generally function relatively independently without large position effects, the invention also encompasses artificial polypeptides where the bHLH domain and the activation domain (AD) are present in the same or different configuration as in the native hNgn3 exemplified in FIG. 27. For example, the artificial polypeptide may have, from N- to C-terminus, X1-bHLH-X2-AD-X3, or X1-AD-X2-bHLH-X3, where X1, X2, and X3 can be zero or a stretch of amino acid residues of a desired length, as set out above.

The hNgn3 polypeptides of the invention include polypeptides having modifications relative to an hNgn3 amino acid sequence, such as that provided in SEQ ID NO:2. Guidance for amino acid substitutions, deletions, and additions can be obtained by comparison of the amino acid sequence of hNgn3 with Ngn3 of other species. FIG. 28 provides an alignment of the amino acid sequences of hNgn3, murine Ngn3 (mNgn3), and rat Ngn3 (rNgn3), which alignment provides examples of residues that can be modified, e.g., by substitution of a residue of hNgn3 with a residue at that same position in murine or rat Ngn3. FIG. 29 provides alignments of the bHLH domain of hNgn3 with bHLH domains of murine Ngn1 (mNgn1) and murine Ngn2 (mNgn2), and similarly provides guidance as to amino acid sequence modifications that may be made in the bHLH domain of hNgn3.

In one embodiment of interest, polypeptides having Ngn3 activity are characterized as having the following features:

a) a basic helix-loop-helix (bHLH) domain that is at least 90% or 95% identical to the contiguous amino acids 82 to 138 of SEQ ID NO:2;
b) an overall amino acid sequence identity of at least 85%, 90%, or 95% to SEQ ID NO:2 (e.g., the sequence identity of the polypeptide is determined over its entire length relative to all or a portion of a contiguous amino acid sequence of SEQ ID NO:2); and
c) induction of insulin gene transcription when expressed in a suitable mammalian cell.

In general in this context, the mammalian cells contemplated by the invention are those in which insulin gene transcription is induced upon induction of an islet transcription factor regulatory pathway (e.g., Ngn3 regulatory pathway). Optionally, the Ngn3 polypeptide contains a amino acid sequence heterologous to the bHLH domain, e.g., the polypeptide is other than a naturally-occurring polypeptide.

In another embodiment, the invention provides for polypeptides having an activation domain of a human Ngn3 polypeptide. The "activation domain" is a domain of Ngn3 which, when present in a polypeptide, is sufficient to activate transcription of a gene in a mammalian cell. Such Ngn3 activation domain-containing polypeptides are generally characterized as having the following features:

a) an activation domain that is at least 85%, 90%, or 95% identical to amino acid residues 190-214 of SEQ ID NO:2; and
b) activates gene transcription when expressed in a mammalian cell.

Optionally, the recombinant Ngn3 activation domain-containing polypeptide contains a amino acid sequence heterologous to the activation domain, e.g., is other than a naturally-occurring polypeptide. Such polypeptides are of interest as they can be used as general transcriptional activators, e.g., useful in the context of in vitro or in vivo transcription systems, in a manner similar to that in which the activation domain of VP16 is commonly used in the art. Activation of transcription can be assayed using, for example, the GAL4 one hybrid system described in more detail in the Examples below.

In another embodiment, the invention provides polypeptides having Ngn3 activity and characterized as having the following features:

a) a basic helix-loop-helix (bHLH) domain that is at least 90% or 95% identical to amino acids 82 to 138 of SEQ ID NO:2 (which is the amino acid sequence of a naturally occurring human Ngn3 polypeptide);
b) an activation domain that is at least 85%, 90%, or 95% identical to amino acid residues 190-214 of SEQ ID NO:2; and
c) induction of insulin gene transcription when expressed in a mammalian cell.

Optionally, the Ngn3 polypeptide contains an amino acid sequence heterologous to the bHLH domain, e.g., the polypeptide is other than a naturally-occurring polypeptide.

In another embodiment, the polypeptide is further characterized as having an overall amino acid sequence identity of at least 85%, 90%, or 95% to SEQ ID NO:2 (hNgn3). Guidance for amino acid sequence differences relative to the bHLH domain of hNgn3 can be based upon, for example, comparison of the hNgn3 to the amino acid sequence of the bHLH domains of other transcription factors capable of inducing insulin gene transcription when expressed in a suitable mammalian cell.

In other embodiments, the polypeptides of the invention as described above contain a heterologous DNA-binding domain, i.e., a DNA-binding domain that is from a polypeptide other than hNgn3. Exemplary heterologous DNA-binding domains include, but are not necessarily limited to, bHLH domains (e.g., from Ngn1, NeuroD1, Mash1, and the like), DNA-binding domain from GAL4, etc. Such polypeptides can be used in various assays, e.g., to identify interacting proteins (e.g., as in a 2-hybrid screen) or other interacting, regulating molecules. E box-binding DNA-binding domains can be identified using, for example, assays such as those described in the Examples below, see, e.g., Example 22.

In some embodiments it may be desirable to omit the activation domain of hNgn3, as such polypeptides would lack basal transcriptional activation capacity and could serve as a positive control for DNA binding and a negative control in assays to detect transcription activity or as a target to detect protein-protein interactions with other proteins that have transcriptional activation capacity. In a related embodiment, the polypeptide contains a bHLH domain of hNgn3 and a heterologous transcriptional activation domain (e.g., a transcriptional activation domain of VP16, GAL4, and the like). It may be desirable to drive expression of hNgn3-bHLH domain containing proteins which lack the activation domain from a non-hNgn3 promoter so as to avoid repression of expression by the bHLH domain.

In further embodiments, the invention provides polypeptides having Ngn3 activity, where the polypeptide is an N-terminal deletion relative to native hNgn3, where the polypeptide can lack the initial 5, 10, 15, 20, 25, 30, 35, 40, 45, 50, 55, 60, 65, 70, or 75 amino acid residues at the N-terminus relative to native hNgn3 of SEQ ID NO:2. Thus, hNgn3 fragments of interest include those having at least amino acid residues 76-215 of SEQ ID NO:2 and having an amino acid sequence that is at least 90% or 95% identical to the sequence of residues 76-215 of SEQ ID NO:2.

As noted above, the nucleic acid compositions of the subject invention may encode all or a part of the Ngn3 polypeptides as appropriate. In general, DNA fragments encoding hNgn3 will be at least about 75 nts, about 90 nts, about 100 nts, about 150 nts, about 200 nts, about 250 nts, about 400 nts, about 450 nts, about 500 nts, about 750 nts, about 800 nts, about 900 nts, about 1,000 nts, or more in length.

Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Methods for determining amino acid and nucleic acid sequence similarity and identity are known in the art. Substantial sequence identity, when referring to polypeptides of the invention, are polypeptides having at least about 70%, typically at least about 80%, at least about 85%, and preferably at least about 90% to about 95% identity to all or a recited portion of the amino acid sequence of SEQ ID NO: 2, or that are encoded by polynucleotides which will hybridize under stringent conditions to all or a portion of a polynucleotide having the nucleotide sequence of SEQ ID NO:1 (encoding a native hNgn3).

Algorithms for sequence analysis are known in the art, such as BLAST, described in Altschul et al. 1990 J Mol Biol 215:403-10. For the purposes of the present application, percent identity for the polynucleotides of the invention is determined using the BLASTN program with the default settings, with the DUST filter selected. Percent identity for the polypeptides of the invention is determined using the BLASTP program with the default settings with the DUST filter selected. Sequence similarity and identity are calculated based on a reference sequence, which may be a subset of a larger sequence, such as a conserved motif, coding region, flanking region, etc. A reference sequence will usually be at least about 18 residues long, more usually at least about 30 residues, 50 residues, 75 residues, 100 residues, 171 residues, 402 residues, 450 residues, 500 residues long, and may extend to the complete sequence that is being compared.

Nucleic acids having sequence similarity can also be detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human; mammalian sources such as rodents, such as rats and mice; canines; felines; bovines; ovines; equines; and the like The term "Ngn3 gene" is used generically to designate Ngn3 genes and their alternate forms. "Ngn3 gene" is also intended to mean the open reading frame encoding specific Ngn3 polypeptides, introns, and adjacent 5' and 3' non-coding nucleotide sequences involved in the regulation of expression, up to about 1 kb beyond the coding region, but possibly further in either direction. The DNA sequences encoding Ngn3 may be cDNA or genomic DNA or a fragment thereof. The gene may be introduced into an appropriate vector for extrachromosomal maintenance or for integration into the host.

While other genomic Ngn3 sequences of other sources may have non-contiguous open reading frames (e.g., where introns interrupt the protein coding regions), the human genomic Ngn3 sequence has no introns interrupting the coding sequence. A genomic sequence of interest comprises the nucleic acid present between the initiation codon and the stop codon, and may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where Ngn3 is expressed. The sequences of the Ngn3 promoter elements of the invention can be based on the nucleotide sequences of any species (e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human) and can be isolated or produced from any source whether natural, synthetic, semi-synthetic or recombinant.

In one exemplary embodiment, a polynucleotide that comprises a sequence at least 80%, 85%, 90%, or 95% identical to a 5' flanking sequences of an Ngn3 coding sequence (particularly an hNgn3 or murine Ngn3 coding sequence), a polynucleotide that comprises a sequence at least 80%, 85%, 90%, or 95% identical to a 3' flanking sequences of an Ngn3 coding sequence (particularly an hNgn3 or murine Ngn3 coding sequence), or both such 5' and 3' flanking sequences, where the flanking sequences are operably positioned in the expression construct (e.g., a BAC construct) such that these flanking sequences flank a heterologous sequence, such as one or more reporter sequences. An exemplary construct is an expression construct having a sequence at least 80%, 85%, 90%, or 95% identical to SEQ ID NO:1, where all or a portion of the coding sequence has been replaced by a heterologous sequence, particular one encoding a reporter polypeptide. Such constructs can be used to generate transgenic, non-human animals, which can then be used as models of islet cell development, and serve as a surrogate marker for Ngn3 gene activation in the development of islet cells, particularly beta cells. Example 24 illustrates one working example of such a construct, as well as an example of such a transgenic non-human animal model.

The Ngn3-encoding polynucleotide can be isolated and obtained in substantial purity, generally as other than an intact mammalian chromosome. Usually, the DNA will be obtained substantially free of other nucleic acid sequences that do not include an Ngn3 sequence or fragment thereof, generally being at least about 50%, usually at least about 90% pure and are typically “recombinant”, i.e. flanked by one or more nucleotides with which it is not normally associated on a naturally occurring chromosome.

The Ngn3-encoding DNA may be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an Ngn3 sequence is indicative of Ngn3 gene expression in the sample.

The Ngn3 nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like. The sequence of the Ngn3 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of Ngn3 polypeptides with other polypeptides (e.g., Nkx-6.1, which is co-expressed with Ngn3), or to alter properties of the proteins that affect their function or regulation. Such modified Ngn3 sequences can be used to, for example, generate transgenic animals.

Techniques for in vitro mutagenesis of cloned genes are known. Examples of protocols for scanning mutations may be found in Gustin et al., 1993 Biotechniques 14:22; Barany, 1985 Gene 37:111-23; Colicelli et al., 1985 Mol Gen Genet 199:537-9; and Prentki et al., 1984 Gene 29:303-13. Methods for site specific mutagenesis can be found in Sambrook et al., 1989 Molecular Cloning: A Laboratory Manual, CSH Press, pp. 15.3-15.108; Weiner et al., 1993 Gene 126:35-41; Sayers et al., 1992 Biotechniques 13:592-6; Jones and Winistorfer, 1992 Biotechniques 12:528-30; Barton et al., 1990 Nucleic Acids Res 18:7349-55; Marotti and Tomich, 1989 Gene Anal Tech 6:67-70; and Zhu 1989 Anal Biochem 177:120-4.

Ngn3 Promoters

The invention also features Ngn3 promoters and variants thereof, including the murine and human Ngn3 promoter. The sequence of the native murine Ngn3 (mNgn3) promoter is provided as SEQ ID NO:3 and the native human Ngn3 promoter sequence is present in SEQ ID NO:1.

The complete regulatory region corresponding to the human Ngn3 promoter comprises all adjacent sequences on chromosome 10 that contribute to the regulation of the transcription of the human neurogenin3 mRNA. Sequences as short as approximately 207 bp upstream of the transcription start site within the human Ngn3 promoter (e.g., from about nucleotide residue 2435 to the transcriptional start site at 2643 (referred to as +1 herein) in SEQ ID NO:1) can regulate transcription in a mammalian cell. Sequences as long as approximately 6000 bp upstream of the transcription start site to 261 bp downstream of the transcription start site within the human Ngn3 promoter, and approximately 1000 bp downstream of the translation termination site can contribute further transcriptional regulation.

The minimal promoter region of the hNgn3 gene required to drive expression of an operably linked coding sequence in a mammalian cell contains at least a core promoter (a sequence capable of recruiting TFIID and RNA polymerase II, generally containing some combination of BRE, TATA box, Inr and DPE elements). A core promoter is generally located within the region from −40 to +40 bp relative to the transcription start site of a gene, and is recognized by the basal RNA polymerase II transcriptional machinery as defined by Kadonaga (see review exp mol med. 2002 sep 30; 34(4):259-64). The core promoter of the human neurogenin3 gene is composed of sequences from SEQ ID NO:1 from nucleotide residue 2604 to 2683 and contains a potential BRE, TATA box and Inr.

This core element can be present in an isolated polynucleotide comprising a sequence at least 85%, 90%, 95%, or 98% identical to this region in SEQ ID NO:1, and can be flanked by hNgn3 nucleotide sequences, or by nucleotide sequence heterologous to the core element (e.g., the core promoter element can be present in a construct in conjunction and operably linked to heterologous promoter elements, which elements can be artificial (e.g., recombinant or synthetic)). The core promoter element is one that, when operably positioned within the promoter sequence, facilitates detectable levels of transcription of a gene operably linked to the promoter in which the hNgn3 core promoter element is positioned, where transcription occurs when the construct is introduced into an appropriate mammalian cell, either in vitro or in vivo. In one embodiment, the promoter comprises a sequence at least 54 nt, 100 nt, 150 nt, 200 nt, 207 nt, 250 nt, 500 nt, 1,000 nt, 2,000 nt, or more and comprising as sequence at least 85%, 90%, 95%, or 98% identical to a contiguous sequence of the sequence of the promoter set out in SEQ ID NO:1.

Fragments of interest include those having a nucleotide sequence at least 85%, 90%, 95%, or 98% identical to 1) a contiguous nucleotide sequence of nucleotides positioned at −105 to −158 of SEQ ID NO:1 relative to the transcription start site at nucleotide residue 2643 of SEQ ID NO:1; 2) a contiguous nucleotide sequence of nucleotides positioned at −3728 to −3653 of SEQ ID NO:1 relative to the transcription start site at nucleotide residue 2643 of SEQ ID NO:1; 3) a contiguous nucleotide sequence of nucleotides 2435 to 2643 of SEQ ID NO:1; 4) a contiguous nucleotide sequence extending about 2.6 kb 5' of nucleotide residue 2643 of SEQ ID NO:1; 5) a contiguous nucleotide sequence extending about 5.7 kb 5' of nucleotide residue 2643 of SEQ ID NO:1; and 6) a contiguous nucleotide sequence of the sequence extending about 700 bp 5' of nucleotide residue 719 of SEQ ID NO:3.

Similarly, the invention encompasses the murine Ngn3 promoter. The transcriptional start site for the murine Ngn3 at nucleotide residue 719 of SEQ ID NO:3, with the promoter comprising a region approximately 500 bp upstream of the transcription start site. Murine Ngn3 promoters of the invention thus include nucleic acid sequences comprising a sequence at least 85%, 90%, 95%, or 98% identical to the murine Ngn3 promoter sequence.

The invention also encompasses portions of the human or mouse neurogenin3 promoters linked to a heterologous promoter that includes a core promoter. The heterologous promoter can be derived from a naturally occurring gene promoter, could be a synthetic sequence, or some could be some combination of naturally occurring and synthetic sequences, and would minimally include a core promoter, but could also include additional flanking sequences. An example of such a promoter would include, but would not be limited to, the minimal promoter form the HSV thymidine kinase (TK) promoter. Fragments of the neurogenin3 gene of interest that could be linked to a heterologous promoter could include sequences upstream of −40 bp relative to the transcription start site (nucleotide 2604 in SEQ ID NO:1), sequences downstream of the translation termination site (nucleotide 3644 in SEQ ID NO:1). Fragments of particular interest would include sequences from −207 to −40 bp, sequences from approximately −2600 to −40 bp, sequences from approximately −6000 to −40 bp, sequences from-105 TO −158 bp, and sequences from −3728 TO −3653 bp relative to the transcription start site of SEQ ID NO:1, and sequences from −719 to −40 bp in relative to the transcription start site of the murine neurogenin3 gene promoter in SEQ ID NO:3, and would include nucleic acid sequences comprising a sequence at least 85%, 90%, 95%, or 98% identical to these fragments.

The tissue specific expression of Ngn3 is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. 1995 Mol Med 1:194-205; Mortlock et al. 1996 Genome Res. 6: 327-33; and Joulin and Richard-Foy (1995) Eur J Biochem 232: 620-626. 001431 In one embodiment, the Ngn3 promoter is used to direct expression of genes to islet cell precursors. Ngn3 is expressed in islet cell precursors during development of β-cells and other islet cells. Thus, the developmentally timed expression directed by the Ngn3 promoter can be exploited to facilitate expression of heterologous genes operably linked to the Ngn3 promoter. Exemplary genes of interest that can be expressed from the Ngn3 promoter include, but are not necessarily limited to, genes encoding growth factors or onocogenes (e.g., to expand and/or immortalize the islet cell progenitor population), marker genes (e.g., for marking the precursor cells for selection and/or tracing), reporter genes (e.g., luciferase, CAT, etc., for, e.g., identifying mechanisms for regulating the Ngn3 promoter and/or to search for bioactive agents (e.g., candidate pharmaceutical agents) that regulate the promoter), and the like.

The regulatory sequences may be used to identify cis acting sequences required for transcriptional or translational regulation of Ngn3 expression, especially in different tissues or stages of development, and to identify cis acting sequences and trans acting factors that regulate or mediate Ngn3 expression. Such transcriptional or translational control regions may be operably linked to an Ngn3 gene or other genes in order to promote expression of wild type or altered Ngn3 or other proteins of interest in cultured cells, or in embryonic, fetal or adult tissues, and for gene therapy. Ngn3 transcriptional or translational control regions can also be used to identify extracellular signal molecules that regulate Ngn3 promoter activity, and thus regulate Ngn3 expression and islet cell formation.

Production of Ngn3 Polypeptides

The nucleic acids described above may be employed to synthesize full-length Ngn3 polypeptides or variants thereof, particularly fragments corresponding to functional domains such as the activation domain and the bHLH domain; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the Ngn3 genes in mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

hNgn3 Transgenic Animals

The Ngn3-encoding nucleic acids can be used to generate genetically modified non-human animals or site specific gene modifications in cell lines. The term "transgenic" is intended to encompass genetically modified animals having a deletion or other knock-out of Ngn3 gene activity, having an exogenous Ngn3 gene that is stably transmitted in the host cells, "knock-in" having altered Ngn3 gene expression, or having an exogenous Ngn3 promoter operably linked to a reporter gene. Of particular interest are homozygous and heterozygous knock-outs of Ngn3.

Transgenic animals may be made through homologous recombination, where the Ngn3 locus is altered. Alternatively, a nucleic acid construct is randomly integrated into the genome. Vectors for stable integration include plasmids, retroviruses and other animal viruses, YACs, and the like. Of interest are transgenic mammals, preferably a mammal from a genus selected from the group consisting of Mus (e.g., mice), Rattus (e.g., rats), Oryctologus (e.g., rabbits) and Mesocricetus (e.g., hamsters). More preferably the animal is a mouse which is defective or contains some other alteration in Ngn3 gene expression or function. Without being held to theory, Ngn3 is a transcription factor that is expressed in islet cell precursors during pancreatic development, transgenic animals having altered Ngn3 gene expression will be useful models of pancreatic development.

A "knock-out" animal is genetically manipulated to substantially reduce, or eliminate endogenous Ngn3 function, preferably such that target gene expression is undetectable or insignificant. Different approaches may be used to achieve the "knock-out". A chromosomal deletion of all or part of the native Ngn3 homolog may be induced. Deletions of the non-coding regions, particularly the promoter region, 3' regulatory sequences, enhancers, or deletions of gene that activate expression of the Ngn3 genes. A functional knock-out may also be achieved by the introduction of an anti-sense construct that blocks expression of the native Ngn3 gene (for example, see Li and Cohen (1996) Cell 85:319-329).

Conditional knock-outs of Ngn3 gene function can also be generated. Conditional knock-outs are transgenic animals that exhibit a defect in Ngn3 gene function upon exposure of the animal to a substance that promotes target gene alteration, introduction of an enzyme that promotes recombination at the target gene site (e.g., Cre in the Cre-loxP system), or other method for directing the target gene alteration. For example, a transgenic animal having a conditional knock-out of Ngn3 gene function can be produced using the Cre-loxP recombination system (see, e.g., Kilby et al. 1993 Trends Genet 9:413-421). This system can be used in a variety of ways to create conditional knock-outs of Ngn3. For example, two independent transgenic mice can be produced: one transgenic for an Ngn3. sequence flanked by loxP sites and a second transgenic for Cre. The Cre transgene can be under the control of an inducible or developmentally regulated promoter (Gu et al. 1993 Cell 73:1155-1164; Gu et al. 1994 Science 265:103-106), or under control of a tissue-specific or cell type-specific promoter (e.g., a pancreas-specific promoter or brain tissue-specific promoter). The Ngn3 transgenic is then crossed with the Cre transgenic to produce progeny deficient for the Ngn3 gene only in those cells that expressed Cre during development.

Transgenic animals may be made having an exogenous Ngn3 gene. For example, the transgenic animal may comprise a "knock-in" of an Ngn3 gene, such that the host cell genome contains an alteration that results in altered expression (e.g., increased (including ectopic) or decreased expression) of an Ngn3 gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the Ngn3 gene or a homozygous knock-in of the Ngn3. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an Ngn3 polypeptide, or may utilize the Ngn3 promoter operably linked to a reporter gene. Where the introduced gene is a coding sequence, it is usually operably linked to a promoter, which may be constitutive or inducible, and other regulatory sequences required for expression in the host animal.

In another embodiment, the transgenic animal contains an expression construct that provides for Ngn3 promoter element-mediated expression of a heterologous gene, so that expression of the heterologous gene serves as a surrogate marker for activity of the Ngn3 gene, and thus activation of the Ngn3 regulatory pathway. In one exemplary embodiment, the expression construct contains a polynucleotide that comprises a sequence at least 80%, 85%, 90%, or 95% identical to a 5' flanking sequences of an Ngn3 coding sequence (particularly an hNgn3 or murine Ngn3 coding sequence), a polynucleotide that comprises a sequence at least 80%, 85%, 90%, or 95% identical to a 3' flanking sequences of an Ngn3 coding sequence (particularly an hNgn3 or murine Ngn3 coding sequence), or both such 5' and 3' flanking sequences, where the flanking sequences are operably positioned in the expression construct (e.g., a BAC construct) such that these flanking sequences flank a heterologous sequence, such as one or more reporter sequences. An exemplary construct is an expression construct having a sequence at least 80%, 85%, 90%, or 95% identical to SEQ ID NO:1, where all or a portion of the coding sequence has been replaced by a heterologous sequence, particular one encoding a reporter polypeptide. Such constructs can be used to generate transgenic, non-human animals, which can then be used as models of islet cell development, and serve as a surrogate marker for Ngn3 gene activation in the development of islet cells, particularly beta cells. Example 24 illustrates one working example of such a construct, as well as an example of such a transgenic non-human animal model.

Specific constructs of interest include, but are not limited to, anti-sense Ngn3, small interfering RNA (siRNA or RNAi), or a ribozyme based on an Ngn3 sequence, which will block Ngn3 expression, as well as expression of dominant negative Ngn3 mutations, and over-expression of an Ngn3 gene. A detectable marker, such as lac Z may be introduced into the Ngn3 locus, where upregulation of expression of the corresponding Ngn gene will result in an easily detected change in phenotype. Constructs utilizing a promoter region of the Ngn3 genes in combination with a reporter gene or with the coding region of Ngn3 are also of interest. Constructs having a sequence encoding a truncated or altered (e.g, mutated) Ngn3 are also of interest.

The modified cells or animals are useful in the study of function and regulation of Ngn3 and other proteins involved the pancreatic β-cell developmental pathway. Such modified cells or animals are also useful in, for example, the study of the function and regulation of genes whose expression is affected by Ngn3, as well as the study of the development of insulin-secreting cells in the pancreas. Thus, the transgenic animals of the invention are useful in identifying downstream targets of Ngn3, as such targets may have a role in the phenotypes associated with defects in Ngn3.

Animals may also be used in functional studies, drug screening, etc., e.g. to determine the effect of a candidate drug on islet cell development, on β-cell function and development or on symptoms associated with disease or conditions associated with Ngn3 defects (e.g., on symptoms associated with reduced insulin secretion (e.g., such as that associated with a diabetic syndrome, including Type 2 diabetes). A series of small deletions and/or substitutions may be made in the Ngn3 genes to determine the role of different polypeptide-encoding regions in DNA binding, transcriptional regulation, etc. By providing expression of Ngn3 protein in cells in which it is otherwise not normally produced (e.g., ectopic expression), one can induce changes in cell behavior. These animals are also useful for exploring models of inheritance of disorders associated with diabetes, e.g. dominant v. recessive; relative effects of different alleles and synergistic effects between Ngn3 and other genes elsewhere in the genome.

DNA constructs for homologous recombination will comprise at least a portion of the Ngn3 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185: 527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wildtype animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well-characterized, such as *C. elegans, D. melanogaster* and *S. cerevisiae*. For example, transposon (Tcl) insertions in the nematode homolog of an Ngn3 gene or a promoter region of an Ngn3 gene may be made. The Ngn3 gene sequences may be used to knock-out or to complement defined genetic lesions in order to determine the physiological and biochemical pathways involved in function of islet cells. It is well known that human genes can complement mutations in lower eukaryotic models.

Induction of Beta-Cell Development

Pancreatic beta-cells can be produced from non-beta cell pancreatic cells by providing for production of an islet transcription factor in a pancreatic cell either in vivo (e.g., by administration of islet transcription factor-encoding nucleic acid (e.g., RNA or DNA) to the pancreas of a subject, e.g., by introduction of nucleic acid into a lumen of a pancreatic duct), or in vitro, e.g., by contacting a target cell (e.g., an isolated, non-beta, pancreatic cell) with islet transcription factor-encoding nucleic acid (e.g., RNA or DNA) in culture (which cells are then cultured, expanded, and transplanted into a subject).

Expression of an islet transcription factor in the target cell can be accomplished by a variety of methods. For example, in one embodiment, islet transcription factor expression is accomplished by introduction of islet transcription factor-encoding nucleic acid (e.g., DNA or RNA) to provide for expression of the encoded islet transcription factor polypeptide in the target cell). In another embodiment islet transcription factor expression is induced by introduction of a gene encoding a protein that provides for induction of islet transcription factor expression (e.g., expression of an "upstream" positive regulator of islet transcription factor expression in the target cell). In another embodiment, islet transcription factor expression is accomplished by introduction of a gene encoding a protein that inhibits activity (e.g., function or expression) a negative regulator of islet transcription factor expression. In another embodiment islet transcription factor expression is induced by introduction of a small molecule that provides for induction of islet transcription factor expression (e.g., a small molecule pharmaceutical that induces islet transcription factor expression in the target cell). In addition, production of pancreatic beta cells of the invention can also be accomplished by providing for production of factors induced by an islet transcription factor.

In one embodiment of particular interest, beta cells are produced by providing for expression of neurogenin3 (Ngn3) at a level sufficient to induce the beta cell phenotype in a target cell. In one embodiment, Ngn3 expression is accomplished by introduction of Ngn3-encoding nucleic acid (e.g., DNA or RNA) to provide for expression of the encoded Ngn3 polypeptide in the target cell) or by introduction of Ngn3 polypeptide into the cell (e.g., by importing the polypeptide using a molecular tag or by microinjection). In another embodiment Ngn3 expression is induced by introduction of a gene encoding a protein that provides for induction of Ngn3 expression (e.g., expression of an "upstream" positive regulator of Ngn3 expression in the target cell (e.g., Mash1, HNF1, HNF3, HNF6, etc.)). In another embodiment, Ngn3 expression is accomplished by introduction of a gene encoding a protein that inhibits activity (e.g., function or expression) of a negative regulator of Ngn3 expression. In another embodiment Ngn3 expression is induced by introduction of a small molecule that provides for induction of Ngn3 expression (e.g., a small molecule pharmaceutical that induces Ngn3 expression in the target cell). In addition, production of pancreatic beta cells of the invention can also be accomplished by providing for production of factors induced by Ngn3. The invention requires only a transient increase in Ngn3 activity in the cell, e.g., for a time and in an amount sufficient to stimulate the Ngn3 transcriptional cascade.

In another embodiment, beta cells are produced by providing for expression of NeuroD1 at a level sufficient to induce the beta cell phenotype in a target cell. In one embodiment, NeuroD1 expression is accomplished by introduction of NeuroD1-encoding nucleic acid (e.g., DNA or RNA) to provide for expression of the encoded NeuroD1 polypeptide in the target cell). In another embodiment NeuroD1 expression is induced by introduction of a gene encoding a protein that provides for induction of NeuroD1 expression (e.g., expression of an "upstream" positive regulator of NeuroD1 expression in the target cell (e.g., Mash1, Ngn3, HNF1, HNF3, HNF6, etc.)). In another embodiment, NeuroD1 expression is accomplished by introduction of a gene encoding a protein that inhibits activity (e.g., function or expression) of a negative regulator of NeuroD1 expression. In another embodiment NeuroD1 expression is induced by introduction of a small molecule that provides for induction of NeuroD1 expression (e.g., a small molecule pharmaceutical that induces NeuroD1 expression in the target cell). In addition, production of pancreatic beta cells of the invention can also be accomplished by providing for production of factors induced by NeuroD1.

In another embodiment, beta cells are produced by providing for expression of Mash1 at a level sufficient to induce the beta cell phenotype in a target cell. In one embodiment, Mash1 expression is accomplished by introduction of Mash1-encoding nucleic acid (e.g., DNA or RNA) to provide for expression of the encoded Mash1 polypeptide in the target cell). In another embodiment Mash1 expression is induced by introduction of a gene encoding a protein that provides for induction of Mash1 expression (e.g., expression of an "upstream" positive regulator of Mash1 expression in the target cell). In another embodiment, Mash1 expression is accomplished by introduction of a gene encoding a protein that inhibits activity (e.g., function or expression) a negative regulator of Mash1 expression. In another embodiment Mash1 expression is induced by introduction of a small molecule that provides for induction of Mash1 expression (e.g., a small molecule pharmaceutical that induces Ngn3 expression in the target cell). In addition, production of pancreatic beta cells of the invention can also be accomplished by providing for production of factors induced by Mash1.

As will be readily appreciated by the ordinarily skilled artisan upon reading the present disclosure, islet transcription factor expression can be accomplished by providing for any combination of these approaches. For example, the invention also provides for expression in the target cell of both an islet transcription factor-encoding nucleic acid as well as a positive regulator of an endogenous islet transcription factor gene; providing for expression of an introduced islet transcription factor nucleic acid as well as an inhibitor of a negative regulator of an endogenous islet transcription factor and introduced islet transcription factor sequence; and the like. In general, any combination of the approaches that provide for islet transcription factor activity by, for example, providing for expression of islet transcription factor per se (by introduction of islet transcription factor-encoding nucleic acid or providing for expression of endogenous islet transcription factor) and/or by providing of production of factors "downstream" of an islet transcription factor that are normally produced as a result of expression of the islet transcription factor, are within the scope of the present invention.

In one embodiment, the invention provides for expression in the target cell of both an Ngn3-encoding nucleic acid as well as a positive regulator of an endogenous Ngn3 gene (e.g., Mash1, HNF1, HNF3, HNF6, etc.); providing for expression of an introduced Ngn3 nucleic acid as well as an inhibitor of a negative regulator of an endogenous Ngn3 and introduced Ngn3 sequence; and the like. In general, any combination of the approaches that provide for Ngn3 activity by, for example, providing for expression of Ngn3 per se (by introduction of Ngn3-encoding nucleic acid or providing for expression of endogenous Ngn3) and/or by providing of production of factors "downstream" of Ngn3 that are normally produced as a result of Ngn3 expression (e.g., NeuroD1, etc.), are within the scope of the present invention. Positive regulators of Ngn3 expression include, but are not necessarily limited to Mash1, HNF1, HNF3, and HNF6.

In another embodiment, the invention provides for expression in the target cell of both an NeuroD1-encoding nucleic acid as well as a positive regulator of an endogenous NeuroD1 gene (e.g., Mash1, Ngn3, HNF1, HNF3, HNF6, etc.); providing for expression of an introduced NeuroD1 nucleic acid as well as an inhibitor of a negative regulator of an endogenous NeuroD1 and introduced NeuroD1 sequence; and the like. In general, any combination of the approaches that provide for Ngn3 activity by, for example, providing for expression of NeuroD1 per se (by introduction of NeuroD1-encoding nucleic acid or providing for expression of endogenous NeuroD1) and/or by providing of production of factors "downstream" of NeuroD1 that are normally produced as a result of Ngn3 expression, are within the scope of the present invention. Positive regulators of NeuroD1 expression include, but are not necessarily limited to Mash1, Ngn3, HNF1, HNF3, and HNF6.

In another embodiment, the invention provides for expression in the target cell of both an Mash1-encoding nucleic acid as well as a positive regulator of an endogenous Mash1 gene; providing for expression of an introduced Mash1 nucleic acid as well as an inhibitor of a negative regulator of an endogenous Mash1 and introduced Mash1 sequence; and the like. In general, any combination of the approaches that provide for Mash1 activity by, for example, providing for expression of Mash1 per se (by introduction of Mash1-encoding nucleic acid or providing for expression of endogenous Mash1) and/or by providing of production of factors "downstream" of Mash1 that are normally produced as a result of Mash1 expression (e.g., Ngn3, NeuroD1, etc.), are within the scope of the present invention.

In addition, induction of the activity of an islet transcription factor pathway can be accomplished using naturally occurring or synthetic molecules other than nucleic acid. For example, islet transcription factor activity can be induced by using a synthetic molecule that promotes expression of an islet transcription factor involved in the pathway, e.g., by inhibiting activity of a negative regulator of expression of the islet transcription factor.

In one embodiment, induction of the activity of the Ngn3 regulatory pathway is accomplished using naturally occurring or synthetic molecules other than nucleic acid. For example, Ngn3 activity is induced by using a synthetic molecule that promotes Ngn3 expression, e.g., by inhibiting activity of a negative regulator of Ngn3 expression. Inhibitory transcription factors of Ngn3 expression include, but are not necessarily limited to HES1. Negative signaling pathways that inhibit Ngn3 expression include, but are not necessarily limited to, the Notch pathway.

In another embodiment, induction of the activity of the NeuroD1 regulatory pathway is accomplished using naturally occurring or synthetic molecules other than nucleic acid. For example, NeuroD1 activity is induced by using a synthetic molecule that promotes NeuroD1 expression, e.g., by inhibiting activity of a negative regulator of NeuroD1 expression.

In another embodiment, induction of the activity of the Mash1 regulatory pathway is accomplished using naturally occurring or synthetic molecules other than nucleic acid. For example, Mash1 activity is induced by using a synthetic molecule that promotes Mash1 expression, e.g., by inhibiting activity of a negative regulator of Mash1 expression.

Islet Transcription Factor Nucleic Acids and Polypeptides

The term "islet transcription factor gene" is used to designate both transcription factors that are expressed in pancreatic islet cells, and also transcription factors that are involved in the development, differentiation, or formation of islet cells. The term "islet transcription factor gene" is also intended to mean the open reading frame encoding specific islet transcription factor polypeptides, introns, and adjacent 5' and 3' non-coding nucleotide sequences involved in the regulation of expression, up to about 2.5 kb, about 5 kb, 10 kb, or about 15 kb beyond the coding region, but possibly further in either direction. The DNA sequences encoding an islet transcription factor may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

An islet transcription factor genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 2.5 kb, about 5 kb, about 10 kb, or about 15 kb, but possibly more, of flanking genomic DNA at either the 5' or 3' end of the transcribed region. The genomic DNA may be isolated as a large fragment of 100 kbp or more, or as a smaller fragment substantially free of flanking chromosomal sequence.

The sequence of this 5' region, and further 5' upstream sequences and 3' downstream sequences, may be utilized for promoter elements, including enhancer binding sites, that provide for expression in tissues where the islet transcription factor is expressed. The sequences of the islet transcription factor promoter elements of the invention can be based on the nucleotide sequences of any species (e.g., mammalian or non-mammalian (e.g., reptiles, amphibians, avian (e.g., chicken)), particularly mammalian, including human, rodent (e.g., murine or rat), bovine, ovine, porcine, murine, or equine, preferably mouse or human) and can be isolated or produced from any source whether natural, synthetic, semi-synthetic or recombinant.

The nucleic acid compositions used in the subject invention may encode all or a part, usually at least substantially all, of the islet transcription factor polypeptides as appropriate. Fragments of the DNA sequence may be obtained by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The islet transcription factor genes are isolated and obtained in substantial purity, generally as other than an intact mammalian chromosome. Usually, the DNA will be obtained substantially free of other nucleic acid sequences that do not include a sequence encoding an islet transcription factor or fragment thereof, generally being at least about 50%, usually at least about 90% pure and are typically "recombinant", i.e. flanked by one or more nucleotides with which it is not normally associated on a naturally occurring chromosome.

The sequence of the islet transcription factor, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two, or by at least about ten nucleotides or amino acids. In general, the sequence changes may be substitutions, insertions or deletions. Deletions may further include larger changes, such as deletions of a domain or exon. It should be noted that islet transcription factor sequences are conserved mainly within the bHLH domain, and regions outside this domain may not be as well-conserved, and may even be remarkably poorly conserved, between, for example, rat, mouse, and humans. Thus islet transcription factors can tolerate more nucleotide and amino acid residue changes outside of the bHLH domain and retain function to a much greater extent than changes made within the bHLH domain. Such modified islet transcription factor sequences can be used, for example, to generate vectors for introduction into target cells for the purpose of producing islet cells.

Techniques for in vitro mutagenesis of cloned genes are known. Examples of protocols for scanning mutations may be found in Gustin et al., 1993 Biotechniques 14:22; Barany, 1985 Gene 37:111-23; Colicelli et al., 1985 Mol Gen Genet 199:537-9; and Prentki et al., 1984 Gene 29:303-13. Methods for site specific mutagenesis can be found in Sambrook et al., 1989 Molecular Cloning: A Laboratory Manual, CSH Press, pp. 15.3-15.108; Weiner et al., 1993 Gene 126:35-41; Sayers et al., 1992 Biotechniques 13:592-6; Jones and Winistorfer, 1992 Biotechniques 12:528-30; Barton et al., 1990 Nucleic Acids Res 18:7349-55; Marotti and Tomich, 1989 Gene Anal Tech 6:67-70; and Zhu 1989 Anal Biochem 177:120-4.

An islet transcription factor of particular interest in the present invention is a member of the neurogenin transcription factor family, e.g., neurogenin 1 (Ngn1), neurogenin2 (Ngn2), neurogenin 3 (Ngn3), with Ngn3 being of particular interest. The nucleotide and amino acid sequences of human Ngn3 are provided in the Sequence Listing as SEQ ID NOS:1 and 2, respectively.

The nucleotide and amino acid sequences of human Ngn1 are available at GenBank accession number XM_003834 (provided in the Sequence Listing as SEQ ID NOS: 20 and 21, respectively) and NM_006161 (provided in the Sequence Listing as SEQ ID NOS: 22 and 23, respectively). Cloning and expression of human Ngn1 is described in, for example, McCormick et al. (1996) Mol. Cell. Biol. 16 (10), 5792-5800; and Tamimi et al. (1997) Genomics 40 (2), 355-357 (1997).

The nucleotide and amino acid sequence of human Ngn2 are available at GenBank accession number AF303002 (provided in the Sequence Listing as SEQ ID NOS: 24 and 25, respectively) and XM_067897 (provided in the Sequence Listing as SEQ ID NOS: 26 and 27, respectively). Cloning and expression of human Ngn1 is described in, for example, Simmons et al. (2001) Dev. Biol. 229 (2), 327-339.

It should be noted that transcription factors which act either "upstream" of Ngn3 (and therefore activate Ngn3 expression) or "downstream" of Ngn3, that lead to development of the islet cell phenotype, are also contemplated for use in the present invention.

Neurogenin3 by itself is sufficient to force undifferentiated pancreatic epithelial cells to become islet cells. Since neurogenin3 expression determines which precursor cells will differentiate into islet cells, the signals that regulate neurogenin3 expression are also involved in islet cell formation. Although 2.7 kb of the ngn3 promoter is sufficient to direct expression correctly in transgenic mice, distal sequences have been shown to greatly enhance the expression of ngn3. This distal promoter region contains a cluster of binding sites for pancreatic transcription factors such as, HNF6, HNF1$\alpha$, and HNF3$\beta$. These pancreatic transcription factors have been found to regulate ngn3 gene expression and thereby are also involved in the control of islet cell formation. These signals may be useful in generating new islet cells for patients with diabetes mellitus.

In another embodiment, the islet transcription factor is a member of the neuroD family of transcription factors, e.g. NeuroD1, NeuroD2, NeuroD4, with NeuroD1 being of particular interest. The sequence of the human NeuroD1 gene and the corresponding human NeuroD1 amino acid sequence are available at GenBank accession number NM_002500 (provided in the Sequence Listing as SEQ ID NOS: 28 and 29, respectively), as well as at XM_002573 (provided in the Sequence Listing as SEQ ID NOS: 30 and 31, respectively) and at AF045152 (provided in the Sequence Listing as SEQ ID NOS: 32 and 33, respectively). Cloning and expression of human NeuroD1 is described in, for example, Lee et al. (1995) Science 268 (5212), 836-844; Tamimi et al. (1996) Genomics 34 (3), 418-421; Yokoyama et al. (1996) DNA Res. 3 (5), 311-320; and Yokoyama et al. (1196) Brain Res. Mol. Brain Res. 42 (1), 135-139.

The human NeuroD4 gene and the corresponding human NeuroD4 amino acid sequence are available at GenBank accession number AF203901 (provided in the Sequence Listing as SEQ ID NOS: 34 and 35, respectively).

It should be noted that transcription factors which act either "upstream" of NeuroD1 (and therefore activate NeuroD1 expression) or "downstream" of NeuroD1, that lead to development of the islet cell phenotype, are also contemplated for use in the present invention.

In another embodiment, the islet transcription factor is a member of the Mash family of transcription factors, e.g. Mash1, Mash2, with Mash1 being of particular interest. The sequence of the human Mash1 gene and the corresponding Mash1 amino acid sequence are available at GenBank accession number XM_006688 (provided in the Sequence Listing as SEQ ID NOS: 36 and 37, respectively), as well as at NM_004316 (provided in the Sequence Listing as SEQ ID NOS: 38 and 39, respectively). Cloning and expression of human Mash1 is described in, for example, Ball et al. (1993) Proc. Natl. Acad. Sci. U.S.A. 90 (12), 5648-5652; Renault et al. (1995) Genomics 30 (1), 81-83; Borges et al. (1997) Nature 386 (6627), 852-855; and Chen et al. (1997) Cell Growth Differ. 8 (6), 677-686.

It should be noted that transcription factors which act either "upstream" of Mash1 (and therefore activate Mash1 expression) or "downstream" of Mash1, that lead to development of the islet cell phenotype, are also contemplated for use in the present invention.

Where the islet transcription factor nucleic acid to be delivered is DNA, any construct having a promoter (e.g., a promoter that is functional in a eukaryotic cell) operably linked to a DNA of interest can be used in the invention. The constructs containing the DNA sequence (or the corresponding RNA sequence) which may be used in accordance with the invention may be any eukaryotic expression construct containing the DNA or the RNA sequence of interest. For example, a plasmid or viral construct (e.g. adenovirus) can be cleaved to provide linear DNA having ligatable termini. These termini are bound to exogenous DNA having complementary-like ligatable termini to provide a biologically functional recombinant DNA molecule having an intact replicon and a desired phenotypic property. Preferably the construct is capable of replication in eukaryotic and/or prokaryotic hosts (viruses in eukaryotic, plasmids in prokaryotic), which constructs are known in the art and are commercially available.

The constructs can be prepared using techniques well known in the art. Likewise, techniques for obtaining expression of exogenous DNA or RNA sequences in a genetically altered host cell are known in the art (see, for example, Kormal et al., Proc. Natl. Acad. Sci. USA, 84:2150-2154, 1987; Sambrook et al. Molecular Cloning: a Laboratory Manual, 2nd Ed., 1989, Cold Spring Harbor Laboratory Press, Cold Spring Harbor, N.Y., each of which are hereby incorporated by reference with respect to methods and compositions for eukaryotic expression of a DNA of interest).

In one embodiment, the DNA construct contains a promoter to facilitate expression of the DNA of interest within a pancreatic cell. The promoter may be a strong, viral promoter that functions in eukaryotic cells such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521-530, 1985) and the promoter from the long terminal repeat (LTR) of RSV (Gorman et al., *Proc. Natl. Acad. Sci. USA* 79:6777-6781, 1982). Of these two promoters, the CMV promoter is presently preferred as it provides for higher levels of expression than the RSV promoter.

Alternatively, the promoter used may be a strong general eukaryotic promoter such as the actin gene promoter. In one embodiment, the promoter used may be a tissue-specific promoter. For example, the promoter used in the construct may be a pancreas specific promoter, a duct cell specific promoter or a stem cell specific promoter. The constructs of the invention may also include sequences in addition to promoters which enhance expression in the target cells.

In another embodiment, the promoter is a regulated promoter, such as a tetracycline-regulated promoter, expression from which can be regulated by exposure to an exogenous substance (e.g., tetracycline.).

Other components such as a marker (e.g., an antibiotic resistance gene (such as an ampicillin resistance gene) or β-galactosidase) aid in selection or identification of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression, the construct should contain at a minimum a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used (e.g., the human.-globin intron, which is inserted in the construct at a position 5' to the DNA of interest).

In an alternative embodiment, the nucleic acid delivered to the cell is an RNA encoding an islet transcription factor. In this embodiment, the RNA is adapted for expression (i.e., translation of the RNA) in a target cell. Methods for production of RNA (e.g., mRNA) encoding a protein of interest are well known in the art, and can be readily applied to the product of RNA encoding islet transcription factors useful in the present invention.

Delivery of Islet Transcription Factor-Encoding Nucleic Acid

Delivery of islet transcription factor-encoding nucleic acid can be accomplished using a viral or a non-viral vector. In one embodiment the nucleic acid is delivered within a viral particle, such as an adenovirus. In another embodiment, the nucleic acid is delivered in a formulation comprising naked DNA admixed with an adjuvant such as viral particles (e.g., adenovirus) or cationic lipids or liposomes. An "adjuvant" is a substance that does not by itself produce the desired effect, but acts to enhance or otherwise improve the action of the active compound. The precise vector and vector formulation used will depend upon several factors, such as the size of the DNA to be transferred, the delivery protocol to be used, and the like. Exemplary non-viral and viral vectors are described in more detail below.

Viral Vectors

In general, viral vectors used in accordance with the invention are composed of a viral particle derived from a naturally-occurring virus which has been genetically altered to render the virus replication-defective and to deliver a recombinant gene of interest for expression in a target cell in accordance with the invention.

Numerous viral vectors are well known in the art, including, for example, retrovirus, adenovirus, adeno-associated virus, herpes simplex virus (HSV), cytomegalovirus (CMV), vaccinia and poliovirus vectors. Adenovirus and AAV are usually preferred viral vectors since these viruses efficiently infect slowly replicating and/or terminally differentiated cells. The viral vector may be selected according to its preferential infection of the cells targeted.

Where a replication-deficient virus is used as the viral vector, the production of infectious virus particles containing either DNA or RNA corresponding to the DNA of interest can be achieved by introducing the viral construct into a recombinant cell line which provides the missing components essential for viral replication. In one embodiment, transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., *Science* 252:431-434, 1991 and Rosenfeld et al., *Cell* 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., *J. Virol.* 67:2928-2931, 1993; Takeuchi et al., *Archiv. Virol.,* 128:177-183, 1993; Tanabayashi et al., *Virol.* 187:801-804, 1992; Kawano et al., *Virol.,* 179:857-861, 1990; Elango et al., *J. Gen. Virol.* 69:2893-28900, 1988.

Non-Viral Vectors

The nucleic acid of interest may be introduced into a cell using a non-viral vector. "Non-viral vector" as used herein is meant to include naked DNA (e.g., DNA not contained within a viral particle, and free of a carrier molecules such as lipids), chemical formulations comprising naked nucleic acid (e.g., a formulation of DNA (and/or RNA) and cationic compounds (e.g., dextran sulfate, cationic lipids)), and naked nucleic acid mixed with an adjuvant such as a viral particle (e.g., the DNA of interest is not contained within the viral particle, but the formulation is composed of both naked DNA and viral particles (e.g., adenovirus particles) (see, e.g., Curiel et al. 1992 Am. J. Respir. Cell Mol. Biol. 6:247-52). Thus "non-viral vector" can include vectors composed of nucleic acid plus viral particles where the viral particles do not contain the DNA of interest within the viral genome.

In one embodiment, the formulation comprises viral particles which are mixed with the naked DNA construct prior to administration. About $10^8$ to about $10^{10}$ viral particles (preferably about $1\times10^{10}$ to about $5\times10^{10}$, more preferably about $3\times10^{10}$ particles) are mixed with the naked DNA construct (about 5 μg to 50 μg DNA, more preferably about 81 g to 25 μg DNA) in a total volume of about 100 μl. Preferably the viral particles are adenovirus particles (Curiel et al., 1992 supra).

Alternatively or in addition, the nucleic acid can be complexed with polycationic substances such as poly-L-lysine or DEAC-dextran, targeting ligands, and/or DNA binding proteins (e.g., histones). DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-.beta.-ol 3-urethanyl)-N',N'-dimethylethylene diamine).

For example, the naked DNA can be administered in a solution containing Lipofectin™ (LTI/BRL) at a concentrations ranging from about 2.5% to 15% volume: volume, preferably about 6% to 12% volume:volume. Preferred methods and compositions for formulation of DNA for delivery according to the method of the invention are described in U.S. Pat. No. 5,527,928, the disclosure of which is incorporated herein by reference.

The nucleic acid of interest can also be administered as a chemical formulation of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids which allow coupling of the nucleic acid compounds to a carrier molecule such as a protein or lipid, or derivative thereof. Exemplary protein carrier molecules include antibodies specific to the cells of a targeted pancreatic cell or receptor ligands, e.g., molecules capable of interacting with receptors associated with a cell of a targeted pancreatic cell.

Production of Islet Transcription Factor Polypeptides and Antibodies that Specifically Bind Such Polypeptides Nucleic acid encoding Ngn3, NeuroD1, Mash1 or other islet transcription factors may be employed to synthesize full-length polypeptides or fragments thereof, particularly fragments corresponding to functional domains; DNA binding sites; etc.; and including fusions of the subject polypeptides to other proteins or parts thereof. Accordingly, the polynucleotides and polypeptides suitable for use in the invention include, without limitation, islet transcription factor polypeptides and polynucleotides found in primates, rodents, canines, felines, equines, nematodes, yeast and the like, and the natural and non-natural variants thereof.

The islet transcription factor polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of the polypeptide. Antibodies may be raised to isolated peptides corresponding to these domains, or to the native protein, e.g. by immunization with cells expressing the polypeptide of interest, immunization with liposomes having a polypeptide of interest inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. For further description, see Monoclonal Antibodies: A Laboratory Manual, Harlow and Lane eds., Cold Spring Harbor Laboratories, Cold Spring Harbor, N.Y., 1988.

Antibodies that specifically bind islet transcription factors can be utilized to detect cells expressing a recombinant islet transcription factor such as Ngn3, NeuroD1, or Mash1 (e.g., prior to transplantation or implantation, as described in more detail below).

Production of Islet Cells by Expression of Transcription Factor-Encoding Nucleic Acids Islet cells can be produced according to the invention in a variety of ways. In general, the invention involves stimulating the production of an islet transcription factor. In an embodiment of particular interest, the invention involves enhancing islet transcription factor activity by introducing a nucleic acid encoding an islet transcription factor into a cell, usually a pancreatic cell.

Production of Islet Cells In Vitro by Introduction of an Islet Transcription Factor-Encoding Nucleic Acid Nucleic acid encoding an islet transcription factor (e.g., Ngn3, NeuroD1, Mash1, and the like) can be introduced into a cell in vitro to accomplish expression in the cell to provide for at least transient expression. The cells into which the nucleic acid is introduced can be differentiated epithelial cells (e.g., pancreatic cells, gut cells, hepatic cells or duct cells), pluripotent adult or embryonic stem cells, or any mammalian cell capable of developing into β cells or cells capable of expression of insulin in vitro following expression of an islet transcription factor-encoding nucleic acid. The cell is subsequently implanted into a subject having an insulin-associated disorder, which disorder is amenable to treatment by islet cell replacement therapy (e.g., ex vivo therapy).

In one embodiment, the host cell in which islet transcription factor expression, preferably Ngn3, NeuroD1, or Mash1, and in particularNgn3 expression or expression of another positive regulator of the NgN3 regulatory pathway, is provided, and which is implanted in the subject is derived from the individual who will receive the transplant (e.g., to provide an autologous transplant). For example, in a subject having Type 1 diabetes, pluripotent stem cells, hepatic cells, gut cells or pancreatic cells can be isolated from the affected subject, the cells modified to express islet transcription factor-encoding DNA, and the cells implanted in the affected subject to provide for insulin production, or the transformed cells cultured so as to facilitate development of the cells into insulin-producing β-cells, followed by implantating of the β-cells into the affected subject.

In another embodiment, pluripotent stem cells, hepatic cells, gut cells or pancreatic cells from another subject (the "donor") are modified to express islet transcription factor-encoding DNA, particularly Ngn3-encoding DNA or DNA encoding another positive regulatory of the Ngn3 regulatory pathway, and the cells subsequently implanted in the affected subject to provide for insulin production (e.g., to provide a heterologous transplant), or the transformed cells cultured so as to facilitate development of the cells into insulin-producing β-cells, followed by implanting of the β-cells into the affected subject.

Introduction of nucleic acid into the cell in vitro can be accomplished according to methods well known in the art (e.g., through use of electroporation, microinjection, lipofection, infection with a recombinant (preferably replication-deficient) virus, and other means well known in the art). The nucleic acid is generally operably linked to a promoter that facilitates a desired level of polypeptide expression (e.g., a promoter derived from CMV, SV40, adenovirus, or a tissue-specific or cell type-specific promoter). Transformed cells containing the recombinant nucleic acid can be selected and/or enriched via, for example, expression of a selectable marker gene present in the introduced construct or that is present on a nucleic acid that is co-transfected with the construct. Typically selectable markers provide for resistance to antibiotics such as tetracycline, hygromycin, neomycin, and the like. Other markers can include thymidine kinase and the like. Other markers can include markers that can be used to identify expressing cells, such as beta-galactosidase or green fluorescent protein.

Expression of the introduced nucleic acid in the transformed cell can be assessed by various methods known in the art. For example, expression of the introduced gene can be examined by Northern blot to detect mRNA which hybridizes with a DNA probe derived from the relevant gene. Those cells that express the desired gene can be further isolated and expanded in in vitro culture using methods well known in the art. The host cells selected for transformation will vary with the purpose of the ex vivo therapy (e.g., insulin production), the site of implantation of the cells, and other factors that will vary with a variety of factors that will be appreciated by the ordinarily skilled artisan.

The transformed cell can also be examined for the development of an islet cell phenotype. For example, expression of insulin, IAPP, glucokinase, or somatostatin could be detected by PCR, northern blot, immunocytochemistry, western blot, RIA or ELISA. Alternatively a marker gene such as green fluorescent protein or an antibiotic resistance gene operatively linked to an islet specific promoter such as the insulin gene promoter could be used for identification or selection of differentiated islet cells. Methods for engineering a host cell for expression of a desired gene product(s) and implantation or transplantation of the engineered cells (e.g., ex vivo therapy) are known in the art (see, e.g., Gilbert et al. 1993 "Cell transplantation of genetically altered cells on biodegradable polymer scaffolds in syngeneic rats," Transplantation 56:423-427). For expression of a desired gene in exogenous or autologous cells and implantation of the cells (e.g., islet cells) into pancreas, see, e.g., Docherty 1997 "Gene therapy for diabetes mellitus," Clin Sci (Colch) 92:321-330; Hegre et al. 1976 "Transplantation of islet tissue in the rat," Acta Endocrinol Suppl (Copenh) 205:257-281; Sandler et al. 1997 "Assessment of insulin secretion in vitro from microencapsulated fetal porcine islet-like cell clusters and rat, mouse, and human pancreatic islets," Transplantation 63:1712-1718; Calafiore 1997 "Perspectives in pancreatic and islet cell transplantation for the therapy of IDDM," Diabetes Care 20:889-896; Kenyon et al. 1996 "Islet cell transplantation: beyond the paradigms," Diabetes Metab Rev 12:361-372; Sandler; Chick et al. 1977 Science "Artificial pancreas using living beta cells: effects on glucose homeostasis in diabetic rats," 197:780-782. In general, the cells can be implanted into the pancreas, or to any practical or convenient site, e.g., subcutaneous site, liver, peritoneum.

Methods for transplanting islets cells are well known in the art, see, e.g., Hegre et al. 1976 "Transplantation of islet tissue in the rat," Acta Endocrinol Suppl (Copenh) 205:257-281; Sandler et al. 1997 "Assessment of insulin secretion in vitro from microencapsulated fetal porcine islet-like cell clusters and rat, mouse, and human pancreatic islets," Transplantation 63:1712-1718; Calafiore 1997 "Perspectives in pancreatic and islet cell transplantation for the therapy of IDDM," Diabetes Care 20:889-896; Kenyon et al. 1996 "Islet cell transplantation: beyond the paradigms," Diabetes Metab Rev 12:361-372; Sandler; Chick et al. 1977 Science "Artificial pancreas using living beta cells: effects on glucose homeostasis in diabetic rats," 197:780-782.

In general, after expansion of the transformed cells in vitro, the cells are implanted into the mammalian subject by methods well known in the art. The number of cells implanted is a number of cells sufficient to provide for expression levels of insulin sufficient to lower blood glucose levels. The number of cells to be transplanted can be determined based upon such factors as the levels of polypeptide expression achieved in vitro, and/or the number of cells that survive implantation. The transformed cells are implanted in an area of dense vascularization such as the liver, and in a manner that minimizes surgical intervention in the subject. The engraftment of the implant of transformed cells is monitored by examining the mammalian subject for classic signs of graft rejection, i.e., inflammation and/or exfoliation at the site of implantation, and fever, and by monitoring blood glucose levels.

The transplantation method described above is not limited to the expression of nerougenin3. Engineering a host cell for expression of other islet transcription factors in the differentiation cascade, particularly NeuroD1 and Mash1, in conjunction with or in place of Ngn3, may also be used to treat subjects with insulin-associated disorders.

In Vivo Development of Islet Cells and Production of Insulin in the Pancreas

Islet transcription factor-encoding nucleic acid can be delivered directly to a subject to provide for islet transcription factor expression in a target cell (e.g., a pancreatic cell, gut cell, liver cell, or other organ cell capable of expressing an islet transcription factor and providing production of insulin), thereby promoting development of the cell into an insulin-producing cell (e.g., in pancreas) or to cure a defect in islet transcription factor expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, or pneumatic injection using a gene gun).

In general, the transformed cells expressing the protein encoded by the DNA of interest produce a therapeutically effective amount of the protein to produce islet cells, in particular β-cells in the mammalian patient. In one embodiment, the DNA of interest encodes an islet transcription factor such as Neurogeninl, Neurogenin2, Neurogenin3, NeuroD1/BETA2, Mash1 or NeuroD4/Math3 (with Ngn3 being of particular interest), and the DNA of interest is operably linked to a promoter, which may be heterologous or endogenous to the transcription factor. In a preferred embodiment, the DNA of interest encodes Ngn3, NeuroD1, or Mash1, and in particular Ngn3.

In general terms, the delivery method comprises introducing the DNA of interest-containing vector into a pancreatic cell. By way of example, DNA of interest-containing vector may comprise either a viral or non-viral vector (including naked DNA), which is introduced into the pancreas in vivo via the duct system. Intraductal administration can be accomplished by cannulation by, for example, insertion of the cannula through a lumen of the gastrointestinal tract, by insertion of the cannula through an external orifice, or insertion of the cannula through the common bile duct. Retrograde ductal administration may be accomplished in the pancreas by endoscopic retrograde chalangio-pancreatography (ECRP). Exemplary methods for accomplishing intraductal delivery to the pancreas are described in U.S. Pat. No. 6,004,944.

The precise amount of islet transcription factor-encoding nucleic acid administered will vary greatly according to a number of factors, including the susceptibility of the target cells to transformation, the size and weight of the subject, the levels of protein expression desired, and the insulin-associated disorder to be treated. The amount of nucleic acid and/or the number of infectious viral particles effective to infect the targeted tissue, transform a sufficient number of cells, and provide for production of a desired level of insulin can be readily determined based upon such factors as the efficiency of the transformation in vitro and the susceptibility of the targeted cells to transformation. For example, the amount of DNA introduced into the pancreatic duct of a human is, for example, generally from about 1 μg to about 750 mg, preferably from about 500 μg to about 500 mg, more preferably from about 10 mg to about 200 mg, most preferably about 100 mg. Generally, the amounts of introduced DNA can be extrapolated from the amounts of DNA effective for delivery and expression of the desired gene in an animal model. For example, the amount of DNA for delivery in a human is roughly about 100 times the amount of DNA effective in a rat.

Pancreatic cells modified according to the invention can facilitate sufficiently high levels of expression of a nucleic acid of interest, particularly where the nucleic acid delivered is DNA and the DNA of interest is operably linked to a strong eukaryotic promoter (e.g., CMV, MMTV). The expressed protein can induce islet cell and insulin production. Thus the methods of the invention are useful in treating a mammalian subject having a variety of insulin-associated disorders.

In one embodiment, the encoded proteins are islet transcription factors from the class of basic helix-loop-helix (bHLH) proteins. For example, the expression of neurogenin3 and/or NeuroD1 and/or Mash1 may substantially induce the production of islet cells and insulin in mammals.

The actual number of transformed pancreatic cells required to achieve therapeutic levels of the protein of interest will vary according to several factors including the protein to be expressed, the level of expression of the protein by the transformed cells, the rate in which the protein induces islet cell production (in particular Beta cells), and the condition to be treated.

Regardless of whether the islet transcription factor-encoding nucleic acid is introduced in vivo or ex vivo, the nucleic acid (or islet cells produced in vitro or recombinant cells expressing the islet transcription factor nucleic acid that are to be transplanted for development into islet cells in vivo post-transplantation) can be administered in combination with other genes and other agents.

Assessment of Therapy

The effects of ex vivo or in vivo therapy according to the methods of the invention can be monitored in a variety of ways. Generally, a sample of blood from the subject can be assayed for, for example, levels of glucose, proinsulin, c-peptide, and insulin. Appropriate assays for detecting proinsulin, c-peptide, insulin and glucose in blood samples are well known in the art. Evidence for recurrent autoimmunity can be gauged by assaying for autoreactive T cells or for antibodies against islet proteins such as glutamic acid decarboxylase (GAD), or other autoantigens well known in the art.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Detection of Ngn3 Expression in Murine Pancreas

Members of the basic helix-loop-helix (bHLH) family of transcription factors regulate growth and differentiation of numerous cell types. Insulin gene expression is activated by a heterodimeric complex of two bHLH proteins: a ubiquitously expressed (class A) protein and a cell-type-specific (class B) partner, NeuroD1/BETA2. NeuroD1/BETA2 is also important for β-cell development. The targeted disruption of the NeuroD1/BETA2 gene in mice leads to a marked reduction of the β-cell mass at birth due to increased apoptosis of islet cells late in fetal development. There is no apparent defect, however, in β-cell formation or insulin gene expression, despite the postulated importance of this factor in β-cell differentiation.

Assuming that this modest phenotype reflected the redundant expression of closely related class B bHLH proteins in the endocrine pancreas, the inventors searched for additional members of the family by reverse transcriptase-polymerase chain reaction (RT-PCR) using degenerate oligonucleotides primers based on conserved amino acid sequences in the bHLH domain of the class B bHLH proteins (Sommer et al. 1996 Mol. Cell. Neurosci. 8:221). PCR analysis revealed that pancreatic endocrine cell lines and isolated adult islet cells not only express NeuroD1, but also several other members of the family of neural class B bHLH genes as well, including Mash1, neuroD2 and 4 and neurogenins (ngn) 1, 2 and 3. This remarkable degree of redundancy could compensate for the loss of NeuroD1/BETA2 in mice. The two most commonly amplified sequences encoded NeuroD4 and Ngn3, but in situ hybridization studies in mouse pancreas showed highest expression of NeuroD1 and Ngn3. These results were confirmed by immunohistochemistry.

Ngn3 is detected earliest at embryonic day 11.5 (e11.5) in the mouse, increases to a maximum at e15.5 and decreases at e18.5, with no staining seen in the adult pancreas. Ngn3 is detected in the nuclei of scattered ductal cells and periductal cells, and there was no co-staining with any of the four islet hormones (insulin, glucagon, somatostatin and pancreatic polypeptide). This temporal and spatial pattern of expression implicated Ngn3 as a marker for islet cell precursors. Nkx6.1, a specific marker for future beta-cells, was expressed in 10-20% of the Ngn3 positive cells, further supporting the use of Ngn3 as a marker for islet cell precursors. The peak of Ngn3 expression at e15.5 also corresponds with the peak of new beta-cell formation in the fetus. Our data supports a model in which Ngn3 acts upstream of NeuroD1/BETA2 and other islet differentiation factors, marking islet cell precursors, but switching off prior to final differentiation.

Example 2

Isolation and Seouencing of a Human Ngn3 Polypeptide-Encoding Polynucleotide A probe derived from a cloned fragment of the murine Ngn3 gene (Sommer et al., supra) was used to screen a human genomic library. This screen resulted in the isolation of the genomic sequence provided as SEQ ID NO:1 in the sequence listing. Based on mapping of the murine start site using 5' RACE of mouse fetal pancreatic RNA, the transcriptional start site in the human Ngn3-encoding sequence is at nucleotide residue 2643. The coding sequence is between nucleotide residues 3022-3663, with a stop site at 3664-3666. No introns are within the 5' untranslated region (UTR) or the coding sequence of SEQ ID NO:1.

The promoter of Ngn3 is of interest, particularly given that is it exceptionally well-conserved between mouse, rat, and human. Given the role of Ngn3 in pancreatic and islet cell development, the Ngn3 promoter is likely key to determining the number of islet cells in the mature pancreas. The regulatory region corresponding to the human Ngn3 promoter comprises sequences up to approximately 500 bp upstream of the transcription start site within the human Ngn3 promoter (e.g., from about 2144 to the transcriptional start site at 2643). FISH was used to identify the location of Ngn3 on the human chromosome at 10q22.1-22.2.

Example 3

Isolation and Sequencing of a Murine Ngn3 Polypeptide-Encoding Polynucleotide and Promoter The full-length murine Ngn3 sequence and its 5' flanking sequences, which included the murine Ngn3 promoter, were obtained by sequencing a previously obtained mouse genomic DNA fragment (Sommer, et al., supra). The murine Ngn3 sequence is provided in the Sequence Listing as SEQ ID NO:3, with the encoded polypeptide provided as SEQ ID NO:4. The transcriptional start site was determined using the 5' RACE method and confirmed using RNase protection with RNA from fetal mouse pancreas, and is at nucleotide residue 719; the coding sequence for murine Ngn3 begins at nucleotide residue 1093. The promoter comprises a region approximately 500 bp upstream of the transcription start site.

Example 4

Construction of Adenovirus Vector Encoding Neurogenin3

The full length mouse neurogenin3 coding sequence was inserted downstream of the cytomegalovirus immediate early gene promoter (PCMV IE) in the Adeno-X viral genome, and intact viral particles were produced as per the instructions of the manufacturer (Clontech, Palo Alto, Calif.) for the Adeno-X™ Expression System. FIG. 1 provides a map of the final Adeno-X.NGN3 construct. A control construct was produced using a lac Z coding sequence in lieu of Ngn3 to produce an Adeno.LacZ construct. Large scale preparation of adenovirus for the experiments below was performed using protocols well known in the art. Virus concentration was estimated based on the protein concentration of the purified virus stock, not by plaque assay. Identity of the virus was confirmed by PCR during preparation, and by Western blot for neurogenin3 using lysates from cells infected with the purified stock.

Example 5

Induction of Insulin in Normal Adult Rats by Treatment with Adeno-X.NGN3

Adult male Sprague-Dawley rats weighing 250-350 g were injected with either Adeno.LacZ or Adeno-X.NGN3 into the pancreatic duct using the previously described surgical technique, (Goldfine et al. Nat Biotechnol 15:1378-82, 1997). Approximately, 3×1010 viral particles (low dose) or high dose, 3×1011 (high dose were injected into the pancreatic duct of each animal. After recovery from the surgery, the animals were returned to a normal diet. After approximately 48 hours, the animals subjected to the low dosage of Adeno-X.NGN3 were sacrificed, the pancreases were removed, fixed, embedded in paraffin and sectioned. The pancreatic sections were stained for insulin, glucagon, cytokeratin20 (a marker for ducts), and mouse neurogenin3 using established immunohistochemical techniques and antisera (Schwitzgebel et al. *Development* 127:3533-3542, 2000.).

Figure 2A:
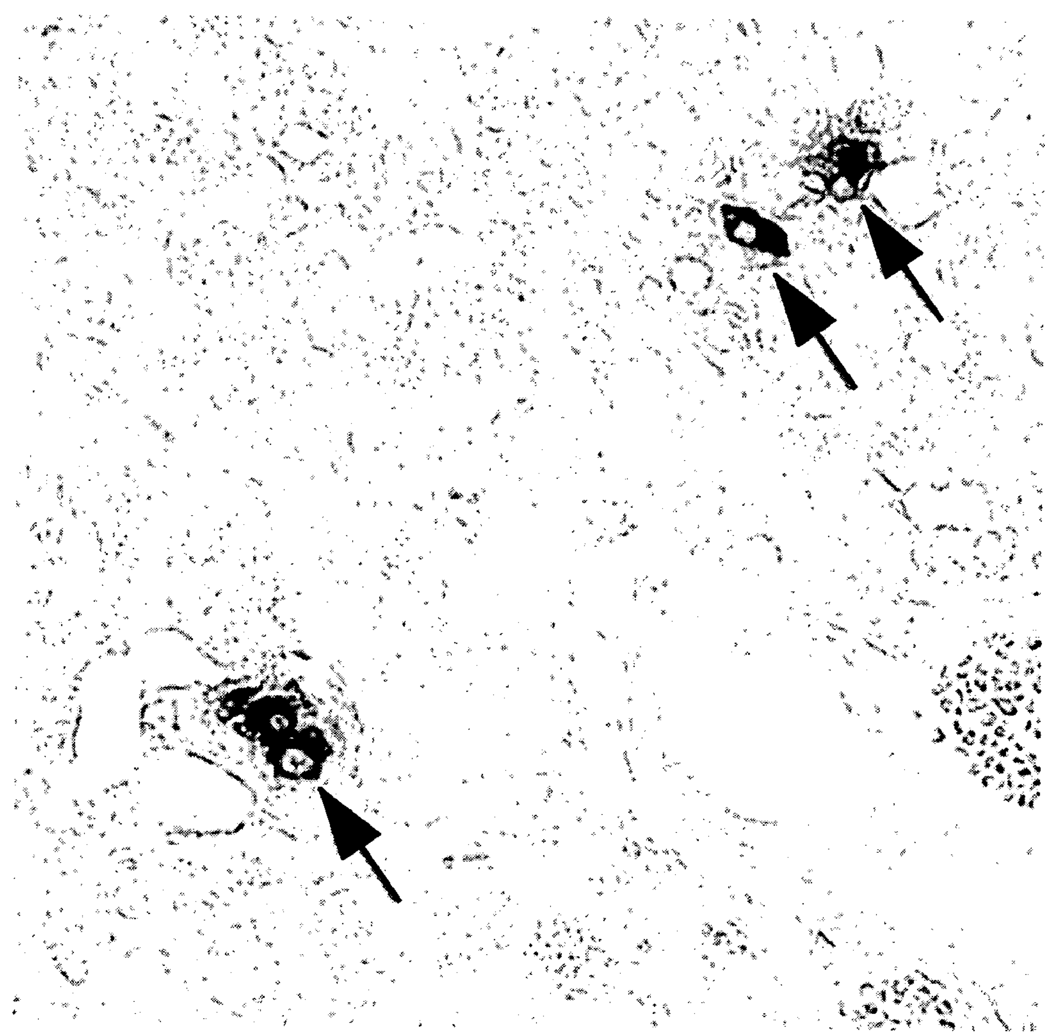
FIG. 2A is a photograph showing histological staining for insulin in a pancreatic tissue section of an animal injected with Adeno-X.NGN3 at high magnification (40×) which indicates the production of insulin in accordance with the invention. The arrows indicate insulin staining cells.
Figure 2B:
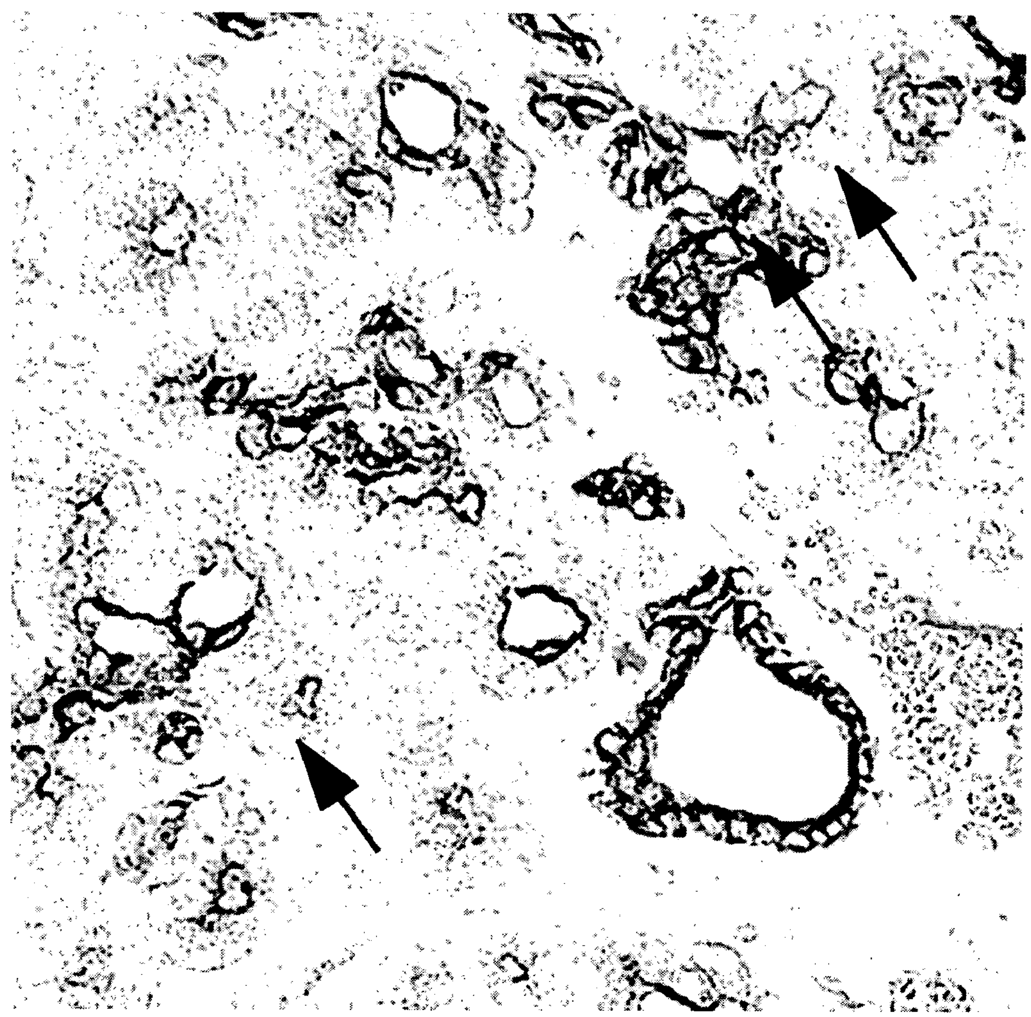
FIG. 2B is a photograph of a serial section of FIG. 2A, stained for the duct cell marker cytokeratin20. The arrows indicate the position of insulin staining cells in the serial sections.

Animals injected with the low or high dose of Adeno-X.NGN3 had individual or small clumps of 8 or fewer insulin or glucagon staining cells found scattered near the ducts, in addition to the normal large (approximately 1000 cells) aggregations of glucagon and insulin staining cells that form the islets of Langerhans. FIG. 2A shows the results of histological staining for insulin in a pancreatic tissue section of an animal injected with low dose (3×1010) Adeno-X.NGN3. Individual and small clumps of insulin staining cells are indicated with arrows. FIG. 2B shows a serial section from the same animal stained for the duct cell marker cytokeratin 20, with the arrows indicating the position of the insulin staining in FIG. 2A.

Animals injected with the control Adeno.LacZ virus had no scattered insulin or glucagon staining cells outside of the islets of Langerhans. All of the animals injected with high titer of the neurogenin3 expressing adenovirus died within 36 hours after injection. One of the high dose animals before death had a blood glucose level of 32 mg/ml measured by the glucose oxidase method using the Glucometer Elite meter (Bayer Corporation, Elkhart, Ind.). The blood glucose level for fasted rat is normally approximately 100 mg/dl and rarely seen below 70 mg/dl. The blood glucose level of 32 mg/ml for the high dose animal indicates that excess insulin was being produced to lower the blood glucose to hypoglycemic levels. The animals injected with the high dose of DNA encoding Ngn3 appeared to have died from hypoglycemia induced by the overexpression of insulin from the newly produced β cells.

Figure 3:
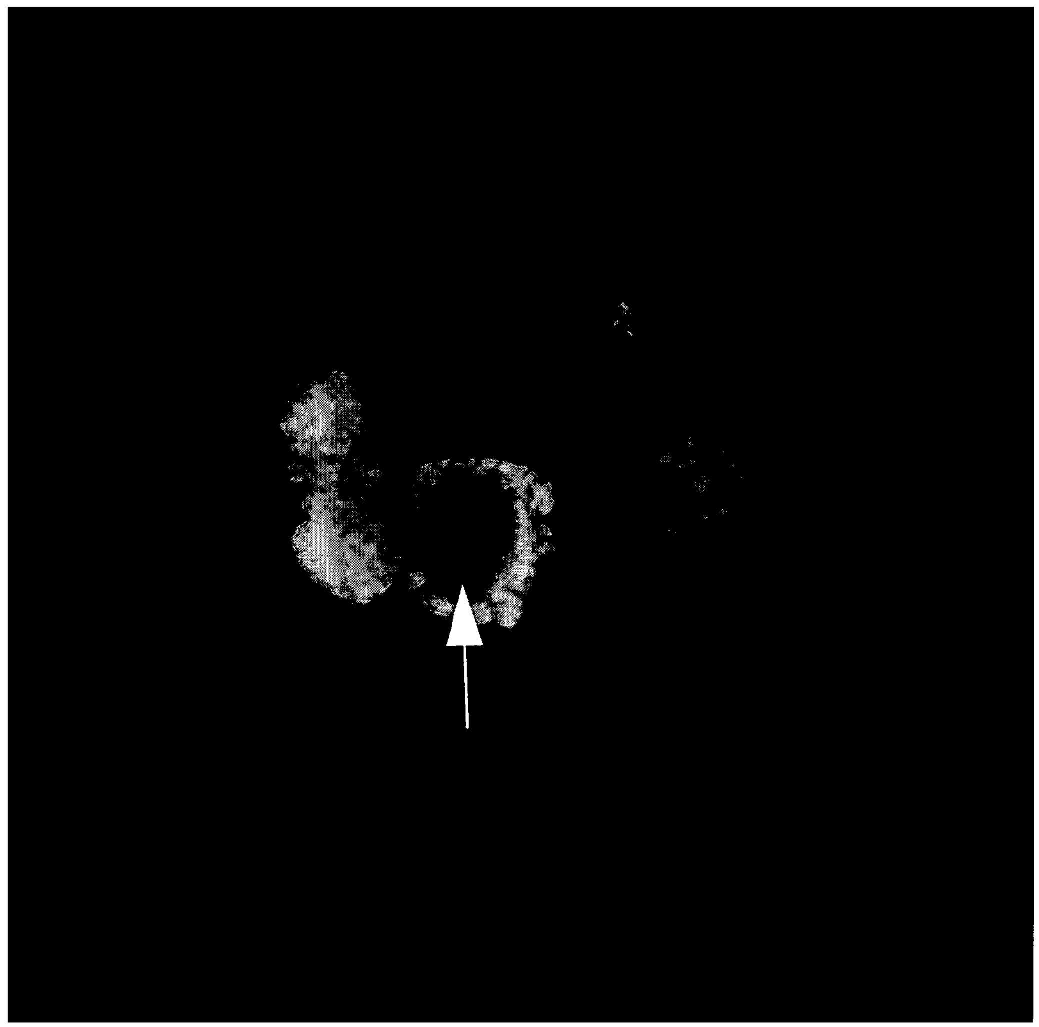
FIG. 3 is a photograph of a confocal image with fluorescent co-staining for insulin and neurogenin3 in the pancreas of an animal injected with Adeno-XZ.NGN3. It can be seen that the cell in the center of the figure stains for neurogenin3 in the nucleus (dark gray area indicated by arrow) and insulin in the cytoplasm (light gray surrounding area). The production of neurogenin3 and insulin can be detected in the same cell in accordance with the invention.

FIG. 3 shows a confocal image with fluorescent co-staining for insulin and neurogenin3 in the pancreas of an animal infected with high dose ($3\times10^{11}$) Adeno-X.NGN3 and harvested at approximately 24 hours. It can be seen that the cell in the center of the figure stains for neurogenin3 in the nucleus (dark gray area indicated by arrow) and insulin in the cytoplasm (light gray surrounding area). No neurogenin3 could be detected in the pancreases of the control animals.

Example 6

Normalization of Blood Glucose Levels in Diabetic Induced Adult Rats Induced by the Introduction of DNA Encoding Murine Ngn3 into the Pancreas Diabetes was induced in adult male Sprague-Dawley rats weighing 250-350 g by injection with the beta-cell toxin of streptozotocin (Sigma: 40 mg/kg of body weight, in 1 mM citrate buffer, pH 4.5) into the peritoneal space on day 1 and day 2. Streptozotocin is a β-cell toxin which induces diabetes mellitus in rats. On day 4, animals that were confirmed to have hyperglycemia (blood glucose greater than 300 mg/dl measured by the glucose oxidase method using the Glucometer Elite meter (Bayer Corporation, Elkhart, Ind.)) were injected with either Adeno.LacZ or Adeno-X.NGN3 into the pancreatic duct using the previously described surgical technique. Approximately, 3×1010 or 3×1011 viral particles were injected into the pancreatic duct of each animal.

Figure 4A:
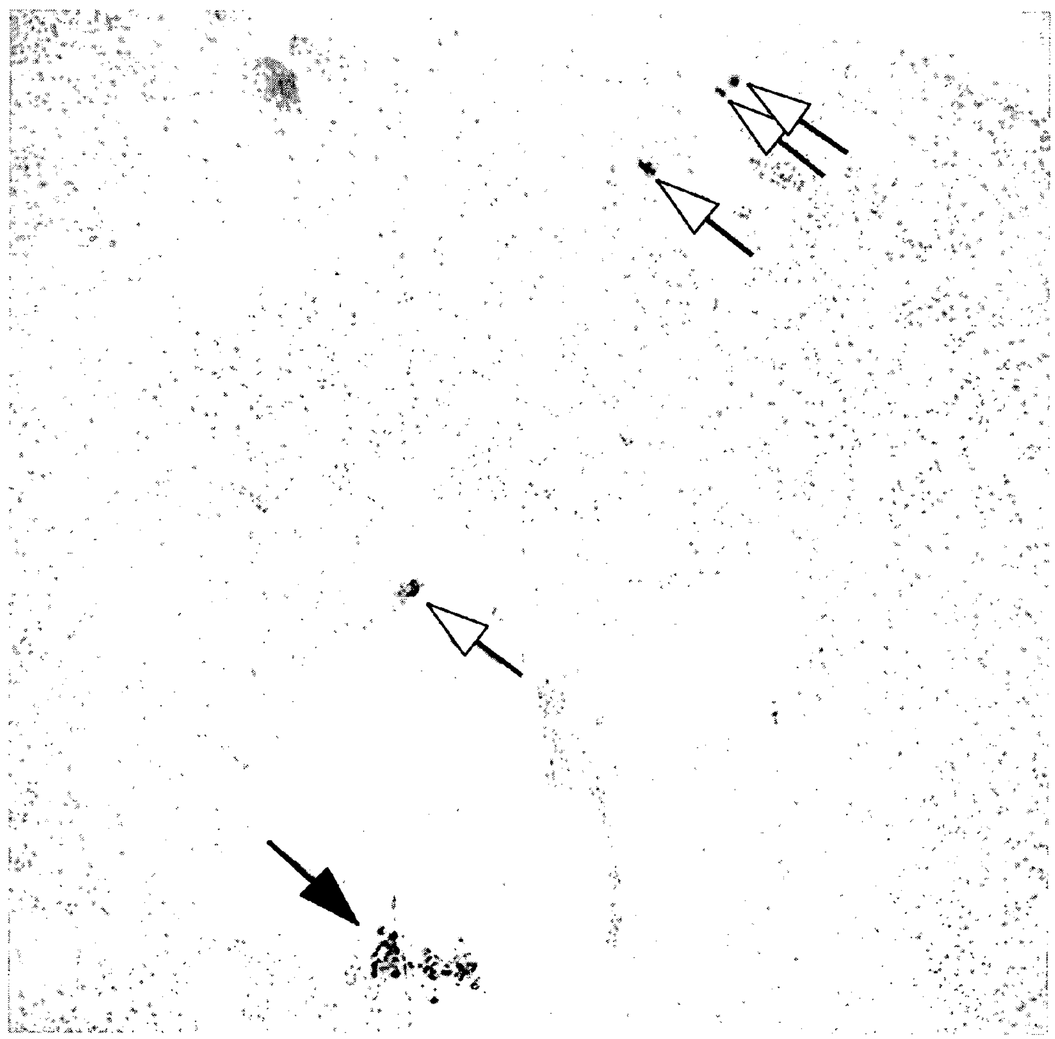
FIG. 4A is a photograph showing histological staining for insulin in a pancreatic tissue section of an animal made diabetic with streptozotocin and injected with Adeno-X.NGN3 indicating the production of insulin producing cells in accordance with the present invention. White arrows indicate individual and small clusters of insulin staining cells. Black arrow indicates residual and degenerating cells remaining in formed islets after streptozotocin treatment.

Five days after surgery, the animals were sacrificed, the pancreases were removed, fixed, embedded in paraffin and sectioned. The pancreatic sections were stained for insulin, glucagon, cytokeratin 20 (a marker for ducts), and mouse neurogenin3. FIG. 4A shows the results of histological staining for insulin in a pancreatic tissue section of an animal injected with Adeno-X.NGN3 which indicates the production of insulin in accordance of the invention. Individual and small clumps of insulin staining cells are indicated with white arrows. An islet with a few residual insulin staining cells (the remainder having been destroyed by streptozotocin) is indicated with a black arrow.

Figure 4B:
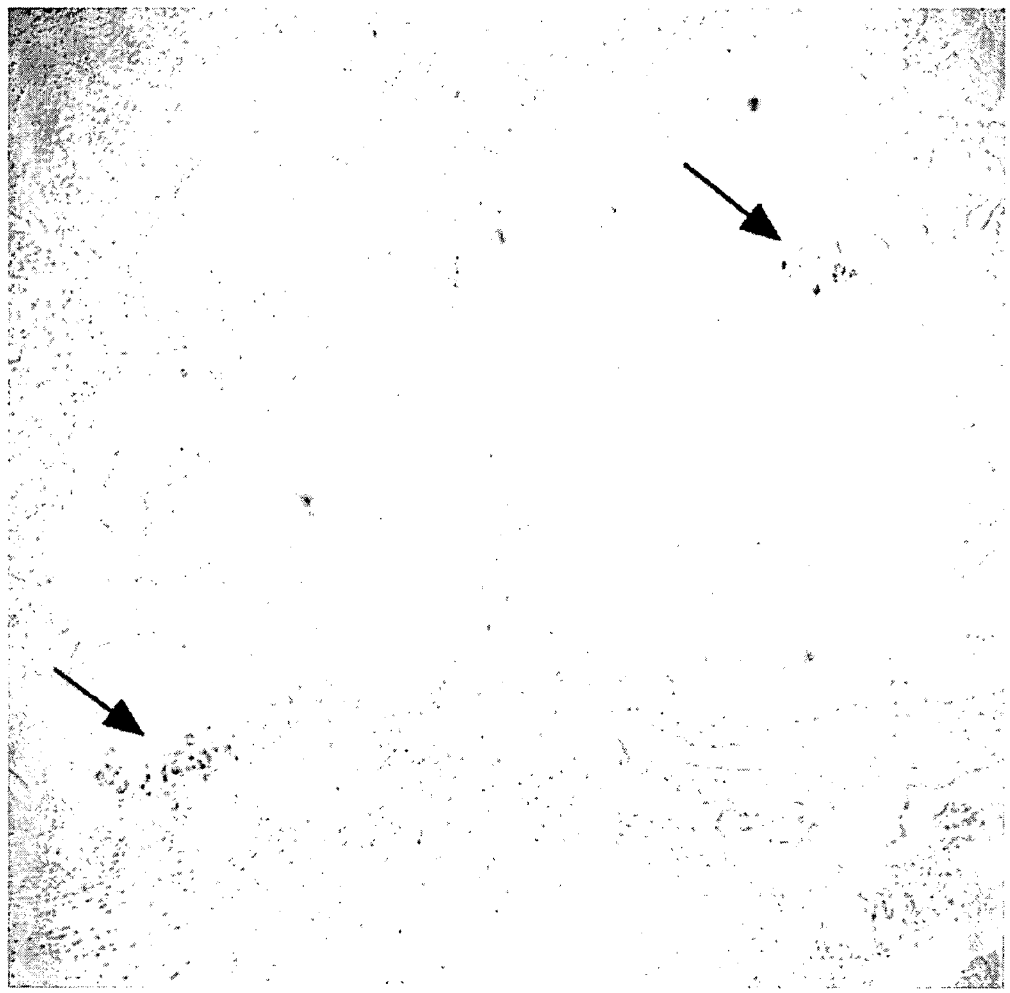
FIG. 4B is a photograph showing staining for insulin in a pancreatic tissue section of an animal injected with Adeno-.LacZ, a control viral construct. Arrows indicate residual and degenerating cells remaining in formed islets after streptozotocin treatment. Note individual and small clusters of insulin staining cells are seen.

FIG. 4B shows the results of staining for insulin in the pancreas of an animal injected with Adeno-LacZ virus. Two islets with a few residual insulin staining cells are indicated with arrows. No individual or small clumps of insulin staining cells were detected in the control animals.

Figure 5:
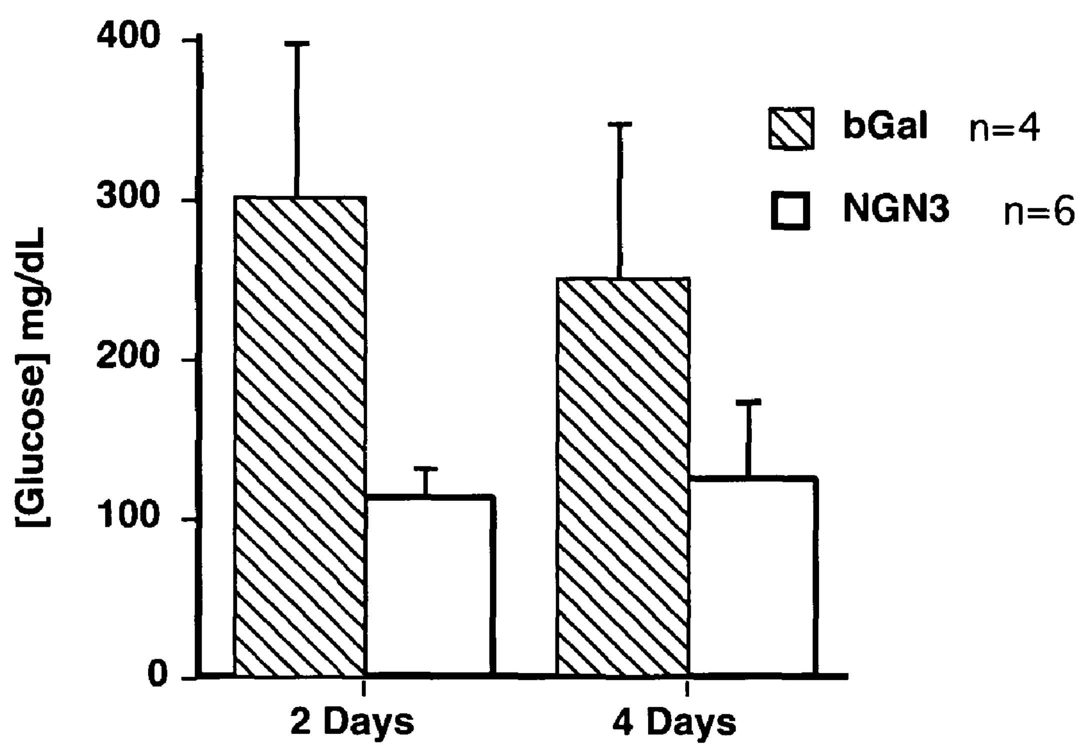
FIG. 5 is a graphical illustration of blood glucose levels of streptozotocin-treated animals (diabetic) that received either AdenoX-.NGN3 or Adeno.LacZ (control animals).

The animals injected with the Adeno-X.NGN3 virus had significantly lower blood glucose levels than the control animals injected with Adeno.LacZ. As shown in FIG. 5, blood glucose levels were significantly decreased in the diabetic rats that received AdenoX-.NGN3 relative to the diabetic rats that received Adeno.LacZ. The decreased blood glucose levels were observed on both day 2 and day 4. Thus, these data show that introduction of Ngn3-encoding DNA into the pancreas results in persistent expression of insulin, and that the insulin expressed by the transformed pancreatic cells is secreted into the bloodstream and can function in regulation of blood glucose at levels sufficient to overcome diabetes in an animal model.

The present invention demonstrates that cells in the mature pancreas, most likely duct cells, retain the capacity to differentiate into endocrine cells. Adult duct cells respond to proendocrine bHLH genes, and in particular, Ngn3, and in combination with other signals these genes can induce new beta cell formation and subsequent insulin production. The present invention will be useful in the maintenance and treatment of type 2 diabetes and also allow for the replacement of beta cells lost to autoimmune destruction in individuals with type 1 diabetes.

Example 7

Overexpression of Ngn3 and Islet Cell Production in Ngn3 Transgenic Animals

As previously described (Schwitzgebel et al. Development 127:3533-3542, 2000), the pdxl promoter vector pBAT.PD17 was constructed by inserting the mouse pdxl promoter (a 4.4 kb XbaI-Sma I fragment from the mouse Pdxl gene containing the transcription start site and promoter (Apelqvist et al. *Curr Biol* 7:801-804; Wu et al. *Mol Cell Biol* 17:6002-6013 (1997)), and the human beta-globin gene first intron upstream of the pBAT polylinker (German et al. Genes & Dev 6:2165-2176), and the SV40 late gene polyadenylation signal. A 663 bp DNA fragment encoding full length mouse Ngn3 cDNA was obtained by PCR from the mouse genomic neurogenin3 clone (Sommer et al. Mol Cell Neurosci 8:221-241 (1996)) and inserted into the pBAT.PD17 polylinker.

The vectors were linearized and purified, and transgenic mice were generated by pronuclear injection (1.5 ng/μl) into F1 hybrid oocytes from C3Fe/B6 parents (Hogan et al. (1994) Manipulating the mouse embryo: A Laboratory Manual. New York: Cold Spring Harbour Laboratory Press.). Genotypes were determined by PCR analysis of genomic DNA from tail biopsies. The primers used were: 5' TGGAGAACTGTCAAAGCGATCTG (SEQ ID NO:5) (Pdxl-primer for 5') and 5' CACATGCCCAGTTTCTATTGGTC (SEQ ID NO:6) (human beta-globin intron for 3').

Embryos were harvested at embryonic day 12.5 (E12.5) or E18.5. A total of 6 pdxl-ngn3 animals were examined at E12.5, and 10 were examined at E18.5. The transgenic embryos were not grossly abnormal in size. Transgenic embryos harvested at E12.5 have an increase in the numbers of islet cells as indicated in FIG. 7 by staining for glucagon. The control, non-transgenic embryos have normal numbers of glucagon expressing cells (FIG. 6). At E18.5, the pancreas size is grossly reduced in the transgenic animals, but the fraction of islet cells is markedly increased relative to the same age control animals.

These experiments demonstrate that neurogenin3 is capable of inducing islet cell neogenesis in appropriate progenitor cells.

Example 8

Islet Cell Production in NeuroD1 Transgenic Animals

The neuroD1/BETA2 vector was constructed by cloning into pBAT.PD17 a 1.7 Kb DNA fragment encoding the full length mouse cDNA (Lee et al. (1995) Science 268:836-844) extending from the start codon through the 3' UTR.

The vectors were linearized and purified, and transgenic mice were generated by pronuclear injection (1.5 ng/μl) into F1 hybrid oocytes from C3Fe/B6 parents as described (Hogan et al. (1994), supra). Genotypes were determined by PCR analysis of genomic DNA from tail biopsies. The primers used were: 5' TGGAGAACTGTCAAAGCGATCTG (SEQ ID NO:5) (Pdxl-primer for 5') and 5' CACATGCCCAGTTTCTATTGGTC (SEQ ID NO:6) (human beta-globin intron for 3').

Embryos were harvested at embryonic day 12.5 (E12.5) or E18.5. A total of 5 pdxl-neuroD1 animals were examined at E12.5, and 10 at E18.5. Similar to the neurogenin3 transgenic animals, the pdxl-neuroD1 transgenic embryos harvested at E12.5 have an increase in the numbers of islet cells as indicated in FIG. 8 by staining for glucagon. At E18.5, the pancreas size is grossly reduced in the transgenic animals, but the fraction of islet cells is markedly increased relative to the same age control animals.

These experiments demonstrate that like neurogenin3, neuroD1 is capable of inducing islet cell neogenesis in appropriate progenitor cells.

Example 9

Construction of Adenovirus Vector Encoding NeuroD1

The full-length mouse or human neuroD1 coding sequence is inserted downstream of the cytomegalovirus immediate early gene promote (PCMV IE) in the adenoviral genome, and intact viral particle produced according to methods well known in the art, for example as per the instructions of the manufacturer (Clontech, Palo Alto, Calif.), for the Adeno-X™ Expression System. FIG. 9 provides a map of such an exemplary Adeno-NeuroD1 construct.

Example 10

Construction of Adenovirus Vector Encoding Mash1/ASCL1/ASH1

The full length mouse mash1 or human ACSL1/ASH1 (human symbols for mas1) coding sequence are inserted downstream of the CMV immediate early gene promoter (PCMV IE) in the adenoviral genome, and intact viral particle produced according to methods well known in the art, for example as per the instructions of the manufacturer (Clontech, Palo Alto, Calif.), for the Adeno-X™ Expression System. FIG. 9 is a map of such an exemplary Adeno-mash1/ASCL1/ASH1 construct.

Example 11

Induction of the Formation of Insulin-Producing Beta-Cells in Normal Adult Rats by Treatment with Adeno-NeuroD1

Adult male Sprague-Dawley rats weighing 250-350 g are injected with either Adeno.LacZ or Adeno-neuroD1 (mouse or human) into the pancreatic duct using previously described surgical techniques (see, e.g., Goldfine, et al. *Nat. Biotechnol* 15:1378-82 (1997)). Approximately 3×1010 viral particles (low dose) or 3×1011 (high dose) are injected into the pancreatic duct of each animal. After recovery from the surgery, the animals are returned to normal diet. After approximately 48 hours, the animals are sacrificed, the pancreases removed, fixed, embedded in paraffin, and sectioned. The pancreatic sections are stained for insulin, glucagons, cytokerratin20 (a marker for ducts), and neuroD1 using established immunohistochemical techniques and antisera (Schwitzgebel, et al. *Development* 127:3533-3542, 2000).

Example 12

Induction of the Formation of Insulin-Producing Beta-Cells in Normal Adult Rats by Treatment with Adeno-Mash1/ASCL1/ASH1

Adult male Sprague-Dawley rats weighing 250-350 g are injected with either Adeno.LacZ or Adeno-mash1/ASCL1/ASH1 (mouse or human) into the pancreatic duct using previously described surgical techniques (see, e.g., Goldfine, et al. *Nat. Biotechnol* 15:1378-82 (1997)). Approximately 3×1010 viral particles (low dose) or 3×1011 (high dose) are injected into the pancreatic duct of each animal. After recovery from the surgery, the animals are returned to normal diet. After approximately 48 hours, the animals are sacrificed, the pancreases removed, fixed, embedded in paraffin, and sectioned. The pancreatic sections are stained for insulin, glucagons, cytokerratin20 (a marker for ducts), and neuroD1 using established immunohistochemical techniques and antisera (Schwitzgebel, et al. *Development* 127:3533-3542, 2000).

Example 13

Production of Insulin in Diabetic Induced Adult Rats by the Introduction of DNA Encoding NeuroD1 into the Pancreas Diabetes is induced in adult male Sprague-Dawley rats weighing 250-350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.)) are injected with either Adeno-LacZ or Adeno-NEUROD 1 (mouse or human) into the pancreatic duct using the previously described surgical technique. Approximately $3\times10^{10}$ or $3\times10^{11}$ viral particles are injected into the pancreatic duct of each animal. Animals would then be monitored every 12 hours for a fall in blood glucose levels.

Example 14

Production of Insulin in Diabetic Induced Adult Rats by the Introduction of DNA Encoding Mash1/ASCL1/ASH1 into the Pancreas Diabetes is induced in adult male Sprague-Dawley rats weighing 250-350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.)) are injected with either Adeno-LacZ or Adeno-mash1/ASCL1/ASH1 (mouse or human) into the pancreatic duct using the previously described surgical technique. Approximately $3\times10^{10}$ or $3\times10^{11}$ viral particles are injected into the pancreatic duct of each animal. Animals would then be monitored every 12 hours for a fall in blood glucose levels.

Example 15

Construction of Plasmid Vector Encoding Neurogenin3

Figure 10:
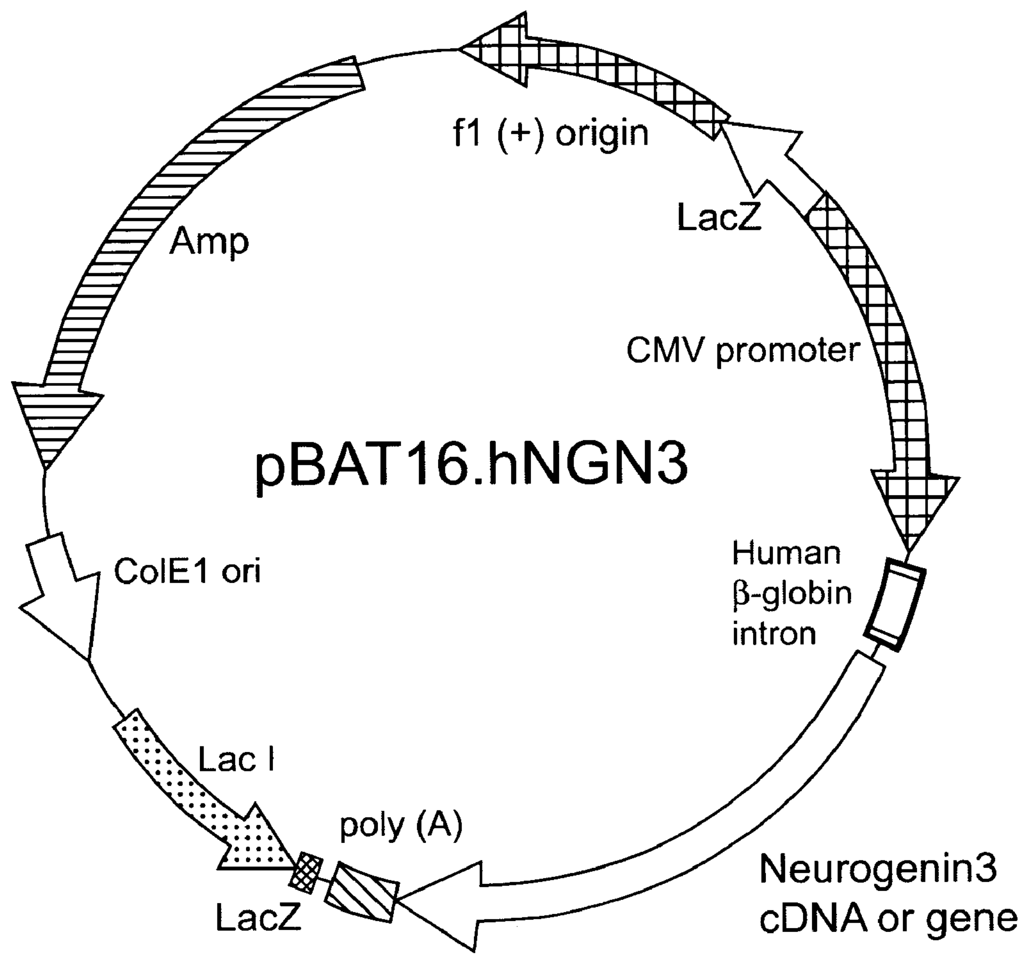
FIG. 10 is a map of the pBAT16.NGN3 plasmid DNA construct, which contains the neurogenein3 sequence operably linked to the CMV promoter.

The full length mouse or human neurogenin3 coding sequence, either cDNA or gene is inserted downstream of the CMV immediate early gene promoter (PCMV IE) and the human beta-globin gene intron, and upstream of the SV40 polyadenylation signal in the pBAT16 plasmid vector, which also contains the colE1 origin of replication for high copy number replication in bacteria, and the bacterial ampicillin resistance gene for selection of plasmid-containing bacteria. Purified plasmid DNA is produced according to methods well known in the art. FIG. 10 provides a map of such an exemplary pBAT16.hNGN3 construct.

Example 16

Production of Insulin in Diabetic Induced Adult Rats by the Introduction of Plasmid DNA Vector pBAT16.hNgn3 into the Pancreas Diabetes is induced in adult male Sprague-Dawley rats weighing 250-350 g by injection with the beta-cell toxin streptozotocin (Sigma: 40 mg/kg of body weight, in 1 mM citrate buffer, pH 4.5) into the peritoneal space on day 1 and day 2. Streptozotocin is a beta-cell toxin which induces diabetes mellitus in rats. On day 4, animals confirmed to have hyperglycemia (blood glucose greater than 300 mg/dl measured by the glucose oxidase method using the Glucometer Elite meter (Bayer Corporation, Elkhart, Ind.)) are injected with 8-25 μg of the plasmid DNA into a lumen of the pancreatic duct with or without adjuvant such as the cationic lipid reagent Transfast (Promega). The ability of naked DNA, with or without adjuvants such as cationic lipids, to express genes in pancreatic cells when injected into the pancreatic duct has been described previously (Goldfine et al. 1997, supra). Animals are then monitored every 12 hours for a fall in blood glucose levels.

Example 17

Production of Insulin in Mice with Autoimmune Diabetes by the Introduction of AdenoX-Ngn30R Plasmid DNA Vector pBAT16.hNgn3 into the Pancreas The NOD mouse develops a form of autoimmune diabetes that is an accepted model for human autoimmune, or "type 1" diabetes mellitus (for a review, see, e.g., Bach et al. The NOD mouse. Research in Immunology, 1997 June, 148(5):285-6). These animals have been used as a model for testing in an autoimmune setting treatment for diabetes, such as islet transplantation (for reviews see, e.g., Hahn et al. Adv. Exp. Med Biol. 1997 426:411-9; Sutherland Transplantation Proc. 1996, 28(4):2131-3).

In this example, adult mice greater than 15 weeks of age are tested for diabetes (blood glucose greater than 300 mg/dl measured by the glucose oxidase method using the Glucometer Elite meter (Bayer Corporation, Elkhart, Ind.)) and then are injected with either Adeno-LacZ or AdenoX-NGN3 (mouse or human), or plasmid vector pBAT16.hNGN3 into the pancreatic duct using the previously described surgical technique. Approximately 3×109 or 3×1010 viral particles are injected into the pancreatic duct of each animal, or 2-25 μg of plasmid DNA. Animals are then monitored every 12 hours for a fall in blood glucose levels.

To prevent recurrence of autoimmunity and destruction of the newly formed beta-cells, several methods are well known in the art, including, but not limited to, the use of drugs that suppress the immune system, such as cytoxan or FK506, or reagents that block co-stimulatory molecules such as antibodies to CTLA-4 (Shapiro et al. *New Engl. J. Med.* 2000 343 (4):230-8; Griffin et al. *J. Immunol,* 2000 164(9):4433-42). Animals are treated with the anti-autoimmune therapy starting 2 days prior to DNA injection, and maintained on the immunotherapy throughout the experiment.

Example 18

Induction of the Formation of Islet Cell In Vitro

In this example, neurogenin3 is used to induce islet cell formation from non-islet cells cultured in vitro. The cells used can include, but would not necessarily be limited to, immortalised mammalian cell lines, or primary cultured mammalian cells including cells from the gastrointestinal organs such as pancreatic duct cells, pancreatic acinar cells, gut cells including crypt cells, liver cells, and salivary gland cells; adult stem cells such as hematopoietic stem cells, neural stem cells, muscle stem cells, or pancreatic stem cells or embryonic stem cells. Cells are cultured using methods well known in the art. Neurogenin3 is introduced by viral vector (such as with the AdenoXZ-NGN3 vector) or naked DNA using a DNA plasmid vector such as pBAT16.hNGN3 along with adjuvant such as the cationic lipid transfection reagent Transfast. Cells are continued in culture for a period ranging from one day to several weeks. Detection of newly formed islet cells is performed by measuring for islet hormones such as insulin or glucagons with radio immune assays or ELISA in an extract made from a sample of the cells, or by measuring hormone levels in the culture media using methods well known in the art.

Example 19

Delivery of Ngn3-Encoding Nucleic Acid to a Human Subject

In this example, patients with diabetes mellitus or a relative deficiency of insulin are treated with neurogenin3 encoding DNA with the purpose of inducing new islet cell formation. The neurogenin3 encoding DNA can be contained in a viral vector, as in the AdenoX-NGN3 example above, or in a naked DNA vector, as in the pBAT16.NGN3 example above with or without an adjuvant such as the cationic lipid Transfast. The vector is introduced into the pancreas retrograde through the pancreatic duct. Where the vector is an adenovirus, the amount injected is determined by the amount needed to lower the blood glucose and maintain it in a normal range, which may be approximately about 1011 to about 1014 viral particles. Where the vector is a naked DNA vector, the amount required may be from about 100 μg to 100 mg of DNA.

To prevent recurrence of autoimmunity and destruction of the newly formed beta-cells, several methods are well known in the art, and have been used clinically in humans, including, but not limited to, the use of drugs that suppress the immune system, such as cytoxan, FK506, or sirolimus; or reagents that block co-stimulatory molecules such as antibodies to CTLA-4 (Shapiro et al. *New Engl. J. Med.* 2000 343(4):230-8; Griffin et al. *J. Immunol,* 2000 164(9):4433-42). Patients are treated with the anti-autoimmune therapy starting 1-2 days prior to DNA administration, and maintained on the immunotherapy afterwards.

After the procedure, the blood glucose is monitored closely, as often as hourly, or by use of a continuous glucose monitor, and insulin therapy by subcutaneous injection decreased or stopped as needed. If blood glucose does not completely normalize without exogenous insulin, the procedure is repeated. To monitor for recurrent autoimmune destruction of the new beta-cells, the blood glucose is monitored periodically. In addition, direct evidence of an immune response to new cells can be tested by assaying for autoreactive T cells, antibodies to glutamic acid decarboxylase (anti-GAD antibodies) or to islet antigens (islet cell antibodies or ICA). Evidence of recurrent autoimmunity can be treated with an increase or other change in the immunosuppression therapy.

Example 20

Characterization of and Regulation of the NEUROGENIN3 Promoter

The following experiments provide for characterization of the Ngn3 promoter, as well as identification of factors both upstream and downstream of Ngn3 that participate in the regulatory pathway that controls Ngn3 expression.

Materials and Methods

The following materials and methods were used in the present example.

Cloning of the mouse and human ngn3 gene promoter. A lambda phage genomic clone containing the mouse neurogenin 3 open reading frame, clone 17/6-1-1-2 (Sommer et al. *Mol. Cell. Neurosci.* 8:221-241, 1996) was used. From this phage clone, a 1 kb fragment containing sequences upstream of the open reading frame was subcloned and sequenced. Human neurogenin 3 genomic clones were obtained by screening a lambda DASH human genomic library with the mouse neurogenin 3 genomic fragment. The clone containing the longest 5' flanking sequence, clone 14H, was subcloned, sequenced, and used for generating reporter gene plasmids.

5' Rapid amplification of cDNA ends (RACE). The 5' end of the mouse ngn3 cDNA was identified by 5'-RACE, using a modification of the protocol from the 5'-RACE System Version 2.0 (GibcoBRL). For mouse cDNA, 2.5 pmol of specific primer JL1 (5'-ATCCTGCGGTTGGGAA-3' (SEQ ID NO:7)) was annealed to 1 μg of total RNA from mouse E15.5 pancreas. Reverse transcription was carried out using SuperScript II reverse transcriptase (GibcoBRL). After first strand cDNA synthesis, the original mRNA template was removed by treatment with RNase and homopolymeric dCTP tails was then added to the 3'-end of the cDNA using terminal deoxynucleotidyl transferase. These products were used as a template in performing 35 cycles of PCR using the 5' RACE Abridged Anchor Primer (Gibco BRL) and JL2 (5'-TGGAAGGTGTGTGTGTGCCAG-3' (SEQ ID NO:8)) as primers. For the nested PCR, Abridged Universal Amplification Primer (Gibco BRL) and JL3 (5'-GATCTAGAGACTTAGAGGTCACTGC-3' (SEQ ID NO:9)) were used as primers, and 35 cycles of PCR were performed. The PCR products were subcloned and sequenced.

Reporter gene constructs. To generate reporter plasmids, fragments of the 5' region of the human ngn3 gene obtained by restriction digestion were ligated upstream of the luciferase gene in the plasmid pFOXLucl or upstream of the TK minimal promoter gene in the plasmid pFOXLuc1TK (Mirmira et al. *J Biol Chem* 275:14743-51, 2000).

Cell culture and transient transfections. βTC3 cells, αTC1.6, and MPAC cells were grown in Dulbecco's Modified Eagle Medium (DMEM) supplemented with 2.5% fetal bovine serum and 15% horse serum. NIH3T3 cells were grown in DMEM medium supplemented with 10% calf serum. Cos7 cells were grown in DMEM medium with 10% fetal bovine serum with 4 mM glutamine. For transient mammalian cell transfections, cells were plated in six-well tissue culture plates 24 h before transfection. For the standard reporter gene analysis, 2 μg of luciferase reporter plasmids were transfected into the cells using TRANSFAST™ lipid reagent (Promega) according to the manufacturers instructions. For assessing the effect of the expression of HES1 on the ngn3 promoter, we cotransfected the amount of HES1, or dominant negative Hes1 (pcDNA3Hes1 (kindly provided by R. Kageyama, Kyoto University (Sasai et al. Genes Develop. 6:2620-2634, 1992) expression plasmid DNA indicated with 2 μg of luciferase reporter plasmids. Forty-eight hours after transfection, cells were harvested and luciferase assays were performed as described previously (German et al. *Genes & Dev.* 6:2165-2176, 1992). Luciferase activity was corrected for cellular protein concentration. All reporter gene analyses were performed on at least three occasions and data are expressed as mean±SEM.

Generation of transgenic mouse and detection of β-galactosidase. The plasmids pNAT6B and pNAT3B were generated by ligating human ngn3 promoter fragments extending from −5.7 kb to +261 bp and from −2.6 kb to +261 bp upstream of the human β-globin intron and the bacterial α-galactosidase gene. Each plasmid was linearized and microinjected (1.5 ng/μl) into murine pronuclei. The injected embryos were transferred to pseudopregnant females and the fetal pancreata with stomach and small intestine were harvested at e15.5 from the founder mice. Tissues were pre-fixed for 30 minutes at 4° C. in 4% paraformaldehyde, and then incubated overnight in X-gal (400 μg/ml) substrate at 37° C. (−2.6 kb promoter) or room temperature (−5.7 kb promoter). Tissues were then fixed again in 4% paraformaldehyde for 30 minutes, paraffin embedded, and sectioned at 5 μM. Genotype was determined by PCR using primers specific for the human ngn3 promoter sequence. β-galactosidase activity was assayed in 6 independent founder fetuses that had integrated the −2.6 kb promoter construct, and in 8 independent founder fetuses that had integrated the −5.7 kb promoter construct.

Immunohistochemistry. Immunohistochemistry was performed on paraffin embedded sections as described previously (Schwitzgebel et al. *Development* 127:3533-3542, 2000.). Primary antibodies were used at the following dilutions: guinea pig anti-insulin (Linco), 1:5000; guinea pig anti-glucagon (Linco), 1:10000; rabbit anti-ngn3 (Schwitzgebel et al. *Development* 127:3533-3542, 2000), 1:5000. Biotinylated secondary antibodies (Vector) were detected with the ABC Elite immunoperoxidase system (Vector).

Preparation of proteins and electrophoretic mobility shift assay (EMSA). HNF3β and HNF la proteins were produced in vitro using SP6 and T7 TNT Quick Coupled Lysate SystemX (Promega) using pGEM-1 ratHNF3β (generous gift from R. Costa, University of Illinois at Chicago) and pcDNA3-HNF 1α (generous gift from M. Stoffel, Rockefeller University) as templates. Glutathione S-transferase (GST) fused HES1 protein was produced in *Escherichia Coli* BL21 competent cells using the pGEX2T plasmid system (Promega). Nuclear extracts from αTC1.6 cells, βTC3 cells, and NIH3T3 cells were prepared following the procedure described by Sadowski and Gilman (Sadowski and Gilman. *Nature* 362:79-83, 1993).

Single-stranded oligonucleotides corresponding to the sequences in the human ngn3 promoter were 5' end-labeled with [γ-$^{32}$P]-ATP using T4 polynucleotide kinase. The labeled oligonucleotides were column-purified and annealed to an excess of the complementary strand. For HNF3β and HNF 1α binding experiments, EMSA buffers and electrophoresis conditions were as previously described (Mirmira et al. *J Biol Chem* 275:14743-51, 2000). For HES-1 binding experiments, conditions were the same except that the poly (dI-dC) concentration was decreased to 15 ng/ul. One μl of the in vitro reaction mixture or 2 ug of nuclear extracts or 400 ng of GST-fused Hes1 protein were used for each binding reaction. When using antibodies, 1 μl of each antibody was incubated with the binding mix for 15 min at room temperature prior to gel-electrophoresis. The antisera against HNF-3α, -3β, and -3γ were a generous gift from R. Costa (University of Illinois) and the HES-1 antiserum was a generous gift from Y. Jan (University of California San Francisco). The anti-HNF-1α antiserum was purchased from Santa Cruz Biotechnology, Inc.

The following oligonucleotides were used as labeled probes or competitors in EMSA reactions (top strands shown):

```
H3-1:
GATCTCTCGAGAGAGCAAACAGCGCGGCGG      (SEQ ID NO: 10)

H3-2:
TTATTATTATTTTAGCAAACACTGGAGACAG     (SEQ ID NO: 11)

H1:
ATCTCTTGTAATTATTTATTAAACGAAATCTATT  (SEQ ID NO: 12)

H2:
TTAAACGAAATCTATTTATTATTATTTTAGCAAA  (SEQ ID NO: 13)

H1P:
GATCTCGCCACGAGCCACAAGGATTG          (SEQ ID NO: 14)

E1:
GATCTAAATTTCCCCATGTGTAACGTGCAG      (SEQ ID NO: 15)

N1:
GATCTGGAGCGGGCTGGCGTGGCGCGGCCCCG    (SEQ ID NO: 16)

N2:
GATCTGCCGGGCAGGCACGCTCCTGGCCCGG     (SEQ ID NO: 17)

N3/4:
GATCTAAAGCGTGCCAAGGGGCACACGACTG     (SEQ ID NO: 18)
```

Mapping the Human ngn3 Promoter

Figure 12:
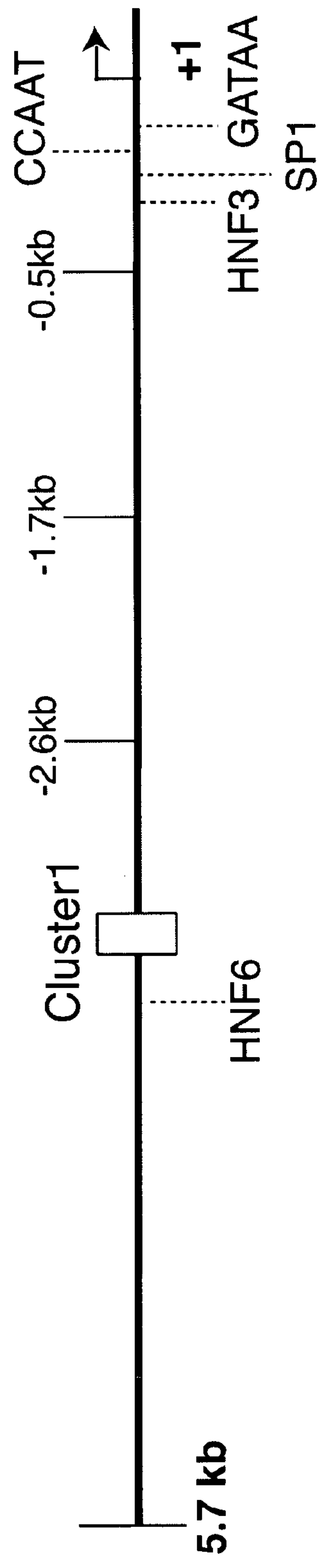
FIGS. 12-13 are schematics showing the human neurogenin 3 gene promoter.
Figure 13:
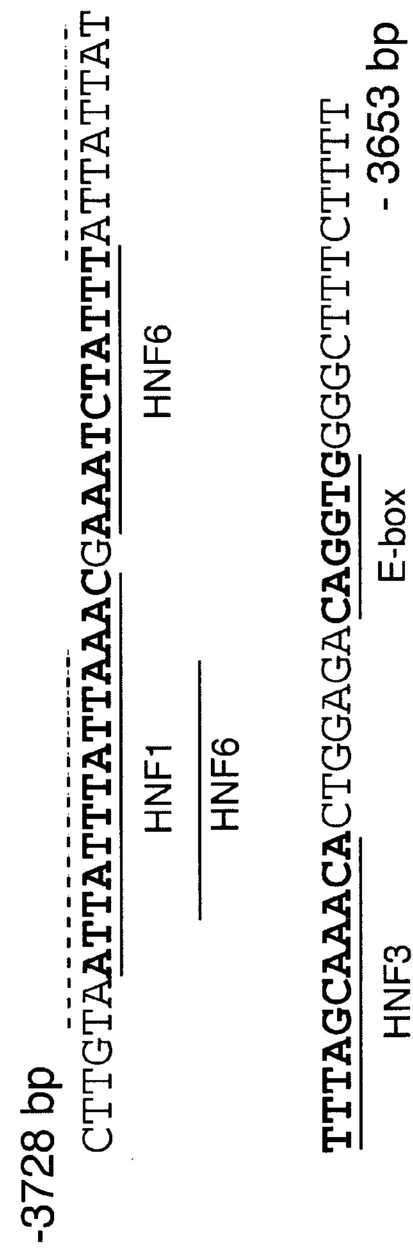

As an initial step in understanding the regulation of neurogenin3 gene expression, the sequences of mouse and human neurogenin3 promoters were determined (FIGS. 12-13). Using RNA purified from embryonic day 15.5 fetal mouse pancreas, the transcription start sites of the murine ngn3 gene was determined by 5' Rapid Amplification of cDNA Ends (5' RACE). All 5' RACE products identify the same start site, 30 base pairs downstream from a putative TATAA box (FIG. 13). The region upstream of the start site is highly conserved in mouse, human and rat, with the region of highest homology in mouse and human extending approximately 300 bp upstream. A CCAAT sequence element lies at −85 bp relative to the transcription start site. Several other potential sequence elements are identified in FIG. 13.

Activity of the Promoter in Cell Lines

Figure 14:
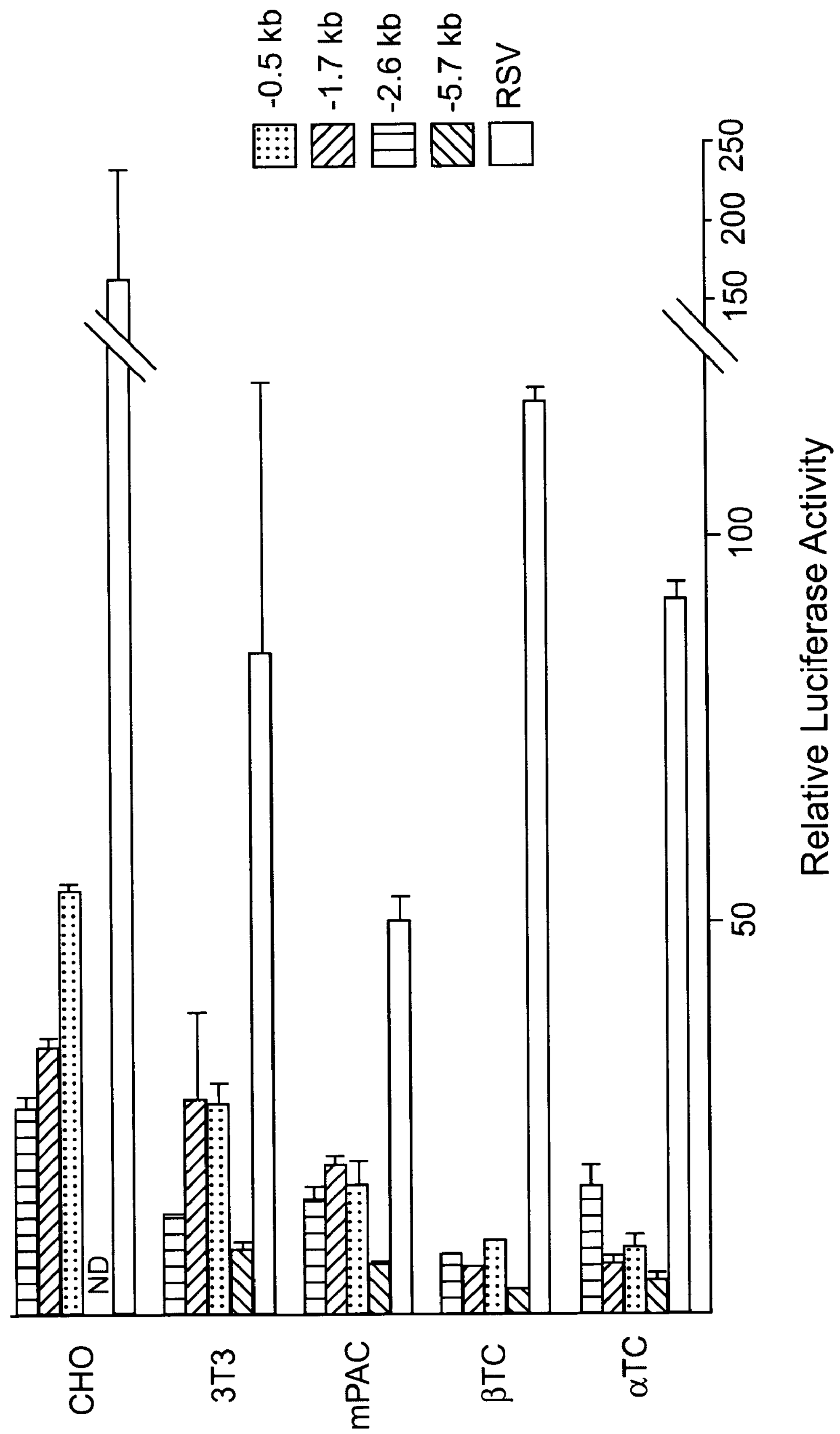
FIG. 14 is a graph showing the function of the human neurogenin 3 promoter in cell lines. Promoter fragments containing sequences extending from the 5' end indicated to +261 bp were ligated upstream of the firefly luciferase gene and transfected into the cell lines shown. Reporter gene activity is expressed relative to the promoterless luciferase vector in the same cell type. Transfections were performed in triplicate on at least two occasions and errors are shown as +/−the standard error of the mean. ND, not done.

A series of progressive 5'deletions of the neurogenin3 promoter each extending to +261 bp on the 3' end were linked to the firefly luciferase gene and were tested in cell lines (FIG. 14). Serial deletions down to −502 bp do not diminish the promoter activity in vitro. Surprisingly, the promoter drives transcription at a high level in all the tested cell lines, including the fibroblast cell lines. This high non-specific activity appears to reside in the proximal promoter, since the shortest construct is still very active in all the examined cell lines.

Activity of the Promoter in Transgenic Mice

While transient transfections in cell lines may provide some indication of promoter activity, these tumor cells are not representative of the cells in the developing pancreas where neurogenin3 is normally expressed. Therefore, mice were produced carrying a transgene with either 5.7 kb or 2.6 kb of the upstream sequence from the human neurogenin3 gene driving the bacterial gene encoding β-galactosidase. Founder mice were harvested at embryonic day 15.5, at the normal peak of neurogenin3 expression in the fetal mouse pancreas (Schwitzgebel et al. Development 127:3533-3542, 2000).

Animals carrying the 5.7 kb construct strongly and selectively express β-galactosidase in central regions of the developing pancreas and in the gut epithelium, the same regions where neurogenin3 is normally expressed at this time during development. Although the level of α-galactosidase expression was significantly lower with the 2.6 kb construct than with the 5.7 kb construct, the overall pattern of β-galactosidase expression was the same.

Immunohistochemistry was used to identify the cells expressing β-galactosidase in the transgenic mice carrying the 5.7 kb promoter construct. The β-galactosidase expressing cells are predominantly localized to the ducts. Most of the β-galactosidase expressing cells do not express islet hormones, although occasional β-cells co-express insulin and β-galactosidase.

Despite the close co-localization of β-galactosidase activity and neurogenin3 protein expression specifically in the same regions of the developing pancreas and gut, there is not a perfect match. Some of the β-galactosidase positive cells co-express high levels of neurogenin 3, but many do not, and many neurogenin 3-expressing cells contain little or no β-galactosidase activity. Most likely this discrepancy derives from differences in the timing of accumulation and degradation of the two gene products, rather than a difference in the onset and extinction of gene expression.

The exact timing for initial detection of each gene product in a particular cell depends on its rate of accumulation and threshold for detection, and therefore should not be expected to be identical. In addition, some neurogenin3 expressing cells may randomly silence the transgene, a poorly understood phenomenon observed with many promoters in transgenic mice (Graubert et al. Nucleic Acids Res 26:2849-58, 1998). The very brief but abundant expression of neurogenin 3 in progenitor cells indicates that the mRNA and protein accumulate rapidly but have very short half-lives. β-galactosidase in contrast has a fairly long half-life in mammalian cells (Smith et al. J Virol 69:4593-9, 1995) and could be expected to peak later and persist in cells after neurogenin3 is no longer detectable. Therefore many of the β-galactosidase expressing cells represent a stage of islet cell differentiation that occurs after neurogenin 3 gene production has ceased, but before hormone expression has started. The large number of these cells suggests that this intermediate stage of differentiation may last longer than the initial neurogenin 3 expressing stage.

Intestinal Expression

Starting at E115.5, endogenous β-galactosidase expression can be detected at low levels along the brush border of the intestinal villi in both transgenic and non-transgenic embryos. Stronger β-galactosidase activity can also be detected in a speckled pattern that is most prominent in the small intestine of the transgenic mice but is absent in their non-transgenic littermates. Sectioning of the gut revealed that this β-galactosidase signal derives from scattered cells within the intestinal epithelium. This pattern of β-galactosidase expression suggests that the neurogenin 3 promoter is also active in a subset of progenitor cells in the developing gut. These may be progenitors for gut endocrine cells. As in the pancreas, this β-galactosidase activity partially overlapped endogenous neurogenin 3 expression, again suggesting that the peak of β-galactosidase accumulation is delayed relative to neurogenin 3.

Multiple Factors Bind to the Neurogenin3 Promoter

To identify nuclear factors that bind to the ngn3 promoter, a series of oligonucleotides were synthesized. The oligonucleotides, which spanned potentially important DNA binding sites within the promoter, were tested for binding to nuclear proteins by electromobility shift assay (EMSA).

Figure 15A:
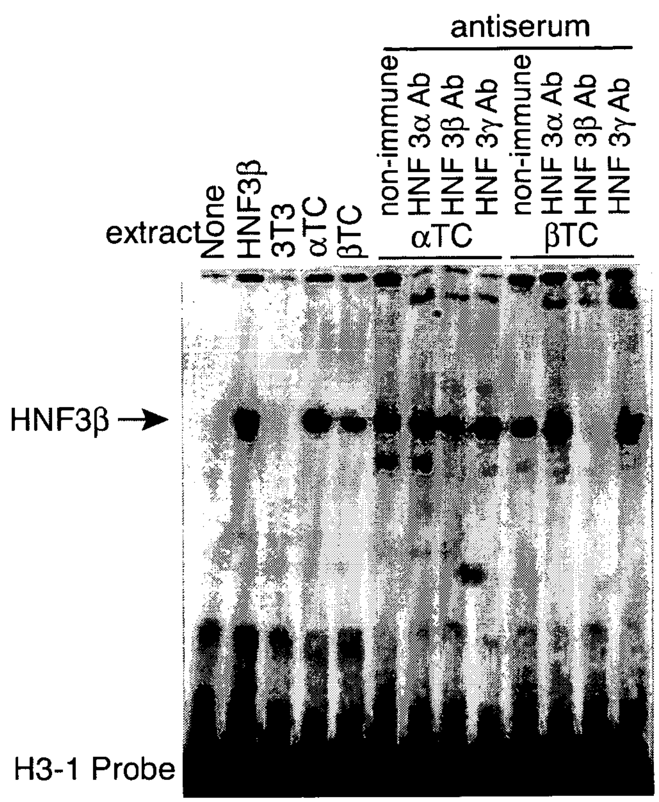
FIGS. 15A-15B are photographs of electromobility shift assays illustrating HNF3 binding to the human ngn3 promoter.
Figure 15B:
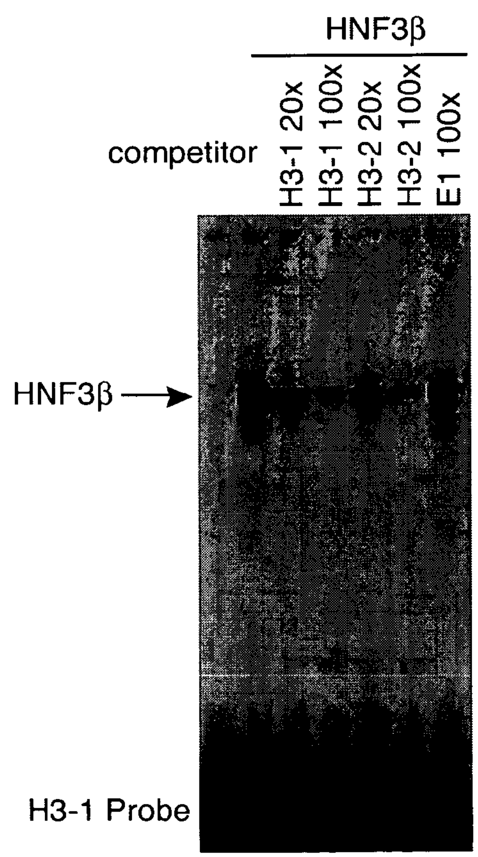

Members of the HNF3 family of winged helix transcription factors have been implicated in pancreatic development and islet function (Wu et al. *Mol Cell Biol* 17:6002-13, 1997; Gerrish et al. *J Biol Chem* 275:3485-92, 2000; Sharma et al. *Mol Cell Biol* 17:2598-604, 1997; Duncan et al. *Science* 281:692-5, 1998; Philippe et al. *Mol Cell Biol* 14:3514-23, 1994; Kaestner et al. *Genes Dev* 13:495-504, 1999). Based on their similarity to a consensus HNF3 binding site (Costa et al. *Mol Cell Biol* 9:1415-25, 1989), there are several potential HNF3 binding sites within the 5.7 kb human neurogenin3 promoter. Two of the most promising sites lie at −3687 bp and at −200 bp. EMSA testing of these binding sites showed that both sites bind with high affinity to in vitro produced HNF3β (FIGS. 15A-B). Using extracts from βTC3 and αTC1.6 cells, a single major complex binds to both sites, and is recognized specifically by an antiserum to HNF3P. In addition, co-expression of HNF3p can activate the neurogenin3 promoter in transiently transfected 3T3 fibroblast cells (data not shown).

The −3687 bp HNF3β binding site forms part of a cluster of potential DNA binding sites for known pancreatic transcription factors (FIGS. 12-13), including potential sites for hox type homeodomain transcription factors, as well as cut-homeodomain transcription factor HNF6 and the Pou-homeodomain HNF1 factors (Courtois et al. Science 238:688-92, 1987). HNF6 binding to the neurogenin3 promoter has been demonstrated previously (Jacquemin et al. Mol Cell Biol 20:4445-54, 2000).

Figure 16:
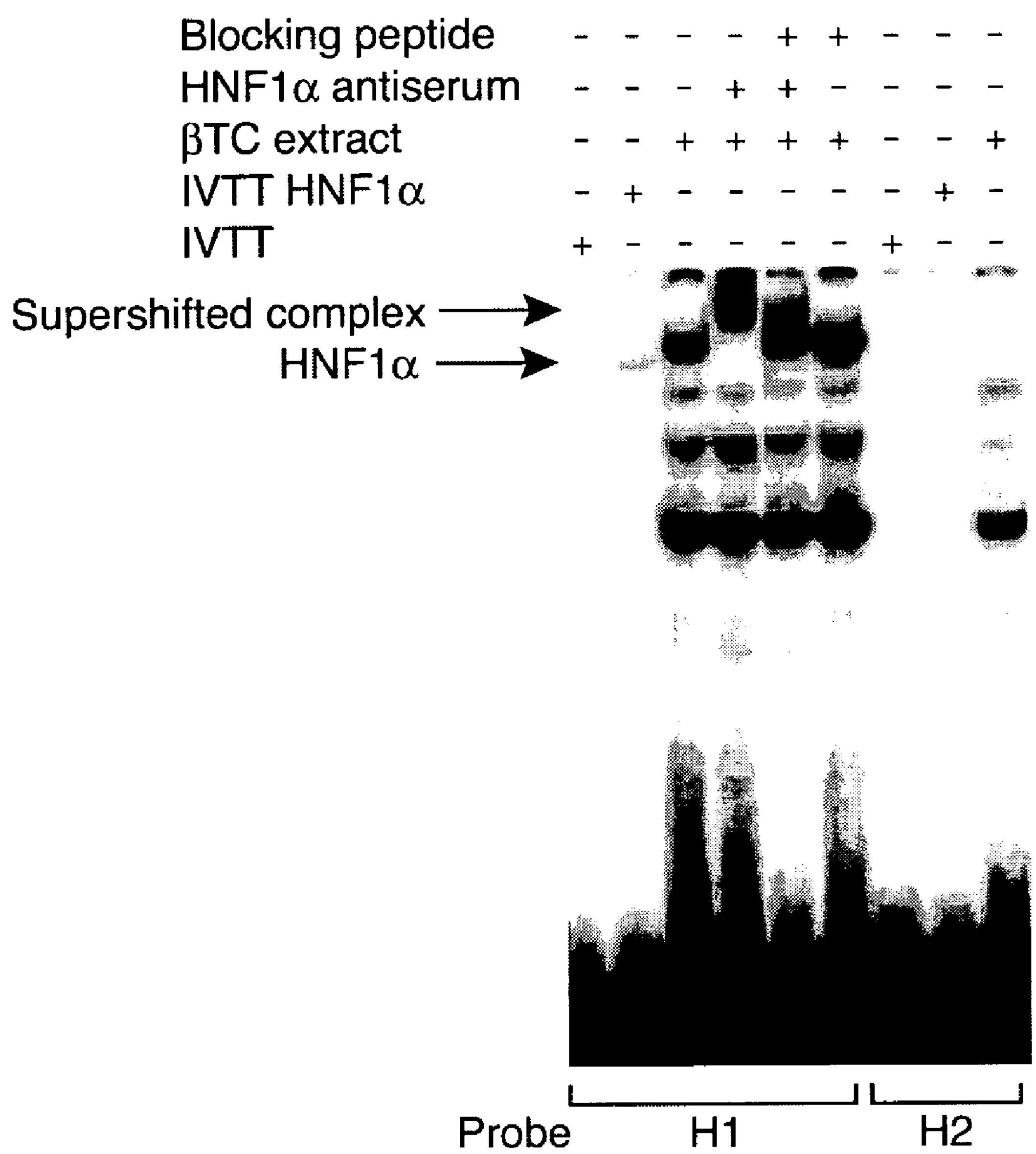
FIG. 16 is a photograph of a electromobility shift assays showing that HNF1 binds to the human ngn3 promoter.

An oligonucleotide spanning the potential HNF1 binding site was tested by EMSA and found that it can bind to in vitro produced HNF-1α. In addition, in nuclear extracts from βTC3 cells, a major low mobility complex binds to the oligonucleotide and is recognized specifically by antiserum to HNF1α (FIG. 16). The similar hox homeodomain-type binding site immediately downstream of the HNF1α binding site will not bind HNFla.

HES-1 Inhibition of the Neurogenin3 Promoter

Figure 17A:
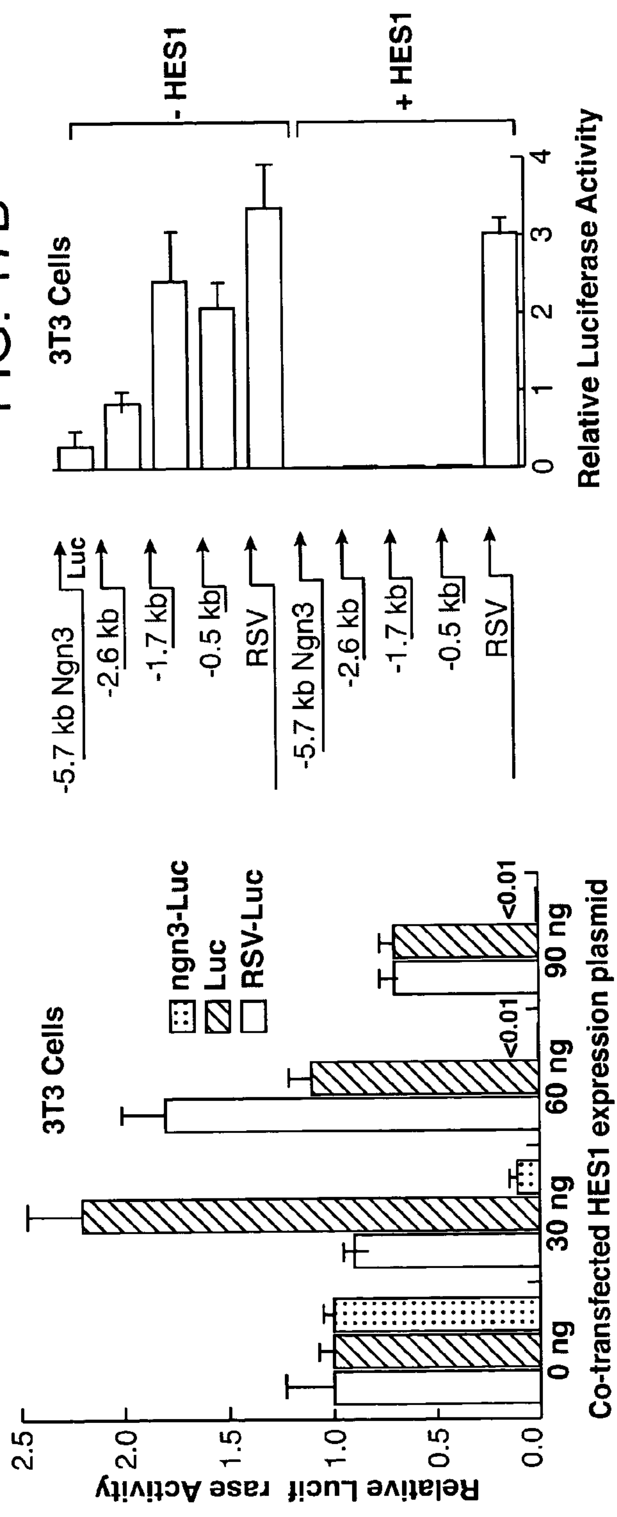
FIGS. 17A-17C are graphs showing that HES1 inhibits the neurogenin3 promoter.
Figure 17B:
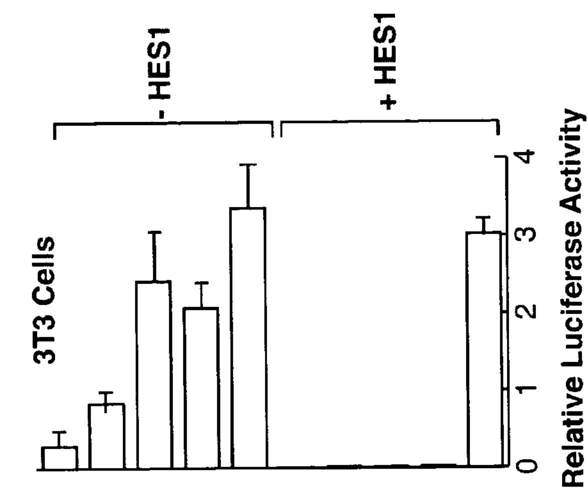
Figure 17C:
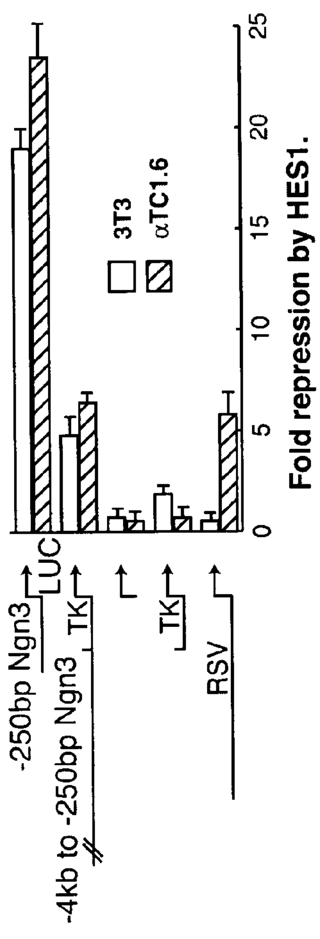

It has been proposed that Notch receptor signaling through the transcriptional regulator HES-1 may prevent the expression of neurogenin3 in all but a small subset of the cells in the developing pancreas (Jensen et al. *Nat Genet* 24:36-44, 2000). To test the ability of HES-1 to directly inhibit the neurogenin3 promoter, the HES-1 cDNA was expressed from a CMV promoter-driven expression plasmid in 3T3 cells along with the neurogenin3 promoter luciferase plasmid (FIGS. 17A-17C). HES-1 dramatically and specifically inhibits the neurogenin3 promoter. Removal of 5' sequences down to −502 bp does not significantly reduce the ability of HES-1 to inhibit the promoter.

To further map sequences competent to respond to HES-1 repression, plasmids were constructed with either the human ngn3 gene promoter sequence from −208 bp to +40 bp (proximal promoter (FIG. 18A)) linked to the firefly luciferase gene, or the sequences from −2.6 kb to −208 bp (distal promoter) upstream of the herpes virus Thymidine Kinase (TK) promoter linked to the firefly luciferase gene. The small proximal promoter retains most of the capacity for HES-1 repression, while the distal sequences are repressed weakly by HES-1.

Figures 18A, 18B, 18C:
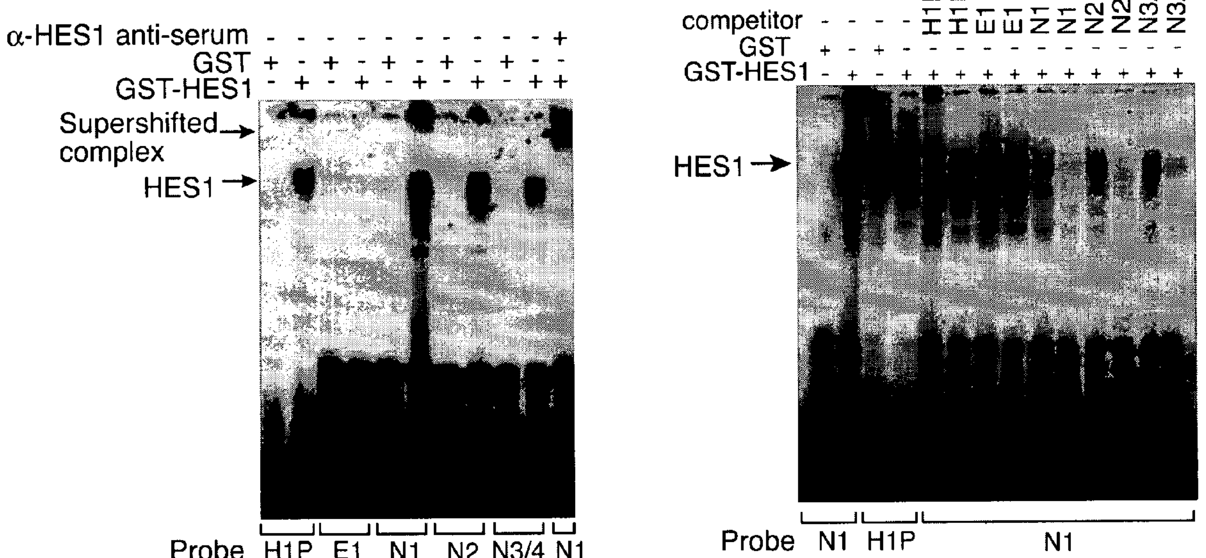
FIG. 18A is a schematic of the DNA sequence immediately upstream of the transcription start site (+1) of the human ngn3 gene is shown. Potential HES1 binding sites (N boxes) are indicated (SEQ ID NO:52).
FIGS. 18B-18C are photographs of electromobility shift assays showing that HES1 binds to the human ngn3 promoter.

Within the proximal 208 bp of the promoter, there are several potential HES-1 binding sites based on the consensus binding sites for HES-1 (CTNGTG) (Takebayashi et al. *J Biol Chem* 269:5150-6, 1994) and its Drosophila homologs hairy/enhancer-of-split (CGCGTC) (Van Doren et al. *Genes Dev* 8:2729-42, 1994; Ohsako et al. *Genes Dev* 8:2743-55, 1994) (FIG. 18A). Three oligonucleotides containing four of these sites were tested for binding to bacterially produced HES-1 protein by gel mobility shift assay (FIG. 18B). All three oligonucleotides bind HES-1, and do so with greater affinity than the previously described high affinity tandem sites from the mouse HES-1 gene (Takebayashi et al. *J Biol Chem* 269:5150-6, 1994) (labeled H1 in FIG. 18C). All four of these sequences are conserved in the mouse neurogenin3 promoter (FIG. 11).

Example 21

Characterization of Islet Transcription Factor Regulatory Pathway

The following experiment provides for characterization of the transcription factors involved in islet cell formation.

Briefly, the coding sequences for β-galactosidase, human neurogenin3 (SEQ ID NO:1), mouse NeuroD1 (available at GenBank accession number BC018241, and provided in the Sequence Listing as SEQ ID NO:40), mouse Mash1 (Guillemot and Joyner (1993) Mech. Dev. 42(3):171-85), and mouse myoD were inserted into the pACCMV-pLpA plasmid and recombinant adenoviruses were produced using previously described methods (Berman et al., (1998) J. Biol. Chem. 273:26421-26425; Becker et al. (1994) Methods Cell. Biol. 43:161-189). Adenovirus vectors expressing β-galactosidase (adCMV-Bgal), neurogenin3 (human) (adCMV-Ngn3), NeuroD1 (mouse) (adCMV-ND 1), mash1 (mouse) (adCMV-Mash1), or myoD (mouse, muscle bHLH gene) (adCMV-MyoD) were used to infect two mouse pancreatic ductal cell lines, MPAC L20 and mPAC L4S2.

Figure 19A:
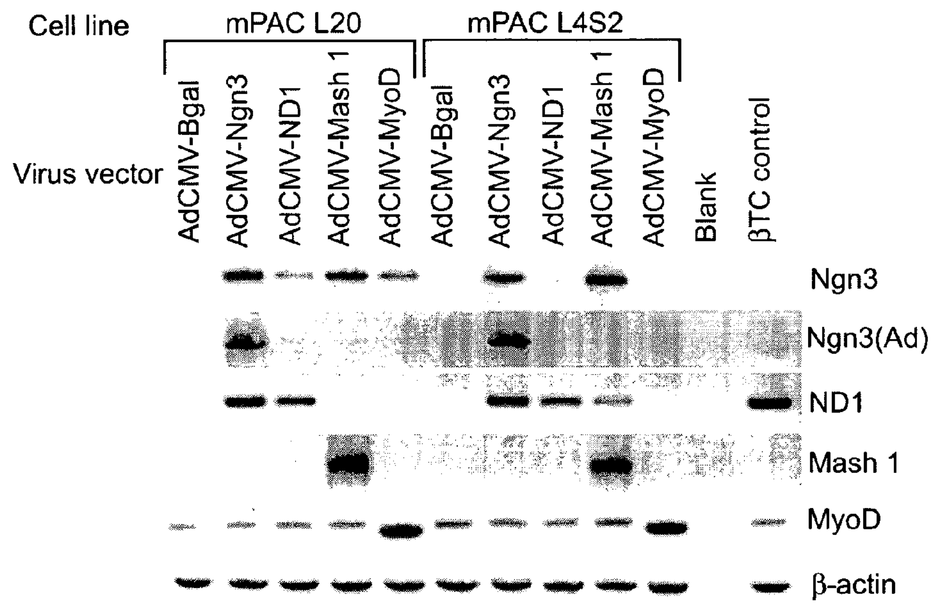
FIGS. 19A-19C are photographs of agarose gels showing the effect of transfection of adenoviral vectors expressing β-galactosidase (adCMV-Bgal), neurogenin3 (human) (adCMV-Ngn3), neuroD1 (mouse) (adCMV-ND1), mash1 (mouse) (adCMV-Mash1), or myoD (mouse, muscle bHLH gene) (adCMV-MyoD) in two mouse pancreatic ductal cell lines, mPAC L20 and mPAC L4S2.
Figure 19B:
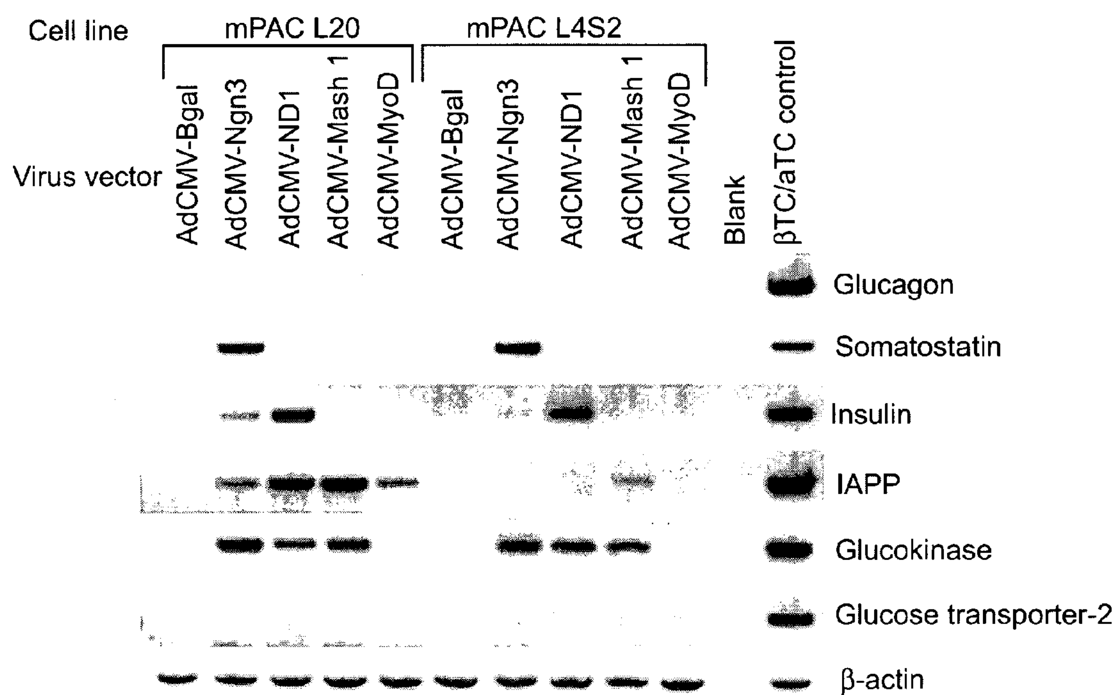
Figure 19C:
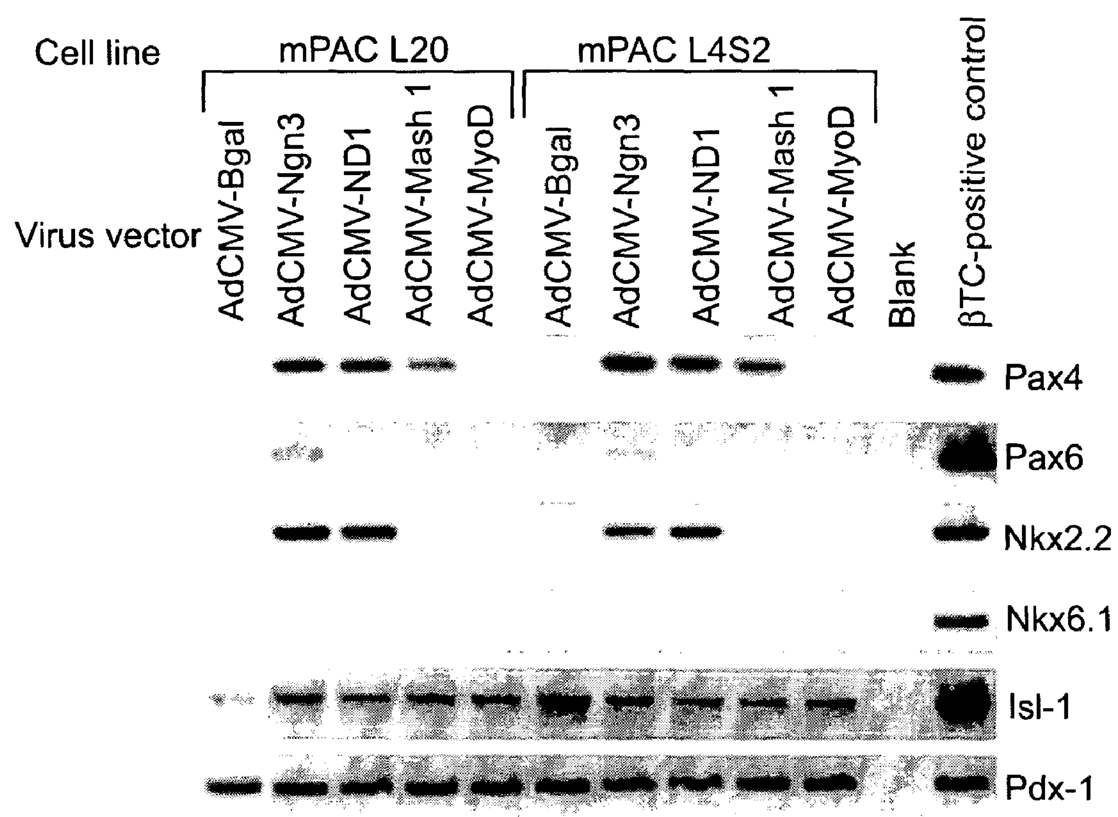

After 48 hours, the cells were harvested, RNA was isolated, and RT-PCR was performed for Ngn3, ND 1, Mash1, MyoD, β-actin, glucagon, somatostatin, insulin, IAPP, glucokinase, glucose transporter 2, Pax4, Pax6, Nkx2.2, Nkx6.1, Isl-1, and Pdx-1. RT-PCR products were separated by electrophoresis through an agarose gel, stained with ethidium bromide, and photographed. The results are shown in FIGS. 19A-19C. Identities of the PCR products were confirmed by purifying the products from the agarose gel, inserting the purified fragments of DNA into a bacterial plasmid vector, and sequencing the insert. These data demonstrated that neurogenin3 can induce endocrine differentiation, with activation of a whole set of genes involved in islet cell differentiation and function.

Methods And Materials For Examples 22-23

The following are the methods and materials for Examples 22-23.

Electromobility Shift Assays. Single stranded oligonucleotides were 5'-end labeled using (γ-32P) ATP and T4 polynucleotide kinase. An excess of complementary strand was then annealed to form a duplex strand that was column purified. EMSA buffers and electrophoresis conditions were as described above using 500 ng of poly(dIdC):poly(dIdC) per 10 ul binding mix. For in vitro produced protein, 1 μl of the 50 μl total reaction volume was used per binding mix.

Oligonucleotides used were as follows (coding strand shown from each double stranded pair): NEUROG3 promoter E element, 5'-ctttgtccggaatccagctgtgccctgcgggggag-3'; rat insulin I promoter E2 element, 5'-ctgcttcatcaggccatctggcccct-tgttaataa-3'; PAX4 promoter E element, 5'-tgtataattgtgagca-gatggcgggggctggcggc-3'; nkx2.2 promoter E3 element 5'-ttattaccgctgaacatatggccaatattttgact-3'. EMSA results are representative of those seen on at least 3 occasions.

In vitro protein production. The cloning and construction of in vitro expression vectors containing the cDNAs encoding E47, neurogenin3, and neuroD1 ligated downstream of the T7 phage promoter have been previously described (Smith et al. (2000) J. Biol. Chem. 275:36910-9). Proteins were produced using the TNT-coupled reticulocyte lysate system (Promega, Madison, Wis.) according to the manufacturer's instructions to provide a total reaction volume of 50 μl from 1 μg of DNA template.

Luciferase reporter contructs. The longer NEUROG3 promoter luciferase constructs were described in Lee et al. (2001) Diabetes 50:928-36). The shorter promoter fragments were generated by PCR and ligated upstream of the luciferase gene in the plasmid pFOXLucl. A 2 bp mutation was introduced into the proximal NEUROG3 promoter E box in the intact −207 bp promoter by a PCR based technique whereby two complementary primers corresponding to the region, and containing the mutation, were used as PCR primers to amplify the entire plasmid (Aranburu et al. (2001) Biochem. J. 354:431-8) using Pfu Turbo polymerase (Stratagene). The positive strand primer sequence (mutation underlined) was 5'-gccctttgtccggaatctggctgtgccctgcgggga-3'.

The minienhancers containing two copies of the proximal E box used in FIG. 3 were ligated upstream of the TK minimal promoter in the plasmid pFOXLuc 1TK. Oligonucleotides used were as follows (coding strand shown from each double stranded pair): N3E (−105 to −158 of NEUROG3 promoter) 5'-gatcttccggaatccagctgtgccct-gcgggggaggagcgggctcgcgtggcgcggcccg 3', N3mE 5'-gatcttc-cggaatctggctgtgccctgcgggggag-gagcgggctcgcgtggcgcggcccg-3'. The minienhancers used in FIG. 5 contained 6 copies of a 16 bp repeat containing each E box, and were constructed by ligating 2 copies of the following oligonucleotides containing 3 copies of the respective E boxes (16 bp) upstream of the TK minimal promoter in pFOXLuc1TK: Pax4 5'-gatctgtgagcagatggcggggtgagcagatggcggggtgagcagatggcggg-3'; Nkx2.2 5'-gatctctgaacatatggccaactgaacatatggccaactgaacatatggccaag-3'; Ngn3 5'-gatctgaatccagctgtgcccgaatccagctgtgcccgaatccagctgtgcccg-3'.

One hybrid analysis. One hybrid expression vectors were constructed by amplifying the appropriate coding fragments of Neurogenin3 by PCR and then ligating into the EcoRI and BamHI sites of the Gal4 DBD vector (Clontech). Two reporter vectors were constructed carrying DNA binding sites for the GAL4 protein. The low background vector to test for activation was constructed from pFOXluc1 with 5 copies of the GAL4 upstream activating sequence (UAS) ligated upstream of the adenovirus E1b promoter driving the expression of firefly luciferase. The high background vector used to test for repression was constructed from pFOXluc2 with 5 copies of the GAL4 UAS ligated upstream of the HSV-TK promoter driving expression of firefly luciferase. 2 μg of reporter construct and 200 ng of the GAL4 DBD vector were transfected into one million cultured cells using Transfast lipid reagent (Promega) according to the manufacturer's instructions and luciferase activity was determined 48 hours after transfection using the Promega assay system according to the manufacturer's instructions.

Cell culture and transfection. The mouse beta-cell line, pTC3, and the mouse alpha-cell line, αTC1.6, were grown in Dulbecco's modified Eagle's medium (DMEM) supplemented with 2.5% fetal bovine serum and 15% horse serum. NIH3T3 mouse fibroblast cells were grown in DMEM supplemented with 10% fetal bovine serum. In preparation for transfection, cells were split into 6 well plates 24 hours prior to transfection, 1 million cells per well were used for αTC1.6 and βTC3 transfection and 50 thousand per well for NIH3T3 cells. 2 μg of reporter construct was used per well, and 50 ng of any co-transfected transcription factor cDNA was used per well. Transfast (Promega) cationic lipid agent was used for all transfections according to the manufacturers instructions. Cells were harvested 48 hours after transfection and luciferase assays performed with 5 μg of total protein. Transfections were performed on at least 3 occasions, all data are expressed as mean±SEM.

Example 22

Figure 20:
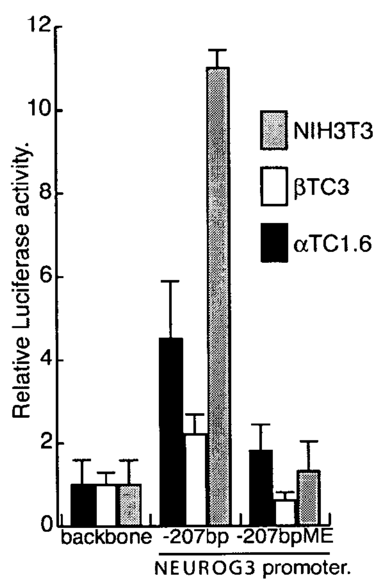
FIG. 20 is a graph showing that NEUROG3 promoter activity is dependent upon an E box located at −149 bp. The three cell lines shown (NIH3T3, βTC3, and αTC1.8 cells) were transfected with reporter plasmids containing the firefly luciferase gene under the control of the either the wildtype −207 bp NEUROG3 promoter, or the −207 bp NEUROG3 promoter containing a 2 bp mutation in the E box (−207 bp ME). Luciferase activities of all samples were determined 48 hrs after transfection and are expressed relative to the activity of the promoterless backbone vector (pFOXluc1). Results are expressed as the mean+/−S.E.M of data from experiments performed in triplicate on at least three separate occasions.

Control of Neurogenin3 Expression—Characterization of the Human Ngn3 Promoter To identify important promoter elements within the proximal promoter of NEUROG3, additional 5' promoter deletions were constructed so as to drive expression of a luciferase reporter gene. A promoter containing only 207 bp upstream of the transcription start site still maintained a significant level of activity. This promoter contains a potentially important E box (a sequence element with the consensus CANNTG that binds to transcription factors in the basic helix-loop-helix family, including neurogenin3 itself) located at −149 bp that is also conserved in the mouse promoter. To test the importance of the −149 bp E box, a 2 bp mutation was introduced in essential bases of the E box consensus and found that the mutation abolished the activity of the proximal promoter in all cell lines tested (FIG. 20).

Figure 21:
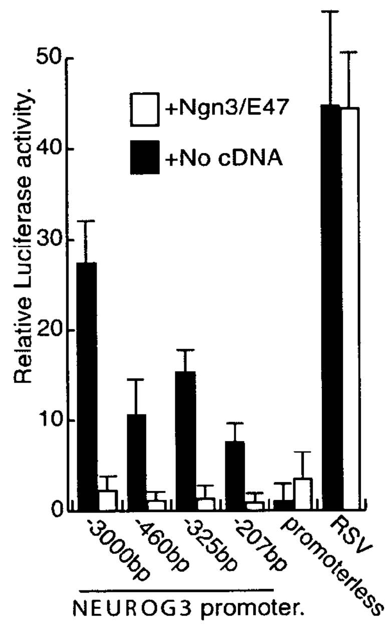
FIG. 21 is a graph showing that Ngn3 represses its own promoter. NIH3T3 cells were transfected with reporter plasmids containing the firefly luciferase gene either with no promoter or under the control of the various length NEUROG3 promoters indicated or the Rous Sarcoma Virus LTR (RSV). Cells were co-transfected with expression plasmids containing the cytomegalovirus (CMV) early gene promoter driving the expression of either no cDNA or the cDNAs for Neurogenin3 and its heterodimeric partner E47. Luciferase activities of all samples were determined 48 hrs after transfection and are expressed relative to the activity of the promoterless backbone vector (pFOXluc1) co-transfected with the expression plasmid containing no cDNA. Results are expressed as the mean+/−S.E.M of data from experiments performed in triplicate on at least three separate occasions.
Figure 22A:
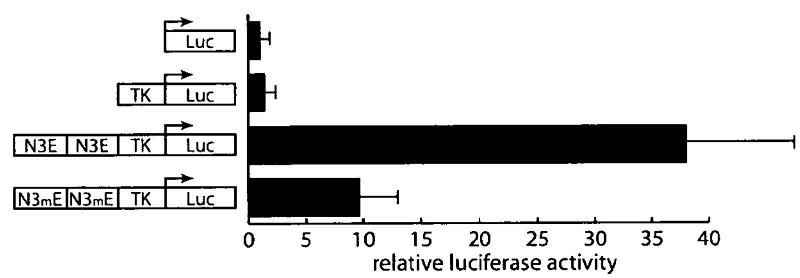
FIGS. 22A-22B is a set of graphs showing the results of transfection experiments that demonstrate that E box activity is conferred upon a heterologous promoter. βTC3 cells were transfected with reporter plasmids containing the firefly luciferase gene under the control of the herpes simplex virus thymidine kinase minimal promoter either by itself (TK) or linked to 2 copies of the NSE minienhancer which contains the sequences from −105 to −158 bp from the NEUROG3 promoter including the proximal E-box or, in (22A), 2 copies of the N3mE minienhancer with a 2 bp mutation of the E box. In (22B), cells were co-transfected with either a control plasmid expressing no cDNA or two plasmids expressing the E47 and neurogenin3 cDNAs under the control of the cytomegalovirus (CMV) early gene promoter. Luciferase activities of all samples were determined 48 hrs after transfection and are expressed relative to the activity in cells transfected with the vector with the isolated TK promoter (TK). Results are expressed as the mean+/−S.E.M. of data from experiments performed in triplicate on at least three separate occasions.
Figure 22B:
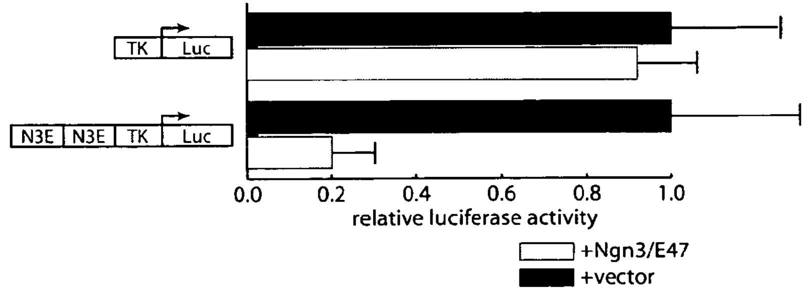

Given the importance of this conserved E box within the proximal promoter, neurogenin3, alone or in conjunction with its heterodimeric partner E47, were tested to determine if they could influence the activity of its own promoter (FIG. 21). Surprisingly, neurogenin3 and E47 repressed the NEUROG3 promoter constructs, but not the control RSV promoter or promoterless constructs. The promoter construct with the mutant E box was not repressed by neurogenin3 (data not shown), but this promoter was already inactive in the absence of neurogenin3. In addition, two copies of a short minienhancer containing the proximal NEUROG3 E box also was active in both alphaTC3 and NIH 3T3 cells, dependent on the E box sequence, and repressed by neurogenin3 (FIGS. 22A-22B and data not shown).

Figure 23A:
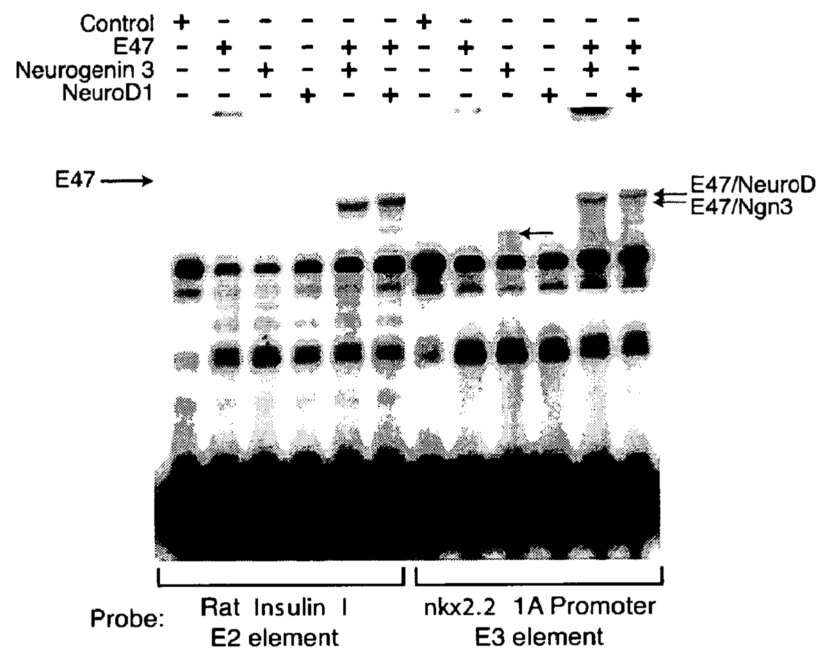
FIGS. 23A-23B are photographs of electromobility shift assays (EMSAs) showing that bHLH factors bind pancreatic promoter E boxes. EMSA were used to test the ability of E47, neurogenin3 and neuroD 1 to bind to labeled, double stranded oligonucleotides containing the E box sequences from the rat insulin I and mouse nkx2.2 promoters (23A) or the human PAX4 and NEUROG3 promoters (23B). 1 μl of each in vitro-translated protein was incubated with the indicated probes, either individually or in the combination shown. Results are typical of experiments done on three occasions.
Figure 23B:
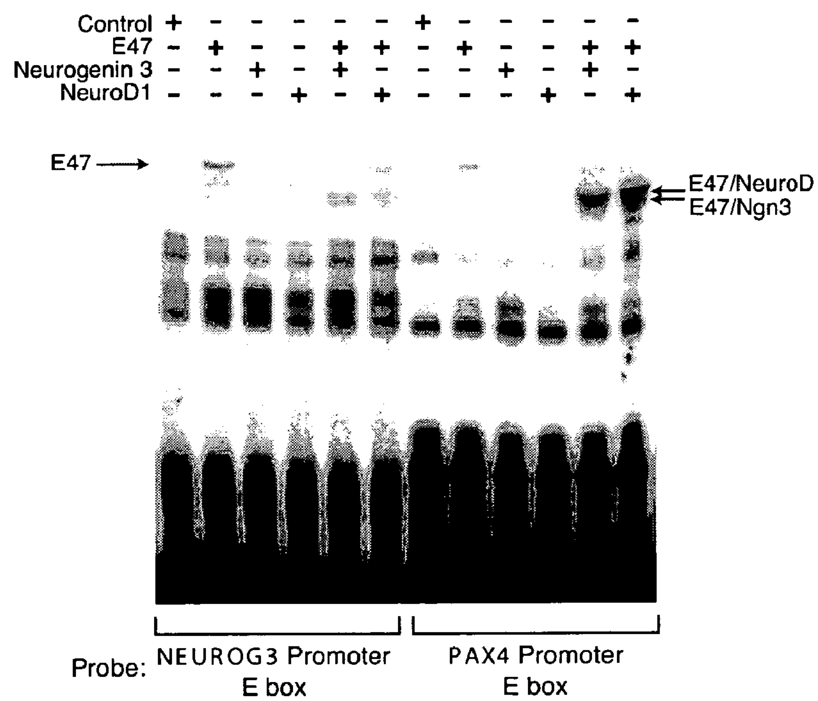

Next, the affinity of the pancreatic bHLH proteins neurogenin3, neuroD1, and E47 for the E box of the NEUROG3 promoter was tested. EMSAs were performed using isolated E boxes from the NEUROG3, nkx2.2, PAX5 and rat insulin I gene promoters as probes in conjunction with in vitro produced proteins neurogenin3, NeuroD1 and their dimeric partner E47 (FIGS. 23A-23B). E47 bound to each of the elements with comparable affinity; and, unexpectedly for class B bHLH factors, homodimers of neuroD1 and neurogenin3 bound to the E box of the nkx2.2 promoter. Heterodimers of E47 with neurogenin3 or neuroD1 bound to all 4 probes tested, with differing relative binding affinities in the order from the NEUROG3 E box (weakest), to the nkx2.2 E3 element, the rat Insulin I E2 element, and the PAX4 E box (strongest).

Figure 24:
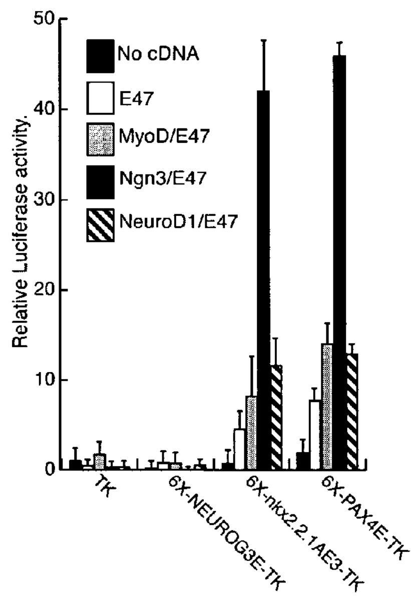
FIG. 24 is a graph showing that the NEUROG3 E box is not activated by the pro-endocrine bHLH factors. NIH3T3 cells were transfected with reporter plasmids containing the firefly luciferase gene under the control of the herpes simplex virus thymidine kinase minimal promoter either by itself (TK) or linked to six copies of the indicated E boxes. Cells were co-transfected with expression plasmids containing the cytomegalovirus (CMV) early gene promoter driving the expression of either no cDNA, the E47 cDNA or the cDNA combinations shown. Luciferase activities of all samples were determined 48 hrs after transfection and are expressed relative to the activity of the vector with the isolated TK promoter (TK) co-transfected with the expression plasmid containing no cDNA. Results are expressed as the mean+/− S.E.M of data from experiments performed in triplicate on at least three separate occasions.

To test the function of the different E boxes from the four genes in isolation, 6 copies of each E box were ligated upstream of the minimal HSV-TK promoter driving the luciferase reporter gene. The activity of the resulting heterologous promoter was determined in the absence and presence of cotransfected factors (FIG. 24). Unlike the other 3 constructs, the NEUROG3 E box construct was not activated by any of the transcription factor combinations. It should be noted that in contrast to this minienhancer construct made from 6 copies of a 16 bp E box sequence, the larger, 54 bp NEUROG3 E box minienhancer used in FIG. 22 was active, and was repressed by Neurogenin3. The higher activity of the larger minienhancer suggests that the ubiquitous activator that requires the NEUROG3 E box either requires a larger binding site, or interacts with factor(s) binding adjacent to the E-box.

Example 23

Identification of Minimal Domains of Human Ngn3

Figure 25A:
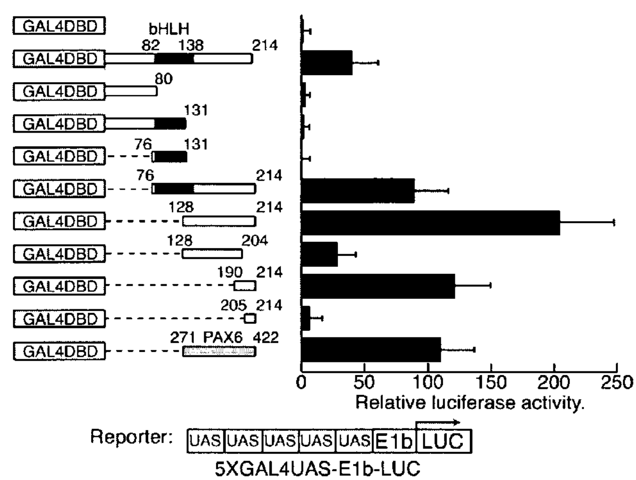
FIGS. 25A-25B are graphs showing the mapping of the activation domains within Ngn3 using one hybrid analysis. In (FIG. 24A), a low background reporter construct comprised of 5 copies of the Gal4 consensus binding site (UAS) ligated upstream of the E1b viral promoter driving luciferase expression was transfected into NIH3T3 cells. The reporter construct was co-transfected with a plasmid expressing a fusion protein comprised of the Gal4 DNA binding domain and the indicated portion of Neurogenin3 protein; a similar construct containing the previously characterized pax6 activation domain was included as a positive control. In (FIG. 24B), a high background reporter construct comprised of 5 copies of the Gal4 UAS ligated upstream of the HSV-TK promoter driving luciferase was transfected into NIH3T3 cells. The reporter construct was co-transfected with a plasmid expressing the GAL4 DNA binding domain fused to the bHLH domain of Neurogenin3 or NeuroD1/Beta2 or to the pax6 activation domain. Luciferase activities of all samples were determined 48 hrs after transfection and are expressed relative to the activity of the luciferase vector co-transfected with the expression plasmid containing the Gal4 DNA binding domain alone. Results are expressed as the mean+/−S.E.M of data from experiments performed in triplicate on at least three separate occasions.
Figure 25B:
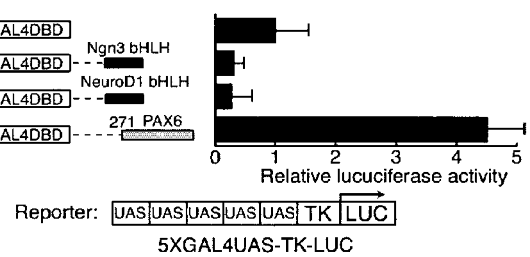

To determine whether transcriptional repression is an inherent property of neurogenin3, to determine the minimal portions of Ngn3 required for transcriptional activation, and to determine whether neurogenin3 thereby could repress its own promoter by a direct mechanism, one hybrid analysis was used to study the transactivating properties of the neurogenin3 protein (FIGS. 25A-25B). Various regions of the protein were fused to the DNA binding domain of GAL4, and the ability of the resulting protein to affect transcription from a promoter containing five GAL4 binding sites was determined.

Several regions of the neurogenin3 protein were able to stimulate transcription, the most potent activation coming from regions encompassing the carboxyl terminus of the protein (constructs 128-214 and 190-214), which was a more potent effect than that exhibited by the pax6 activation domain that served as a positive control.

Only one region of the protein, the isolated basic helix-loop-helix domain, was able to weakly repress transcription. A similar construct containing the equivalent region of the neuroD1 protein acted in a comparable manner suggesting that this weak repression is likely to be a common characteristic of an isolated bHLH domain and not an idiosyncrasy of neurogenin3.

Due to the apparent inability of neurogenin3 to act directly as a transcriptional repressor, it was hypothesized that neurogenin3 may repress its own promoter by competing for binding with another activator or by inducing the expression of a transcriptional repressor which in turn represses the promoter. If the mechanism was purely the first model, then any factor able to bind the E box should be able to compete and thereby repress in a similar manner. The second model would necessitate that the protein contain a transcriptional activation domain to induce expression of a downstream repressor. To test these two possibilities, the −325 bp NEUROG3 promoter reporter construct was cotransfected with plasmids expressing various E-box-binding bHLH proteins. The −325 bp NEUROG3 promoter was used because longer promoters contain additional E boxes.

Figure 26:
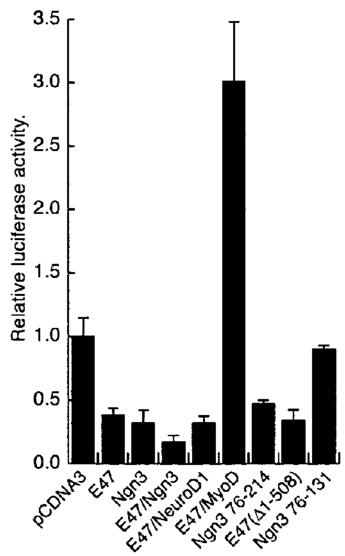
FIG. 26 is a graph showing that pancreatic bHLH factors repress the NEUROG3 promoter. NIH3T3 cells were transfected with a reporter plasmids containing the firefly luciferase gene under the control of the −325 bp NEUROG3 promoter. Cells were co-transfected with expression plasmids containing the cytomegalovirus (CMV) early gene promoter driving the expression of either no cDNA or the wild-type or truncated bHLH cDNAs indicated. Luciferase activities of all samples were determined 48 hrs after transfection and are expressed relative to the activity of the luciferase vector co-transfected with the expression plasmid containing no cDNA. Results are expressed as the mean+/− S.E.M of data from experiments performed in triplicate on at least three separate occasions.

All combinations repressed the NEUROG3 promoter, with the single exception of E47 in combination with the muscle bHLH protein myoD (FIG. 26). Consistent with the competition model for transcriptional repression of the NEUROG3 promoter, a truncated version of E47 (E47(Δ1-598)) containing only the DNA-binding bHLH domain and lacking any activation domain repressed the promoter as efficiently as the wild type protein, thus suggesting that E47 repression is not due to the activation of an additional gene, but may simply result from competition with an activator for binding to the E box. In contrast, the isolated neurogenin3 bHLH domain, which should not bind by itself to the NEUROG3 E-box, did not repress the NEUROG3 promoter. Consistent with the downstream repressor model, however, inclusion of the activation domain allowed neurogenin3 to repress the NEUROG3 promoter. Since neurogenin3 likely normally exits as a heterodimer with E47 or other ubiquitous class A bHLH proteins, the heterodimer may both activate a downstream repressor and compete with an activator. Consistent with this possibility, the greatest repression of the NEUROG3 promoter was produced by the combination of E47 and neurogenin3.

Neurogenin3 activates a cascade of genes involved in islet cell differentiation, but is itself inactivated prior to differentiation, so that it initiates but does not complete the differentiation program. The closely related bHLH gene neuroD1 is activated by neurogenin3 and persists in the mature islet cells where it plays a role in completing and maintaining the differentiated state by driving the expression of such genes as insulin and glucagon. To prevent persistent expression of neurogenin3 once its task of initiating differentiation is achieved, some mechanism must limit the expression of neurogenin3 in the differentiating cells. The data above in Examples 22-23 suggest that autorepression by neurogenin3 of its own expression contributes at least part of this mechanism, by autorepression and through activation of a downstream repressor of the NEUROG3 promoter.

In summary, the pro-endocrine factor neurogenin3 functions as a transcriptional activator, initiating the cascade of gene expression events that leads to the differentiation of pluripotent progenitor cells into mature islet cells in the pancreas. Once this chain of events is initiated, however, neurogenin3 represses its own expression, possibly by both competing with an activator and activating a repressor, allowing differentiation to proceed autonomously.

Example 24

BAC Transgenic Model of Neurogenin3 Expression

Figure 30:
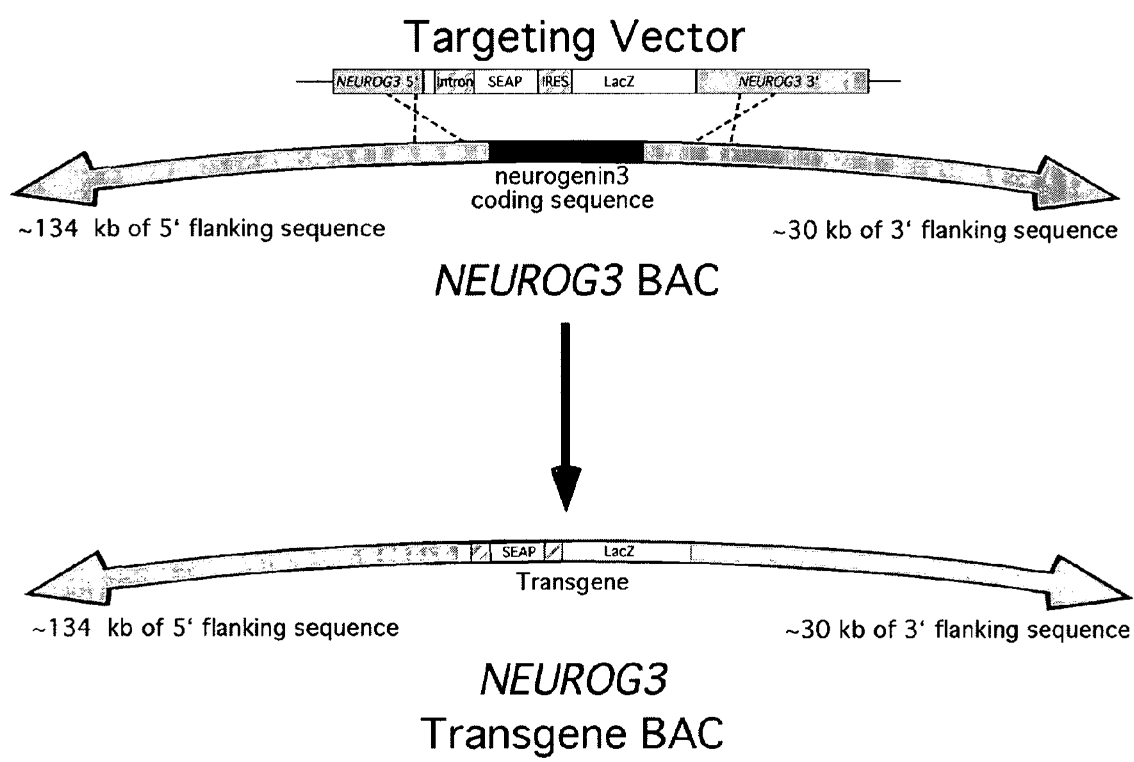
FIG. 30 is a schematic showing the NEUROG3 BAC and its use in production of a transgenic, non-human animal.

A transgenic mouse line was produced which provides a model in which surrogate markers can be used to gauge Neurogenin3 expression in vivo. A 184 kb bacterial artificial chromosome (BAC) containing the hNgn3 gene (NEUROG3) was produced. FIG. 30 provides a schematic showing the BAC and its construction. BAC clone RP11-343J3 was used for construction of the clone (NCBI accession no. AL450311). The NEUROG3-containing BAC included about 134,000 bp of the 5' flanking sequence of hNgn3, and about 30,000 bp of the 3' flanking sequence of hNgn3.

The coding sequence for Neurogenin3 in the BAC was then replaced with a bicistronic gene composed from two readily detectable marker genes, secreted alkaline phosphatase (SEAP) and enhanced green florescent protein (EGFP), separated by a viral IRES (FIG. 30). This construct was used to produce transgenic mice.

The expression of the bicistronic transgene by transient transfection in the pancreatic ductal cell line, mPAC. 1 kb of 5' flanking DNA from the NEUROG3 gene was sufficient to generate a strong GFP signal in transfected cells, and SEAP activity in the media of transfected cells increased linearly over time. Interestingly, the inclusion of 3' flanking sequences from the NEUROG3 gene strongly enhanced SEAP expression, indicating that the NEUROG3 gene contains multiple, dispersed transcriptional enhancers, and underlining the importance of using the large NEUROG3 BAC for producing transgenic mice.

NEUROG3-SEAP/GPF BAC transgenic embryos were harvested and assayed for transgene expression at embryonic days 12.5 and 15.5. Scattered cells expressing EGFP could be detected in the pancreas at E115.5, and SEAP activity could be detected in both the pancreas and the remainder of the embryo at both dates. SEAP secretion rates were assayed by culturing isolated pancreatic buds from E12.5 embryos. SEAP activity initially increased rapidly in the bud culture media, demonstrating initial high levels of NEUROG3 gene expression in vitro.

These results demonstrate the utility of NEUROG3-SEAP/GPF BAC transgenic mice for the in vivo assessment of NEUROG3 gene expression in intact animals or primary cultured tissues. This transgenic mouse will be a useful model for studying the signals that induce islet cell genesis.

The invention now being fully described, it will be apparent to one of ordinary skill in the art that many changes and modifications can be made thereto without departing from the spirit or scope of the appended claims.

What is claimed is:

1. An isolated polynucleotide wherein the polynucleotide comprises a nucleotide sequence having an overall sequence identity of at least 95% to:

a) a contiguous nucleotide sequence of nucleotides positioned at 2485 to 2538 of SEQ ID NO:1;

b) a contiguous nucleotide sequence of SEQ ID NO: 19; or c) a contiguous nucleotide sequence of nucleotides 2435 to 2643 of SEQ ID NO:1;

and is operably linked to a heterologous coding sequence.

2. An expression construct comprising, from 5' to 3':

a polynucleotide comprising a 5' flanking sequence of an Ngn3 gene, where the 5' flanking sequence comprises the polynucleotide of claim 1; and a heterologous nucleic acid encoding a polypeptide wherein introduction of the expression construct into a suitable mammalian cell provides for expression of the heterologous nucleic acid.

3. The expression construct of claim 2, wherein the polypeptide is a reporter polypeptide.

4. An isolated polynucleotide encoding a polypeptide, wherein the overall amino acid sequence identity of said polypeptide is at least 95% to a contiguous amino acid sequence of SEQ ID NO:2 and wherein the polypeptide induces transcription from a human ngn3 promoter when expressed in a mammalian cell.

* * * * *

SEQUENCE LISTING

```
<160> NUMBER OF SEQ ID NOS: 56

<210> SEQ ID NO 1
<211> LENGTH: 5340
<212> TYPE: DNA
<213> ORGANISM: Homo sapiens
<220> FEATURE:
<221> NAME/KEY: CDS
<222> LOCATION: (3022)...(3663)

<400> SEQUENCE: 1
```

```
ggatccctcg tggccagggt tcccttcaag gtgcttagcc aggtcaggag gccctagaga     60
agcatggttt ggattttctt tcccagacca aaaaagctcc aagttggttc tctcccagtt    120
tctaacttgc agttaaataa atcaggcaag gctggcctat gaggcagaca agtgtgaaga    180
aggagaagga ggaggagaag gagaaggaga aagaagaaga aggaggagaa gaagaagaag    240
aagaagaaga agaagaggag gaggaggagg aggaggagga agcagcagca gcagcagcag    300
cttgaatgga cagtggttcc ccttgcctag aaaatgggac cattatttct tttctaatct    360
gacccccaga ctcaggactt cctctatttt ctgcattttg ggtctcttg ttttgccttg     420
aaaaaaaatg ttttctccca aatcaaggag cagtagctgg tgcaagggaa aatctagggc    480
taggagtctt aagatatgac ttctatgtgg ttctgataga acttgctggg tgaccttgag    540
agagtcactc cccctctctg ggccttgatt ttttcatctt taaagaaggc ctcaaattcc    600
cattcttatg agaagaagac aagctcctag tgagtggtga cctaagggag cagctgcagc    660
aaaatgctaa cctgacagtc ccagatggtc cctttattgg ttctgaccct ggtctcaggc    720
ttcatttccc cacagcaagg gaaggagcct gctcacagag caccagctaa gatcagcagg    780
accgcgccac acccccgccc agtcctagag ccccccctctc gctggttcct gagcatacca   840
ccctcttcct tggaggaaaa tttgccccca agcagcctag gcggtaagag gctatcacta    900
gggcagactc acagacctac ctcatcccct caccccaccc tacagtctcg aagtcgggtc    960
ctgtccccctc ctgcagtttc cgggagactc aggatatctg gacctgctag aaagagaagc  1020
cttcctcgcc taaggagact taaaccggga tacttaaacc tcccgcctcg gcgtcttcct   1080
ccaggcacga ccgggtcaag agagagaagc ggaagctgca acccctcact ctgagtgacc   1140
ggaagcagaa gaccacggga tgtcccaggc ggggacaaga ggaggggctg gggaagaaag   1200
gagggatgat gagttcagag tccctttgga aaggtttcca gagagcgcta ccagggacaa   1260
cccaaggggc tggggaagtc cctgccttgt gctctctgtg cgatgcccga gtgatgcaga   1320
ggcagggggc tggagcaggt gactgctggc agctgctgtc tgtctgtgat tggaccggag   1380
gactaagggg agaaaaagtt tatcagcttc tcccagtgcc tgcacgctgt ggtagttcaa   1440
aagacacgag gggggagggc acagcagctc tgcttcccag cgccttggga gactgaagtg   1500
aaaggaacgc ttgagcccag gagttcgaga ccatcctggg caacaaagca agaccgcccc   1560
tcaccccata caaaataaaa atacaaataa attagccggg cacagtggcg catgcctgta   1620
gtctcagcta ctgggaaggc tgaagtggga ggatagcttg agcccaggag atcaaggctg   1680
cagtgagctg tgattgcacc actgcagtcc agcctgggcg acagaaggag accgtttttt   1740
ggttttgttt gttcgtttaa aaaaaaaaag aagcaagagc tcactgtgaa ctcctggttc   1800
cttcctcccc tcctcacact tcccagaact cttcctgtca cggttcctgg ccagaacgct   1860
gggatactat ctacaagctg tagtaggctt gtagtaatgg aatgtccgct tgaggggtcc   1920
ccgcacagcc aaccccggcc tctggagtgg gatctatggg ggtggggttc taagcgcctc   1980
tggggagtgt gaggtagcat ctcagggtgt ggcagaggct cggacacccc caaaaggtct   2040
gtgaatggaa gggacatagg caggatctct ctcagtgatg tcccctgtct tccaggatga   2100
agagaggcag tgaaacacca ggagagcagg gcgtccttta gaattcctgg acccttctcc   2160
aggctgctag tcaggacaat gagctcgtgg ttgtctttgc cactatcttc ctgtgcgatt   2220
tcagacaagc cacctccctc actaagccta aatttcccca tgtgtaacgt gcaggcattg   2280
taccctagag gcatcaaagt cccctccagg acagatgcta aggaaagata ggctaggagc   2340
aaagccgtct gaggtggcct gaccagagcc acacgaggct cttctcactg ggcgaggctc   2400
```

-continued

```
tttgaggaac cgagagttgc tgggacccag cccgccctcg agagagcaaa cagagcggcg   2460

ctcccctccc ccgaccccgg ccctttgtcc ggaatccagc tgtgctgcgg gggaggagcg   2520

ggctcgcgtg gcgcggcccc agggccccgg cgctgattgg ccggtggcgc gggcagcagc   2580

cgggcaggca cgctcctggc ccgggcgaag cagataaagc gtgccaaggg gcacacgact   2640

tgctgctcag gaaatccctg cggtctcacc gccgcgcctc gagagagagc gtgacagagg   2700

cctcggaccc cattctctct tcttttctcc tttggggctg gggcaactcc caggcggggg   2760

cgcctgcagc tcagctgaac ttggcgacca gaagcccgct gagctcccca cggccctcgc   2820

tgctcatcgc tctctattct tttgcgccgg tagaaaggta atatttggag gcctccgagg   2880

gacgggcagg ggaaagaggg atcctctgac ccagcggggg ctgggaggat ggctgttttt   2940

gtttttttccc acctagcctc ggaatcgcgg actgcgccgt gacggactca aacttaccct   3000

tccctctgac ccgccgtag g atg acg cct caa ccc tcg ggt gcg ccc act      3051
                       Met Thr Pro Gln Pro Ser Gly Ala Pro Thr
                        1               5                  10

gtc caa gtg acc cgt gag acg gag cgg tcc ttc ccc aga gcc tcg gaa     3099
Val Gln Val Thr Arg Glu Thr Glu Arg Ser Phe Pro Arg Ala Ser Glu
                15                  20                  25

gac gaa gtg acc tgc ccc acg tcc gcc ccg ccc agc ccc act cgc aca     3147
Asp Glu Val Thr Cys Pro Thr Ser Ala Pro Pro Ser Pro Thr Arg Thr
            30                  35                  40

cgg ggg aac tgc gca gag gcg gaa gag gga ggc tgc cga ggg gcc ccg     3195
Arg Gly Asn Cys Ala Glu Ala Glu Glu Gly Gly Cys Arg Gly Ala Pro
        45                  50                  55

agg aag ctc cgg gca cgg cgc ggg gga cgc agc cgg cct aag agc gag     3243
Arg Lys Leu Arg Ala Arg Arg Gly Gly Arg Ser Arg Pro Lys Ser Glu
    60                  65                  70

ttg gca ctg agc aag cag cga cgg agt cgg cga aag aag gcc aac gac     3291
Leu Ala Leu Ser Lys Gln Arg Arg Ser Arg Arg Lys Lys Ala Asn Asp
 75                  80                  85                  90

cgc gag cgc aat cga atg cac aac ctc aac tcg gca ctg gac gcc ctg     3339
Arg Glu Arg Asn Arg Met His Asn Leu Asn Ser Ala Leu Asp Ala Leu
                95                  100                 105

cgc ggt gtc ctg ccc acc ttc cca gac gac gcg aag ctc acc aag atc     3387
Arg Gly Val Leu Pro Thr Phe Pro Asp Asp Ala Lys Leu Thr Lys Ile
            110                 115                 120

gag acg ctg cgc ttc gcc cac aac tac atc tgg gcg ctg act caa acg     3435
Glu Thr Leu Arg Phe Ala His Asn Tyr Ile Trp Ala Leu Thr Gln Thr
        125                 130                 135

ctg cgc ata gcg gac cac agc ttg tac gcg ctg gag ccg ccg gcg ccg     3483
Leu Arg Ile Ala Asp His Ser Leu Tyr Ala Leu Glu Pro Pro Ala Pro
    140                 145                 150

cac tgc ggg gag ctg ggc agc cca ggc ggt tcc ccc ggg gac tgg ggg     3531
His Cys Gly Glu Leu Gly Ser Pro Gly Gly Ser Pro Gly Asp Trp Gly
155                 160                 165                 170

tcc ctc tac tcc cca gtc tcc cag gct ggc agc ctg agt ccc gcc gcg     3579
Ser Leu Tyr Ser Pro Val Ser Gln Ala Gly Ser Leu Ser Pro Ala Ala
                175                 180                 185

tcg ctg gag gag cga ccc ggg ctg ctg ggg gcc acc tct tcc gcc tgc     3627
Ser Leu Glu Glu Arg Pro Gly Leu Leu Gly Ala Thr Ser Ser Ala Cys
            190                 195                 200

ttg agc cca ggc agt ctg gct ttc tca gat ttt ctg tgaaaggacc          3673
Leu Ser Pro Gly Ser Leu Ala Phe Ser Asp Phe Leu
        205                 210

tgtctgtcgc tgggctgtgg gtgctaaggg taagggagag ggagggagcc gggagccgta   3733

gagggtggcc gacggcggcg gccctcaaaa gcacttgttc cttctgcttc tccctggctg   3793
```

acccctggcc ggcccaggct ccacgggggc ggcaggctgg gttcattccc cggccctccg 3853 agccgcgcca acgcacgcaa cccttgctgc tgcccgcgcg aagtgggcat tgcaaagtgc 3913 gctcatttta ggcctcctct ctgccaccac cccataatct cattcaaaga atactagaat 3973 ggtagcacta cccggccgga gccgcccacc gtcttgggtc gccctaccct cactcaagtc 4033 tgtctgcctc tcagtctctt accacccctc ctccaatgtg attcaatcca atgtttggtc 4093 tctcagcgct tactcccctt gccttgctcc aaagacgctg ccgatctgct ctactcccaa 4153 tcaggtccgg gatttcaggg cgcctcactc tgccttaaag ccacgaaggc gaccctctgc 4213 cttctcctcg tgcacttttc ggagccattg ccctcccggg gcggaagacc aggctgtgaa 4273 ctgggaaagc gctagcccgg ccagggagca tctccccagc ctccctgcga actgcgcctg 4333 aaacgtgagc tgcgctgcag gtgcctggag caccgcgcat cttttttttt taaatctgtt 4393 tgtaaattat atgatgcctt ttgaaatcaa ttttggtaca gtaaaattat atggcccctc 4453 ccctgtttta cacatttgta tttattaatg agatttcaca gcagggaaaa gcctatattt 4513 tggatattag attatttagg gattgctgga tgacatttaa gccaataaaa aaaaatggac 4573 cttcaagaag ccttggcaag atgactccat tgtgtgttgg ggagaggagg gccacagtca 4633 ctacagctga ggaagagcac ttctgtccaa agagagggat gacactcttt ctggaggtct 4693 gggctagagc cagggcagat tgggtttgga gagctggaag tcttctaagt aattattggt 4753 ccagctccct tttttctata tagggcaatg actcctctta tttcaaagag tggtttagaa 4813 gaaagacaag cctccaacta ggacaactga ctctcacttg ctggcccttt ccccaactcc 4873 accagcctag ctttagagca actgttggtt gcacttgggg aagggataca gtaataattc 4933 aattgcagag tcagagtcct cggaaacacg gctgggctgg gcatcctagg aatttcccca 4993 aggtgcttag aggcctagca aatcccctga gcatatttta ctccccaggc actgaggtgg 5053 ctgtgtcgtg aactccttga actgagcagc caggagcaaa gaaggtggag cgtctggctg 5113 gaatatccag caacgccccc tccctcatca cctggcagcc ttgattgaaa acttattaag 5173 aaactgttca aggtttccag ccacaccatg tctcttactg gcaaggtgga ataggactgg 5233 tgcagcatga gcactgaaat ctgtcccagg agtgccagta gagcaccact acatgacttc 5293 agggacccct aggacctcag agaatatggt ctaagctgta aggatcc 5340

<210> SEQ ID NO 2
<211> LENGTH: 214
<212> TYPE: PRT
<213> ORGANISM: Homo sapiens

<400> SEQUENCE: 2

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

```
Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Ser Ser Ala Cys Leu Ser Pro Gly Ser Leu
        195                 200                 205

Ala Phe Ser Asp Phe Leu
    210


<210> SEQ ID NO 3
<211> LENGTH: 1861
<212> TYPE: DNA
<213> ORGANISM: Mus musculis
<220> FEATURE:
<221> NAME/KEY: CDS
<222> LOCATION: (1093)...(1734)

<400> SEQUENCE: 3

ggatcccaag gtgatattga acctggccaa gcaatagttt ctgagtagaa aggacttgag      60

cagggaccgt ctctggtcac tctgtcctct ttcccaggat ggagtcagtc tgtgaaacat     120

ggttgcacac acatttcctg acccaaccca tagtggcgga gagctggata gcactttgaa     180

ctaatgggcg ctcctcccag ctgccagcca agaagacact tgactccttg atcgctggtt     240

catttagaca agccgtttcc ctctctgagc caaaagaccc catgtgtaat actcaaagaa     300

gaggccttcc ttatatatat ataggcaccc ccaaacctcc ttcatgctac caagaaaggg     360

tctggacaca tgccaaaaag aaagaggaaa aggcaaagct ctccccagcg gccggacggg     420

actcttctgg ctgggcgagg ctctttgagg aaccgagagt tgctgggact gagcccgcga     480

cgggggaggc gtggagtggg ggaacaaaca gagtgctgct cccctccccc gacccctgcc     540

ctttgtccgg aatccagctg tgctctgcgg gtgggggttg tgggggggagg agcgggctcg     600

cgtggcgcag cccctgggcc ccctccgctg attggcccgt ggtgcaggca gcagcccggc     660

aggcacgctc ctggccgggg gcagagcaga taaagcgtgc caggggacac acgacttgca     720

tgcagctcag aaatccctct gggtctcatc actgcagcag tggtcgagta cctcctcgga     780

gcttttctac gacttccaga cgcaatttac tccaggcgag ggcgcctgca gtttagcaga     840

acttcagagg gagcagagag gctcagctat ccactgctgc ttgacactga ccctatccac     900

tgctgcttgt cactgactga cctgctgctc tctattcttt tgagtcggga gaactaggta     960

acaattcgga aactccaaag ggtggatgag ggcgcgcgg ggtgtgtgtg ggggatactc    1020

tggtcccccg tgcagtgacc tctaagtcag aggctggcac acacacacct tccatttttt    1080

cccaaccgca gg atg gcg cct cat ccc ttg gat gcg ctc acc atc caa gtg    1131
              Met Ala Pro His Pro Leu Asp Ala Leu Thr Ile Gln Val
               1               5                  10

tcc cca gag aca caa caa cct ttt ccc gga gcc tcg gac cac gaa gtg     1179
Ser Pro Glu Thr Gln Gln Pro Phe Pro Gly Ala Ser Asp His Glu Val
     15                  20                  25

ctc agt tcc aat tcc acc cca cct agc ccc act ctc ata cct agg gac     1227
Leu Ser Ser Asn Ser Thr Pro Pro Ser Pro Thr Leu Ile Pro Arg Asp
 30                  35                  40                  45
```

```
tgc tcc gaa gca gaa gtg ggt gac tgc cga ggg acc tcg agg aag ctc      1275
Cys Ser Glu Ala Glu Val Gly Asp Cys Arg Gly Thr Ser Arg Lys Leu
                 50                  55                  60

cgc gcc cga cgc gga ggg cgc aac agg ccc aag agc gag ttg gca ctc      1323
Arg Ala Arg Arg Gly Gly Arg Asn Arg Pro Lys Ser Glu Leu Ala Leu
             65                  70                  75

agc aaa cag cga aga agc cgg cgc aag aag gcc aat gat cgg gag cgc      1371
Ser Lys Gln Arg Arg Ser Arg Arg Lys Lys Ala Asn Asp Arg Glu Arg
         80                  85                  90

aat cgc atg cac aac ctc aac tcg gcg ctg gat gcg ctg cgc ggt gtc      1419
Asn Arg Met His Asn Leu Asn Ser Ala Leu Asp Ala Leu Arg Gly Val
     95                 100                 105

ctg ccc acc ttc ccg gat gac gcc aaa ctt aca aag atc gag acc ctg      1467
Leu Pro Thr Phe Pro Asp Asp Ala Lys Leu Thr Lys Ile Glu Thr Leu
110                 115                 120                 125

cgc ttc gcc cac aac tac atc tgg gca ctg act cag acg ctg cgc ata      1515
Arg Phe Ala His Asn Tyr Ile Trp Ala Leu Thr Gln Thr Leu Arg Ile
                130                 135                 140

gcg gac cac agc ttc tat ggc ccg gag ccc cct gtg ccc tgt gga gag      1563
Ala Asp His Ser Phe Tyr Gly Pro Glu Pro Pro Val Pro Cys Gly Glu
            145                 150                 155

ctg ggg agc ccc gga ggt ggc tcc aac ggg gac tgg ggc tct atc tac      1611
Leu Gly Ser Pro Gly Gly Gly Ser Asn Gly Asp Trp Gly Ser Ile Tyr
        160                 165                 170

tcc cca gtc tcc caa gcg ggt aac ctg agc ccc acg gcc tca ttg gag      1659
Ser Pro Val Ser Gln Ala Gly Asn Leu Ser Pro Thr Ala Ser Leu Glu
    175                 180                 185

gaa ttc cct ggc ctg cag gtg ccc agc tcc cca tcc tat ctg ctc ccg      1707
Glu Phe Pro Gly Leu Gln Val Pro Ser Ser Pro Ser Tyr Leu Leu Pro
190                 195                 200                 205

gga gca ctg gtg ttc tca gac ttc ttg tgaagagacc tgtctggctc            1754
Gly Ala Leu Val Phe Ser Asp Phe Leu
                210

tgggtggtgg gtgctagtgg aaagggaggg gaccagagcc gtctggagtg ggaggtagtg   1814

gaggctctca agcatctcgc ctcttctggc tttcactact tggatcc                  1861


<210> SEQ ID NO 4
<211> LENGTH: 214
<212> TYPE: PRT
<213> ORGANISM: Mus musculis

<400> SEQUENCE: 4

Met Ala Pro His Pro Leu Asp Ala Leu Thr Ile Gln Val Ser Pro Glu
 1               5                  10                  15

Thr Gln Gln Pro Phe Pro Gly Ala Ser Asp His Glu Val Leu Ser Ser
            20                  25                  30

Asn Ser Thr Pro Pro Ser Pro Thr Leu Ile Pro Arg Asp Cys Ser Glu
        35                  40                  45

Ala Glu Val Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125
```

```
His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210


<210> SEQ ID NO 5
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 5

tggagaactg tcaaagcgat ctg                                               23


<210> SEQ ID NO 6
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 6

cacatgccca gtttctattg gtc                                               23


<210> SEQ ID NO 7
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 7

atcctgcggt tgggaa                                                       16


<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8

tggaaggtgt gtgtgtgcca g                                                 21


<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9

gatctagaga cttagaggtc actgc                                             25
```

<210> SEQ ID NO 10
<211> LENGTH: 30
<212> TYPE: DNA
<213> ORGANISM: Artificial Sequence
<220> FEATURE:
<223> OTHER INFORMATION: H3-1

<400> SEQUENCE: 10
gatctctcga gagagcaaac agcgcggcgg 30

<210> SEQ ID NO 11
<211> LENGTH: 31
<212> TYPE: DNA
<213> ORGANISM: Artificial Sequence
<220> FEATURE:
<223> OTHER INFORMATION: H3-2

<400> SEQUENCE: 11
ttattattat tttagcaaac actggagaca g 31

<210> SEQ ID NO 12
<211> LENGTH: 34
<212> TYPE: DNA
<213> ORGANISM: Artificial Sequence
<220> FEATURE:
<223> OTHER INFORMATION: H1

<400> SEQUENCE: 12
atctcttgta attatttatt aaacgaaatc tatt 34

<210> SEQ ID NO 13
<211> LENGTH: 34
<212> TYPE: DNA
<213> ORGANISM: Artificial Sequence
<220> FEATURE:
<223> OTHER INFORMATION: H2

<400> SEQUENCE: 13
ttaaacgaaa tctatttatt attattttag caaa 34

<210> SEQ ID NO 14
<211> LENGTH: 26
<212> TYPE: DNA
<213> ORGANISM: Artificial Sequence
<220> FEATURE:
<223> OTHER INFORMATION: H1P

<400> SEQUENCE: 14
gatctcgcca cgagccacaa ggattg 26

<210> SEQ ID NO 15
<211> LENGTH: 30
<212> TYPE: DNA
<213> ORGANISM: Artificial Sequence
<220> FEATURE:
<223> OTHER INFORMATION: E1

<400> SEQUENCE: 15
gatctaaatt tccccatgtg taacgtgcag 30

<210> SEQ ID NO 16
<211> LENGTH: 32
<212> TYPE: DNA
<213> ORGANISM: Artificial Sequence
<220> FEATURE:
<223> OTHER INFORMATION: N1

<400> SEQUENCE: 16
gatctggagc gggctcgcgt ggcgcggccc cg 32

<210> SEQ ID NO 17
<211> LENGTH: 31
<212> TYPE: DNA
<213> ORGANISM: Artificial Sequence
<220> FEATURE:
<223> OTHER INFORMATION: N2

<400> SEQUENCE: 17
gatctgccgg gcaggcacgc tcctggcccg g 31

<210> SEQ ID NO 18
<211> LENGTH: 31
<212> TYPE: DNA
<213> ORGANISM: Artificial Sequence
<220> FEATURE:
<223> OTHER INFORMATION: N3/4

<400> SEQUENCE: 18
gatctaaagc gtgccaaggg gcacacgact g 31

<210> SEQ ID NO 19
<211> LENGTH: 75
<212> TYPE: DNA
<213> ORGANISM: Homo sapiens

<400> SEQUENCE: 19
cttgtaatta tttattaaac gaaatctatt tattattatt ttagcaaaca ctggagacag 60
gtggggcttt ctttt 75

<210> SEQ ID NO 20
<211> LENGTH: 1665
<212> TYPE: DNA
<213> ORGANISM: Homo sapiens

<400> SEQUENCE: 20
cacacgagct gatctgatcg ccggcgacat cactcaggag accggccggg cgcgtggccc 60
ctgcaggcga ggcgaggagg ccaggccaag ttctccgtgc gcccctgcac ccttccaggc 120
tctcgcaccc gcaactggca cagagtaaca accccaggct gttgggaacg taagtgcgcc 180
ctggcggctc tgccctcagt ccgggctgca gcgctctgag cgcctttcta tctgtccgtc 240
ggtcctgcac agcgcaacga tgccagcccg ccttgagacc tgcatctccg acctcgactg 300
cgccagcagc agcggcagtg acctatccgg cttcctcacc gacgaggaag actgtgccag 360
actccaacag gcagcctccg cttcggggcc gcccgcgccg gcccgcaggg gcgcgcccaa 420
tatctcccgg gcgtctgagg ttccaggggc acaggacgac gagcaggaga ggcggcggcg 480
ccgcggccgg acgcgggtcc gctccgaggc gctgctgcac tcgctgcgca ggagccggcg 540
cgtcaaggcc aacgatcgcg agcgcaaccg catgcacaac ttgaacgcgg ccctggacgc 600
actgcgcagc gtgctgccct cgttccccga cgacaccaag ctcaccaaaa tcgagacgct 660
gcgcttcgcc tacaactaca tctgggctct ggccgagaca ctgcgcctgg cggatcaagg 720
gctgcccgga ggcggtgccc gggagcgcct cctgccgccg cagtgcgtcc cctgcctgcc 780
cggtccccca agccccgcca gcgacgcgga gtcctggggc tcaggtgccg ccgccgcctc 840
cccgctctct gaccccagta gcccagccgc ctccgaagac ttcacctacc gccccggcga 900
ccctgttttc tccttcccaa gcctgcccaa agacttgctc cacacaacgc cctgtttcat 960
tccttaccac taggcccttt gtagacactg ttactttccc cctcccctag tcagcaggca 1020

```
atagatgggg ccccagctgc cgcctcggga ccccctctcc aggcggaggg aggaagcggg   1080

agctttaaag cagtcgggga tacctgagcc gcttgttagg tcgccgcacc ctcgcggcgg   1140

atgtctcttg gtctgtttct ccggccctca gcccagcgcc cctcctgccc gcccctagac   1200

ggcctttcct tttgcacttt ctgaactcca caaaacctcc tttgtgactg gctcagaact   1260

gaccccagcc accacttcag tgtgatttag aaaagggaca gatcagcccc tgaagacgag   1320

gtgaaaagtc aattttacaa tttgtagaac tctaatgaag aaaaacgagc atgaaaattc   1380

ggtttgagcc ggctgacaat acaatgaaaa ggcttaaaaa gcagagacaa ggagtgggct   1440

tcatgcatta tggatcccga cccccaccac tgcagactcg ctctaggaag aactggagac   1500

tcttgcttag ctattcaggc acagggctgg agagtacttt aatttattca agatgcttca   1560

ttcatatgaa aatgtatttt tgtacataaa gagtttattc tattatgagc tatcaaagtt   1620

tacatttttg tactgcagac gcttcatgta aataaaaact aaaaa                    1665
```

<210> SEQ ID NO 21
<211> LENGTH: 237
<212> TYPE: PRT
<213> ORGANISM: Homo sapiens

<400> SEQUENCE: 21

```
Met Pro Ala Arg Leu Glu Thr Cys Ile Ser Asp Leu Asp Cys Ala Ser
 1               5                  10                  15

Ser Ser Gly Ser Asp Leu Ser Gly Phe Leu Thr Asp Glu Glu Asp Cys
            20                  25                  30

Ala Arg Leu Gln Gln Ala Ala Ser Ala Ser Gly Pro Pro Ala Pro Ala
        35                  40                  45

Arg Arg Gly Ala Pro Asn Ile Ser Arg Ala Ser Glu Val Pro Gly Ala
    50                  55                  60

Gln Asp Asp Glu Gln Glu Arg Arg Arg Arg Arg Gly Arg Thr Arg Val
65                  70                  75                  80

Arg Ser Glu Ala Leu Leu His Ser Leu Arg Arg Ser Arg Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Asp Thr Lys Leu
        115                 120                 125

Thr Lys Ile Glu Thr Leu Arg Phe Ala Tyr Asn Tyr Ile Trp Ala Leu
    130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235
```

<210> SEQ ID NO 22
<211> LENGTH: 714
<212> TYPE: DNA

<213> ORGANISM: Homo sapiens

<400> SEQUENCE: 22

```
atgccagccc gccttgagac ctgcatctcc gacctcgact gcgccagcag cagcggcagt      60

gacctatccg gcttcctcac cgacgaggaa gactgtgcca gactccaaca ggcagcctcc     120

gcttcggggc cgcccgcgcc ggcccgcagg agcgcgccca atatctcccg ggcgtctgag     180

gttccagggg cacaggacga cgagcaggag aggcggcggc gccgcggccg gacgcgggtc     240

cgctccgagg cgctgctgca ctcgctgcgc aggagccggc gcgtcaaggc caacgatcgc     300

gagcgcaacc gcatgcacaa cttgaacgcg gccctggacg cactgcgcag cgtgctgccc     360

tcgttccccg acgacaccaa gctcaccaaa atcgagacgc tgcgcttcgc ctacaactac     420

atctgggctc tggccgagac actgcgcctg gcggatcaag ggctgcccgg aggcggtgcc     480

cgggagcgcc tcctgccgcc gcagtgcgtc ccctgcctgc ccggtccccc aagccccgcc     540

agcgacgcgg agtcctgggg ctcaggtgcc gccgccgcct ccccgctctc tgaccccagt     600

agcccagccg cctccgaaga cttcacctac cgccccggcg accctgtttt ctccttccca     660

agcctgccca aagacttgct ccacacaacg ccctgtttca ttccttacca ctag           714
```

<210> SEQ ID NO 23
<211> LENGTH: 237
<212> TYPE: PRT
<213> ORGANISM: Homo sapiens

<400> SEQUENCE: 23

```
Met Pro Ala Arg Leu Glu Thr Cys Ile Ser Asp Leu Asp Cys Ala Ser
1               5                   10                  15

Ser Ser Gly Ser Asp Leu Ser Gly Phe Leu Thr Asp Glu Glu Asp Cys
            20                  25                  30

Ala Arg Leu Gln Gln Ala Ala Ser Ala Ser Gly Pro Pro Ala Pro Ala
        35                  40                  45

Arg Arg Ser Ala Pro Asn Ile Ser Arg Ala Ser Glu Val Pro Gly Ala
    50                  55                  60

Gln Asp Asp Glu Gln Glu Arg Arg Arg Arg Arg Gly Arg Thr Arg Val
65                  70                  75                  80

Arg Ser Glu Ala Leu Leu His Ser Leu Arg Arg Ser Arg Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Asp Thr Lys Leu
        115                 120                 125

Thr Lys Ile Glu Thr Leu Arg Phe Ala Tyr Asn Tyr Ile Trp Ala Leu
    130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235
```

<210> SEQ ID NO 24
<211> LENGTH: 6123
<212> TYPE: DNA
<213> ORGANISM: Homo sapiens

<400> SEQUENCE: 24

```
ggcctccccc gccttggcgg ccctgacccc gctgtcatcc agcgccgacg aagaagagga     60
ggaggagccg ggcgcgtcag gcggggcgcg tcggcagcgc ggggctgagg ccgggcaggg    120
ggcgcggggc ggcgtggctg cgggtgcgga gggctgccgg cccgcacggc tgctgggtct    180
ggtacacgat tgcaaacggc gcccttcccg ggcgcgggcc gtctcccgag gcgccaagac    240
ggccgagacg gtgcagcgca tcaagaagac ccgtagactg aaggccaaca accgcgagcg    300
aaaccgcatg cacaacctca acgcggcact ggacgcgctg cgcgaggtgc tccccacgtt    360
ccccgaggac gccaagctca ccaagatcga gaccctgcgc ttcgcccaca actacatctg    420
ggcactcacc gagaccctgc gcctggcgga tcactgcggg ggcggcggcg gggcctgcc     480
gggggcgctc ttctccgagg cagtgttgct gagcccggga ggagccagcg ccgccctgag    540
cagcagcgga gacagcccct cgcccgcctc cacgtggagt tgcaccaaca gccccgcgcc    600
gtcctcctcc gtgtcctcca attccacctc cccctacagc tgcactttat cgcccgccag    660
cccggccggg tcagacatgg actattggca gcccccacct cccgacaagc accgctatgc    720
acctcacctc cccatagcca gggattgtat ctagagctgc catttctgct acccacgcca    780
ggccttagtg ggttcccttt cctgtcccca gtcgagccct cctcccttcc cctgcccctc    840
ctttccacgc cctggaaacc atctcacttc acagggcagg tgtagccttt ctgattcctc    900
ggttgtttct tgcatttctt ggctttgggt atccttcatt cagacgggct ctgatttact    960
gaaggtgtga tggagcttat tgtcaaagcc aagggtggcg ttttgggggc gcttcttgag   1020
acgaaaaaga ccctgggaag agatgatggt ggcatatcta aagagtttgc agagcggact   1080
gacgctcctc ccctttctct ttaacgccga aggacttggt gcagttcgtg tgaatctcac   1140
agggggaatg caactggttc ctgtgatctc ttcacctttg cttctacata gagatgttaa   1200
tgtcgagtag aaagaaatgt atcttagcat ctgaatgatt ttgctggtaa taatattatc   1260
cacagatttg caatggctgg catctgcttt attcccattg ctgtctgcag gctgtgggaa   1320
tttcacctgt caaaccaaac ttccctctct gatgtgcact ttgttctgtt tcccagattc   1380
gtcacaatgc ctattgtcct gtccttctct ttcctttttc ttccccattt tgccatctgt   1440
ctcttatgat ttataagggg aaaaaaactt gttttgttag aggggcaggt tagaagtcat   1500
tgtataattt gtaggctttg taatgattga atgcaagcgt ggaaatttag gctgaactct   1560
ctatcaaaag gaaaaatgtg gaggaaaagg gaaaaatcag gagggaggat tgcctcatgt   1620
attatttatt tcgacctttt aggggagaag gaactccccc attctttcaa gagattaaaa   1680
ataaatcaac agtctgaaaa cctaagcaga cacggagcat tatccggatc agccacacac   1740
gtgttccctt ctatttatta taaagaaatt tttcatggga aaatatgtat tttttgtata   1800
ttctacagag tttattctag tatgtattta catcttgaag aacaagaaag ttgttcttgt   1860
gattaaacta taaataaact atctaatttt cataagtttg tgtgttgtat tctacctttt   1920
tcttgcttat gtgattttta gatgccaaat gagttgtgtt tttttgaaat tcttcccatg   1980
tcaaattgaa tatagtactt gtatttttgg gcaatgcttt gtgtagaata tcactaagaa   2040
atcacaaaaa gctgaatcat atttgagaca ctaatattga aaataagagt gtaactttct   2100
atttttaaga taaacacaca atttatttct aagaataaat ttctgagcaa acaagataag   2160
```

```
caaaaaaggg gagaagaatt taaatgataa ttaagtcatg ataagctcca agttcagaaa   2220
accttgattt gaaaaaaagt gaagttgaaa tttcttggtg gagtgtgtag aaatttgttt   2280
tttgtgcaac tcgtttggct tcaattctca tctgtaaact gaagggattg gacatgacct   2340
ccaagggtgc tccctttcca gctctaacat ctgtgatgta acagtacgta taaattcatt   2400
attagaagca gatttcctat taggcatttt aacaagctag ttgcttttaa aagcagactc   2460
ccagaataaa gcagatattt agagtgaact ggaattgaaa atatatacag aaatagctcc   2520
gctttcccaa tatttgttaa agcaattaca tagtcaaaac ttcttcaaag agaaagcaaa   2580
aatggtttaa cttgcacctc aatctccaaa gcagaaatga atgacctttg attggctttg   2640
ggtcaaaaat gaccaaatga aggttgacca cattctatgc ttaatcccct tggggaagag   2700
tgtctatgac aacacaagct aaaaaatatc acattaaaac ttggtcgttc acagcaccca   2760
cctccccacg aatgtcttac ctgcatctgg ttgggctaaa actccactct tctgcacaat   2820
gcaataataa tttctcctga ggtgtctatc tgaaaccact cctctctaat aactccattt   2880
taatcaaagg aagaactaac tcagggtttt tgtttcattt tttatagcca agcatgagat   2940
accttttggt aaatcccttt taatttaaag attgtgttac tcttagctgc tctttgatta   3000
tctgacatgg ggagaaagtg atatttctct tatattcaca tttatgtttc taatgtttaa   3060
aaagccaagc cagcaagcaa aggaattgta atatgatagt ttgaaaacat cagttttggt   3120
gctgaacaat gcttcttctg gtgatacatt tgatgataca tggtgcttct tttggaaact   3180
tgccaaagaa atagttcatg acaaaatctc agatgcagct actcctccaa ctatgggaaa   3240
ccttctcaat tggtgaagcc atcccataaa aagatgaccc taatggctaa ggtggagagg   3300
cagggatgga tagatgattc aataatccta gctctgagca agactaatac agctaataca   3360
gacttcactc ttgacctagc ggactctaca cacttcttcc aggtccagag tcttgttcaa   3420
gttctcaaag ctggagcttg caggtcccca ttacacacaa gcagatatat cctaagtgcc   3480
cgggctttca tctgccattt gcaattcaca ctcaggcttt cccttcccca tctagaacac   3540
accttatttt acactaaatt ggcgcaatta ttttttatgg catctaatca tcttaagcgg   3600
gtaagaatgg tgttctgact gcctcagcgc cgagattctc tcccctaatc cgttgcaacc   3660
ttcacagccg gtggcctgag gcccagtcgt tctcttccct tcctagtagg aatgagtaca   3720
attagagggt caaagccgct gcttctgcag taggcaacaa ggtagtattt ccattttatt   3780
catttccctc ccgacattgt gaccgcgctg tgatgagctg catctgtgtg caccaagtag   3840
gtttgcaggc ctcggagcca cgccatttta tttctggtgg ctctggtgag agacacttca   3900
aacaacgctg tggagatttt cttccggtga cagacacaga ctctcagtgt tgctagatct   3960
ttccaacgcc agctagcgcg ctgcggcgcg ttttcctaag tgcggagagg cgcgaaggtg   4020
ggtcctgttc tcattggagc gtcgctttag cgcggccggc gttccgggac tggctgtatt   4080
tatttgttct aaagtgctca ggccttgtta cggctcattt ttccttcact agattttaaa   4140
tacatccatc tgagtgccaa gaaggaggaa aaaaaaagta gagaggcgga ctgccaaccg   4200
ctgggcccgc cacgggagcc ggacctaggc tcagccggag gcaggaggag gggctgaggc   4260
ttcccgggcc cgcagcacct ggaccagagc cggatgggcg ctcctggtgt cccagctgag   4320
gcgaaggccc tgggcggctt tggccaggag ggaggaagga cccattcggc acttcccaaa   4380
gcctagtccg atggcccagg aagggcgttt agacccaagg ccggcttcag ctgcccaccc   4440
gccagtctgg gtcacaggct gctaaagggc cgggcttgag ggcgaggctg ggagctgcgg   4500
cgcccccacc cgctgggtac accccctgc attgcacacc cttgagctgg ttgtgacttc    4560
```

```
tgggcaccga cacctggaac cggttaaaag cgcctcctcc tcaccgccag cctcggtctt   4620

ccccgagccc cctcgggctc ccaagcgagc tttgaatgta ttaattaaat aaagcgggca   4680

gctcttgaat cgcgccaatg cagtgcgctc ccgggagcgt gaaagtcccg gcctccgaat   4740

ctgcaaaaga aatgtgtgaa aagagaatta gtgaaattag gttagaccaa taaaacgtga   4800

gggctccaat accccccttt ctcgctcccc cagcctgggg ctagaagggc tatctggtct   4860

gatctattgt ttcctgccct ggcagggggt tcattgtgtg ataaataatt ccccctccat   4920

tttcttttat tcttaaaaaa aatgggtatt tgcataatca gtgctttgat gtggccagaa   4980

atcggaggtt tggtctcccc aagtctgcta ttggtagcga agcaacaaag ctagatccag   5040

atctttcact tcgctgacag tgtgtggggc agattgtcag aaatagcagc gttaagctgc   5100

tgccttcttt tttaaggacc actttaatga ttaaacttaa ggaatgtcca aaaaaggagg   5160

gatgaaagac cagctttctc atcactccac ggacacaccc cgcccccgc cccccccccc    5220

atgcttctta ttattctctg cagtttcttt tccaaagcgc ttggtttggg ggatggtgca   5280

tctcccttgg ggccgcccca cgtggcaccg agtgggcatc ggcaggggtc ccctagggcc   5340

aaggaggggc caggtctgca ggagcggttc tccttgcccc caacgcgttt ttccttcccc   5400

agtttgattt ttccagccgg gatggggttc atcttatgga ggacgttgaa gtgagtcgct   5460

ctttagtccc cgagtggaat gagtggggt tggggggttc cctgggaacg cagcttggag    5520

gcagtttcag atggtccccg acaggagagg cgagcaaaga aattcagtca tccggaaagc   5580

agaacgcgaa agccagtgtg gccggaccta ttatttccct gcaaggtggc gtgagtcggg   5640

aggatggaat ggggaagaat cctgatggtg tgtgcgttac aacaaacgac tttttttcccc  5700

ctctcggtgc cagggtcggg ggaggggaga caggggtggt tctgtctgct ttcgctagca   5760

ttctctgctt ctccagctgc tcagagcgcg aaggggggaaa tgccaacttg gattactgac  5820

tgagaacacc gcgtgaaagg ccaggcctcc ctgattaccc gggcaggcgc cggcttcgcg   5880

ctccagcctg gagaggtgtc aaccgcgtga gagatgctcg gcctcccggg atccaaattg   5940

gagatggaat cagagatgga agggggaaag gaggaggatc cttgaaacac ctgcacgccc   6000

acggtcccac tccttctcct cctcggcccc gcatctcacc gaactgaccc caggccattc   6060

ttcagatgtc ccagcagctt ttggatcgca gagcttcagc ggtagttagc tcatcgtgaa   6120

ttc                                                                 6123
```

<210> SEQ ID NO 25
<211> LENGTH: 250
<212> TYPE: PRT
<213> ORGANISM: Homo sapiens

<400> SEQUENCE: 25

```
Ala Ser Pro Ala Leu Ala Ala Leu Thr Pro Leu Ser Ser Ser Ala Asp
1               5                   10                  15

Glu Glu Glu Glu Glu Glu Pro Gly Ala Ser Gly Gly Ala Arg Arg Gln
            20                  25                  30

Arg Gly Ala Glu Ala Gly Gln Gly Ala Arg Gly Gly Val Ala Ala Gly
        35                  40                  45

Ala Glu Gly Cys Arg Pro Ala Arg Leu Leu Gly Leu Val His Asp Cys
    50                  55                  60

Lys Arg Arg Pro Ser Arg Ala Arg Ala Val Ser Arg Gly Ala Lys Thr
65                  70                  75                  80

Ala Glu Thr Val Gln Arg Ile Lys Lys Thr Arg Arg Leu Lys Ala Asn
                85                  90                  95
```

```
Asn Arg Glu Arg Asn Arg Met His Asn Leu Asn Ala Ala Leu Asp Ala
            100                 105                 110

Leu Arg Glu Val Leu Pro Thr Phe Pro Glu Asp Ala Lys Leu Thr Lys
        115                 120                 125

Ile Glu Thr Leu Arg Phe Ala His Asn Tyr Ile Trp Ala Leu Thr Glu
    130                 135                 140

Thr Leu Arg Leu Ala Asp His Cys Gly Gly Gly Gly Gly Gly Leu Pro
145                 150                 155                 160

Gly Ala Leu Phe Ser Glu Ala Val Leu Leu Ser Pro Gly Gly Ala Ser
                165                 170                 175

Ala Ala Leu Ser Ser Ser Gly Asp Ser Pro Ser Pro Ala Ser Thr Trp
            180                 185                 190

Ser Cys Thr Asn Ser Pro Ala Pro Ser Ser Ser Val Ser Ser Asn Ser
        195                 200                 205

Thr Ser Pro Tyr Ser Cys Thr Leu Ser Pro Ala Ser Pro Ala Gly Ser
    210                 215                 220

Asp Met Asp Tyr Trp Gln Pro Pro Pro Pro Asp Lys His Arg Tyr Ala
225                 230                 235                 240

Pro His Leu Pro Ile Ala Arg Asp Cys Ile
                245                 250
```

<210> SEQ ID NO 26
<211> LENGTH: 591
<212> TYPE: DNA
<213> ORGANISM: Homo sapiens

<400> SEQUENCE: 26

```
atgaacgtgg ggaaagtggg gagggctaac gagcaattga gaacaagttt cccccgaggt      60

ccagtagccc ttcagctctt ttttctcatt gaaaagcaga attgggaaga tgggcccctt     120

gtccctacaa cgccccccag cgcggagcag aggtcacaga aatgtcagcg cagcgcattt     180

gcttgcagga gcagcagctc tgccgctcct cccgctcgaa tctttgtcgc ggaggccgca     240

gtcccttctc ggggagggaa cgcaggaccg cccgcggagg gcaggacccg gctgactggc     300

agcagggtca cagcgagcgc tagcggcgct cctgaccttg tgttgctgag cccgggagga     360

gccagcgccg ccctgagcag cagcggagac agcccctcgc ccgcctccac gtggagttgc     420

accaacagcc ccgcgccgtc ctcctccgtg tcctccaatt ccacctcccc ctacagctgc     480

actttatcgc ccgccagccc ggccgggtca gacatggact attggcagcc cccacctccc     540

gacaagcacc gctatgcacc tcacctcccc atagccaggg attgtatcta g              591
```

<210> SEQ ID NO 27
<211> LENGTH: 196
<212> TYPE: PRT
<213> ORGANISM: Homo sapiens

<400> SEQUENCE: 27

```
Met Asn Val Gly Lys Val Gly Arg Ala Asn Glu Gln Leu Arg Thr Ser
 1               5                  10                  15

Phe Pro Arg Gly Pro Val Ala Leu Gln Leu Phe Phe Leu Ile Glu Lys
            20                  25                  30

Gln Asn Trp Glu Asp Gly Pro Leu Val Pro Thr Thr Pro Pro Ser Ala
        35                  40                  45

Glu Gln Arg Ser Gln Lys Cys Gln Arg Ser Ala Phe Ala Cys Arg Ser
    50                  55                  60

Ser Ser Ser Ala Ala Pro Pro Ala Arg Ile Phe Val Ala Glu Ala Ala
```

```
65                  70                  75                  80

Val Pro Ser Arg Gly Gly Asn Ala Gly Pro Pro Ala Glu Gly Arg Thr
                85                  90                  95

Arg Leu Thr Gly Ser Arg Val Thr Ala Ser Ala Ser Gly Ala Pro Asp
            100                 105                 110

Leu Val Leu Leu Ser Pro Gly Gly Ala Ser Ala Ala Leu Ser Ser Ser
        115                 120                 125

Gly Asp Ser Pro Ser Pro Ala Ser Thr Trp Ser Cys Thr Asn Ser Pro
    130                 135                 140

Ala Pro Ser Ser Ser Val Ser Ser Asn Ser Thr Ser Pro Tyr Ser Cys
145                 150                 155                 160

Thr Leu Ser Pro Ala Ser Pro Ala Gly Ser Asp Met Asp Tyr Trp Gln
                165                 170                 175

Pro Pro Pro Pro Asp Lys His Arg Tyr Ala Pro His Leu Pro Ile Ala
            180                 185                 190

Arg Asp Cys Ile
        195


<210> SEQ ID NO 28
<211> LENGTH: 2502
<212> TYPE: DNA
<213> ORGANISM: Homo sapiens

<400> SEQUENCE: 28

cggccacgac acgaggaatt cgcccacgca ggaggcacgg cgtccggagg ccccagggtt      60

atgagactat cactgctcag gacctactaa caacaaagga aatcgaaaca tgaccaaatc     120

gtacagcgag agtgggctga tgggcgagcc tcagccccaa ggtcctccaa gctggacaga     180

cgagtgtctc agttctcagg acgaggagca cgaggcagac aagaaggagg acgacctcga     240

agccatgaac gcagaggagg actcactgag gaacggggga gaggaggagg acgaagatga     300

ggacctggaa gaggaggaag aagaggaaga ggaggatgac gatcaaaagc ccaagagacg     360

cggcccccaaa aagaagaaga tgactaaggc tcgcctggag cgttttaaat tgagacgcat     420

gaaggctaac gcccgggagc ggaaccgcat gcacggactg aacgcggcgc tagacaacct     480

gcgcaaggtg gtgccttgct attctaagac gcagaagctg tccaaaatcg agactctgcg     540

cttggccaag aactacatct gggctctgtc ggagatcctg cgctcaggca aaagcccaga     600

cctggtctcc ttcgttcaga cgctttgcaa gggcttatcc caacccacca ccaacctggt     660

tgggggctgc ctgcaactca atcctcggac ttttctgcct gagcagaacc aggacatgcc     720

cccccacctg ccgacggcca gcgcttcctt ccctgtacac ccctactcct accagtcgcc     780

tgggctgccc agtccgcctt acggtaccat ggacagctcc catgtcttcc acgttaagcc     840

tccgccgcac gcctacagcg cagcgctgga gcccttcttt gaaagccctc tgactgattg     900

caccagccct tcctttgatg gacccctcag cccgccgctc agcatcaatg gcaacttctc     960

tttcaaacac gaaccgtccg ccgagtttga gaaaaattat gcctttacca tgcactatcc    1020

tgcagcgaca ctggcagggg cccaaagcca cggatcaatc ttctcaggca ccgctgcccc    1080

tcgctgcgag atccccatag acaatattat gtccttcgat agccattcac atcatgagcg    1140

agtcatgagt gcccagctca atgccatatt tcatgattag aggcacgcca gtttcaccat    1200

ttccgggaaa cgaacccact gtgcttacag tgactgtcgt gtttacaaaa ggcagccctt    1260

tgggtactac tgctgcaaag tgcaaatact ccaagcttca agtgatatat gtatttattg    1320

tcattactgc ctttggaaga aacaggggat caaagttcct gttcacctta tgtattattt    1380
```

```
tctatagctc ttctatttaa aaaataaaaa aatacagtaa agtttaaaaa atacaccacg   1440

aatttggtgt ggctgtattc agatcgtatt aattatctga tcgggataac aaaatcacaa   1500

gcaataatta ggatctatgc aatttttaaa ctagtaatgg gccaattaaa atatatataa   1560

atatatattt ttcaaccagc attttactac ttgttacctt tcccatgctg aattattttg   1620

ttgtgatttt gtacagaatt tttaatgact ttttataatg tggatttcct attttaaaac   1680

catgcagctt catcaatttt tatacatatc agaaaagtag aattatatct aatttataca   1740

aaataattta actaatttaa accagcagaa aagtgcttag aaagttattg tgttgcctta   1800

gcacttcttt cctctccaat tgtaaaaaaa aaaaaaaaaa aaaaaaaaaa aaaaaaattg   1860

cacaatttga gcaattcatt tcactttaaa gtctttccgt ctccctaaaa taaaaaccag   1920

aatcataatt ttcaagagga gaaaaaatta agagatacat tccctatcac aacatatcaa   1980

ttcaacacat tacttgcaca agcttgtata tacatattat aaatagatgc caacataccc   2040

ttctttaaat cacaagctgc ttgactatca catacaattt gcactgttac tttttagtct   2100

tttactcctt tgcattccat gattttacag agaatctgaa gctattgatg tttccagaaa   2160

atataaatgc atgattttat acatagtcac ccccatggtg ggttgtcata tattcatgta   2220

ataaatctga gcctaaatct aatcaggttg ttaatgttgg gagttatatc tatagtagtc   2280

aattagtaca gtagcttaaa taaattcccc ccatttaatt cataattaga acaatagcta   2340

ttgcatgtaa aatgcagtcc agaataagtg ctgtttgaga tgtgatgctg gtaccactgg   2400

aatcgatctg tactgtaatt ttgtttgtaa tcctgtatat tatggtgtaa tgcacaattt   2460

agaaaacatt catccagttg caataaaata gtattgaaag tg                      2502
```

<210> SEQ ID NO 29
<211> LENGTH: 356
<212> TYPE: PRT
<213> ORGANISM: Homo sapiens

<400> SEQUENCE: 29

```
Met Thr Lys Ser Tyr Ser Glu Ser Gly Leu Met Gly Glu Pro Gln Pro
 1               5                  10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Gly Gly Cys Leu Gln Leu Asn Pro
```

```
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355


<210> SEQ ID NO 30
<211> LENGTH: 2618
<212> TYPE: DNA
<213> ORGANISM: Homo sapiens

<400> SEQUENCE: 30

gcgcacagcc tggacgcgtg cgcaggcgtc aggcgcatag acctgctagc ccctcagcta      60

gcggccccgc ccgcgcttag catcactaac tgggctatat aacctgagcg cccgcgcggc     120

cacgacacga ggaattcgcc cacgcaggag gcgcggcgtc cggaggcccc agggttatga     180

gactatcact gctcaggacc tactaacaac aaaggaaatc gaaacatgac caaatcgtac     240

agcgagagtg ggctgatggg cgagcctcag ccccaaggtc ctccaagctg gacagacgag     300

tgtctcagtt ctcaggacga ggagcacgag gcagacaaga aggaggacga cctcgaaacc     360

atgaacgcag aggaggactc actgaggaac gggggagagg aggaggacga agatgaggac     420

ctggaagagg aggaagaaga ggaagaggag gatgacgatc aaaagcccaa gagacgcggc     480

cccaaaaaga agaagatgac taaggctcgc ctggagcgtt ttaaattgag acgcatgaag     540

gctaacgccc gggagcggaa ccgcatgcac ggactgaacg cggcgctaga caacctgcgc     600

aaggtggtgc cttgctattc taagacgcag aagctgtcca aaatcgagac tctgcgcttg     660

gccaagaact acatctgggc tctgtcggag atcctgcgct caggcaaaag cccagacctg     720

gtctccttcg ttcagacgct ttgcaagggc ttatcccaac ccaccaccaa cctggttgcg     780

ggctgcctgc aactcaatcc tcggactttt ctgcctgagc agaaccagga catgcccccc     840

cacctgccga cggccagcgc ttccttccct gtacacccct actcctacca gtcgcctggg     900

ctgcccagtc cgccttacgg taccatggac agctcccatg tcttccacgt taagcctccg     960

ccgcacgcct acagcgcagc gctggagccc ttctttgaaa gccctctgac tgattgcacc    1020

agcccttcct ttgatggacc cctcagcccg ccgctcagca tcaatggcaa cttctctttc    1080

aaacacgaac cgtccgccga gtttgagaaa aattatgcct ttaccatgca ctatcctgca    1140
```

```
gcgacactgg caggggccca aagccacgga tcaatcttct caggcaccgc tgcccctcgc   1200

tgcgagatcc ccatagacaa tattatgtcc ttcgatagcc attcacatca tgagcgagtc   1260

atgagtgccc agctcaatgc catatttcat gattagaggc acgccagttt caccatttcc   1320

gggaaacgaa cccactgtgc ttacagtgac tgtcgtgttt acaaaaggca gccctttggg   1380

tactactgct gcaaagtgca aatactccaa gcttcaagtg atatatgtat ttattgtcat   1440

tactgccttt ggaagaaaca ggggatcaaa gttcctgttc accttatgta ttattttcta   1500

tagctcttct atttaaaaaa taaaaaaata cagtaaagtt taaaaaatac accacgaatt   1560

tggtgtggct gtattcagat cgtattaatt atctgatcgg gataacaaaa tcacaagcaa   1620

taattaggat ctatgcaatt tttaaactag taatgggcca attaaaatat atataaatat   1680

atatttttca accagcattt tactacttgt tacctttccc atgctgaatt attttgttgt   1740

gattttgtac agaattttta atgacttttt ataatgtgga tttcctattt taaaaccatg   1800

cagcttcatc aatttttata catatcagaa aagtagaatt atatctaatt tatacaaaat   1860

aatttaacta atttaaacca gcagaaaagt gcttagaaag ttattgtgtt gccttagcac   1920

ttctttcctc tccaattgta aaaaaaaaaa aaaaaaaaaa aaaaaaaaaa aaattgcaca   1980

atttgagcaa ttcatttcac tttaaagtct ttccgtctcc ctaaaataaa aaccagaatc   2040

ataattttca agagaagaaa aaattaagag atacattccc tatcaaaaca tatcaattca   2100

acacattact tgcacaagct tgtatataca tattataaat aaatgccaac ataccccttct   2160

ttaaatcaaa agctgcttga ctatcacata caatttgcac tgttactttt tagtctttta   2220

ctcctttgca ttccatgatt ttacagagaa tctgaagcta ttgatgtttc cagaaaatat   2280

aaatgcatga ttttatacat agtcacaaaa atggtggttt gtcatatatt catgtaataa   2340

atctgagcct aaatctaatc aggttgttaa tgttgggatt tatatctata gtagtcaatt   2400

agtacagtag cttaaataaa ttcaaaccat ttaattcata attagaacaa tagctattgc   2460

atgtaaaatg cagtccagaa taagtgctgt ttgagatgtg atgctggtac cactggaatc   2520

gatctgtact gtaattttgt ttgtaatcct gtatattatg gtgtaatgca caatttagaa   2580

aacattcatc cagttgcaat aaaatagtat tgaaagtg                           2618
```

<210> SEQ ID NO 31
<211> LENGTH: 356
<212> TYPE: PRT
<213> ORGANISM: Homo sapiens

<400> SEQUENCE: 31

```
Met Thr Lys Ser Tyr Ser Glu Ser Gly Leu Met Gly Glu Pro Gln Pro
 1               5                  10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Thr Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110
```

```
Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355
```

<210> SEQ ID NO 32
<211> LENGTH: 1211
<212> TYPE: DNA
<213> ORGANISM: Homo sapiens

<400> SEQUENCE: 32

```
tttagggagt ggaagctgaa ggcgtatctg gcttttgaat atagcgtttt tctgcttttc      60

tttctgtttg cctctccctt gttgaatgta ggaaatcgaa acatgaccaa atcgtacagc     120

gagagtgggc tgatgggcga gcctcagccc caaggtcctc caagctggac agacgagtgt     180

ctcagttctc aggacgagga gcacgaggca gacaagaagg aggacgacct cgaagccatg     240

aacgcagagg aggactcact gaggaacggg ggagaggagg aggacgaaga tgaggacctg     300

gaagaggagg aagaagagga agaggaggat gacgatcaaa agcccaagag acgcggcccc     360

aaaaagaaga agatgactaa ggctcgcctg gagcgtttta aattgagacg catgaaggct     420

aacgcccggg agcggaaccg catgcacgga ctgaacgcgg cgctagacaa cctgcgcaag     480

gtggtgcctt gctattctaa gacgcagaag ctgtccaaaa tcgagactct gcgcttggcc     540

aagaactaca tctgggctct gtcggagatc ctgcgctcag gcaaaagccc agacctggtc     600

tccttcgttc agacgctttg caagggctta tcccaaccca ccaccaacct ggttgcgggc     660

tgcctgcaac tcaatcctcg gacttttctg cctgagcaga accaggacat gccccccac      720
```

```
ctgccgacgg ccagcgcttc cttccctgta cacccctact cctaccagtc gcctgggctg    780

cccagtccgc cttacggtac catggacagc tcccatgtct tccacgttaa gcctccgccg    840

cacgcctaca gcgcagcgct ggagcccttc tttgaaagcc ctctgactga ttgcaccagc    900

ccttcctttg atggacccct cagcccgccg ctcagcatca atggcaactt ctctttcaaa    960

cacgaaccgt ccgccgagtt tgagaaaaat tatgccttta ccatgcacta tcctgcagcg   1020

acactggcag gggcccaaag ccacggatca atcttctcag gcaccgctgc ccctcgctgc   1080

gagatcccca tagacaatat tatgtccttc gatagccatt cacatcatga gcgagtcatg   1140

agtgcccagc tcaatgccat atttcatgat tagaggcacg ccagtttcac catttccggg   1200

aaacgaaccc a                                                        1211
```

```
<210> SEQ ID NO 33
<211> LENGTH: 356
<212> TYPE: PRT
<213> ORGANISM: Homo sapiens

<400> SEQUENCE: 33

Met Thr Lys Ser Tyr Ser Glu Ser Gly Leu Met Gly Glu Pro Gln Pro
 1               5                  10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285
```

```
Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355


<210> SEQ ID NO 34
<211> LENGTH: 3906
<212> TYPE: DNA
<213> ORGANISM: Homo sapiens

<400> SEQUENCE: 34

tttatgttct ggattctgga aagaaggaaa aatatatctt tggactggta tatcagtcat      60

ttttgtataa aatattcatg agataaaaaa tctaagaata aaaacaggca ctaacactgc     120

aatgaataat caagtcaatt ttctttttct ataatatatt ttcttatact atgccataac     180

taaaggagta ttctgggaat ttctttcagt tttggactgg tcatttagaa tggaagactt     240

ggacaagata attacatata aaaaacttta gtttcaaata aaatcaggta ctcacaggaa     300

ttaacctttg atatttccct tttccagagt ctggaaatgt caaaaacttt tgtaaaatcc     360

aaggagatgg gagagctagt caacacacca tcctggatgg ataaaggtct gggctcccaa     420

aatgaggtga aggaggaaga gagcagacca ggtacttatg ggatgctcag cagcttaact     480

gaagagcatg acagtattga ggaagaagaa gaagaggaag aagatgggga gaaacctaag     540

agaaggggtc ccaagaaaaa gaagatgacc aaagctcgcc ttgagagatt cagggctcga     600

agagtcaagg ctaatgccag agaacggacc cggatgcatg gcctgaatga cgccctggat     660

aacctgaggc gagtcatgcc atgctactct aaaacccaaa aactttccaa gatagagact     720

cttagactgg ccaggaacta tatttgggct ttatctgaag tcctggagac tggccagaca     780

cctgaaggga aaggctttgt ggagatgctg tgtaaagggc tctctcagcc cacaagcaac     840

ctggtggctg gatgtctcca actgggccct cagtctgtcc tcctggagaa gcacgaggat     900

aaatctccta tttgtggctc tgccatctct gtccacaact tcaactatca gtctccgggg     960

cttcctagcc ctccttatgg tcatatggaa acacatctcc ttcatctcaa gccccaagta    1020

ttcaagagtt tgggagaatc gtcctttggg agccatctgc ctgactgcag tacaccccct    1080

tatgagggcc cactcactcc acccctgagc atcagtggga acttctcctt gaagcaagat    1140

gggtctcctg acctagaaaa atcctacagc ttcatgccac attacccttc ttcaagtcta    1200

agctcagggc atgtgcattc aactcctttt caggctggta ccccccgtta tgatgttcct    1260

atagacatgt cctatgattc ctacccccat catggtattg ggacccaact caatacagtc    1320

ttcactgagt gaggcagtta agttcaatgt ttcagagaat gacgtggaga cattttccat    1380

aattcaagtg gttgagctaa agattcaatg accttaaagg atccctatgg atatatatca    1440

aacaatagtt caagtccatt taggctttcc ttcacctatc acctcttttc tcatcacctt    1500

ctcacattgc attgatttct ttatagagtc ctcaagtgaa aatatttgat gatttaacaa    1560

ccatgtgaaa atagaacaga agacctgggg cctattccag tggtgccaaa aactcattgc    1620

ataatctgtg ccaattaatt ttccatttct ggcctttgtt tatttactag caattgtaaa    1680

taaacaaatt gtatttatat gaggcaacta ttctaagtcc agatgatttc taaagtcctt    1740
```

```
cacagttctg aaatgctata actgtggtga tcactcttga caatttcttg aaactgaaag   1800
aatagagaaa taataggaaa gggatgctat gcatagaatg atcaaattga attatcagag   1860
ggatcacaag gtacatgtct cttggctcac agaatgcaaa gcttgtttgg atttaatgat   1920
aggacctctt tgtatctatt gaaaaatagc ttctggaagc taaaagtcta acatggctgt   1980
cactgtgaag aacaaaacat gttcgttaag agactaactc tatttgttat tagactaaaa   2040
gttgaacata tcttccttat gatttgaaga accataatag agaaccataa tagaggcctc   2100
atgccaactt tattcttgat aatatttcaa aaccattttt ctcagtacta gaggtagggc   2160
aaacaagtca ctgaagcctc agactcctat aactaatggg acatagagaa gtcttttaga   2220
ccatgacctc cataaccaga gggctctgga acttctgatg aagctcaggt gctgctgtta   2280
gaatcagcac acaacacagg tttatattaa agagcaataa aatagctatt ggctataata   2340
actactatag ttcagggact ctctccagct cacagttgcc catgggaaaa acaatggatt   2400
ttttttaag caagatgaat ttcatttggt taaacgtgat taaaaccatc cacctctgtc   2460
cacaccaata tattttccag aagcacaagc accaatcaat ttattgatca aggttaaatt   2520
tttccaacat atatgtagtt ccttatctct cccccctacac taattgttac ctcttcctca   2580
cttctaagat agaatatgtt attatatatt gtaaataaca tttcaggtga ccaaacttaa   2640
ggatgcagaa atgaaatcca aggttggtga atatttttac caactatgtc ttcatcacag   2700
gtttaaccca atttgcagag tgtttatttt tctttatgta actccttttt cctttatatc   2760
aatgctaact tcatcaaatt tgtatttttt ttcagaaaat gggacctgag aaattttcct   2820
atcttgttca atcagccagg acagttattt aagtcaaacc agagcctgaa tggcttattt   2880
gatagtagat taggtcctgc tcctgccaga aaggataagt ttaacatgca gggtacatca   2940
atagggccaa tttaaaaaat gataacacat attagtatgt cattttctat agctcagcta   3000
tcccctaaaa tctgccaact atatgtgtat cttgtctgtt tacctctctt atttattatc   3060
tccatacagt ataagttatt ttttttccat tttgctctca gcacttaccc tgctgtattt   3120
tgcacccttg gtttgtaaat tcacttgaaa gtagccttgc agagagatct taagccccat   3180
cagtcaccaa agtggttccc ttcatcacaa tctgccctag aggaaatagg caagtaaaat   3240
gatatataaa gccatactat gtgctttctg agtatatact gcacttacct ttgtgagcgg   3300
ctgtaggagg gtctatcctc gaagctagca ttttctggca tttaagtttg tgataatcac   3360
tgttgtttga gttatttatt agatattatt tatttaattt atttctctct tcctttcacg   3420
aaaattcctt tagccccata gatgtgcttg caaacccttc ctaaaatttt atttggaaag   3480
tagctcataa ttttgctaag aactgctgag ttttggagtg aggggaaagg aaaaaataga   3540
gaattacctc tgtgataatt tttataaaaa gcagcaataa ttcgaatggc tatgcaagtt   3600
aatgttttta gagtcttttc ttcagtctaa aatgagccag agttattctt taataatctg   3660
ctgtttatgc ctttggggag tatggtaccc atgagccaag cctccctgaa attgtacaga   3720
gggattttat aattgaatta aaatttagga atgcaatagc ttgtaaagag cctgctctcc   3780
aacatagggt ggtctcattc ttctggagac ttttttagat aaagtaaaat aattgtttaa   3840
atattttgtt taaaatatga ctgtttttcc tcccttttc ctagcagaaa taaagctgta   3900
agtctt                                                              3906
```

<210> SEQ ID NO 35
<211> LENGTH: 331
<212> TYPE: PRT
<213> ORGANISM: Homo sapiens

<400> SEQUENCE: 35

```
Met Ser Lys Thr Phe Val Lys Ser Lys Glu Met Gly Glu Leu Val Asn
 1               5                  10                  15

Thr Pro Ser Trp Met Asp Lys Gly Leu Gly Ser Gln Asn Glu Val Lys
            20                  25                  30

Glu Glu Glu Ser Arg Pro Gly Thr Tyr Gly Met Leu Ser Ser Leu Thr
        35                  40                  45

Glu Glu His Asp Ser Ile Glu Glu Glu Glu Glu Glu Glu Glu Asp Gly
    50                  55                  60

Glu Lys Pro Lys Arg Arg Gly Pro Lys Lys Lys Lys Met Thr Lys Ala
65                  70                  75                  80

Arg Leu Glu Arg Phe Arg Ala Arg Arg Val Lys Ala Asn Ala Arg Glu
                85                  90                  95

Arg Thr Arg Met His Gly Leu Asn Asp Ala Leu Asp Asn Leu Arg Arg
            100                 105                 110

Val Met Pro Cys Tyr Ser Lys Thr Gln Lys Leu Ser Lys Ile Glu Thr
        115                 120                 125

Leu Arg Leu Ala Arg Asn Tyr Ile Trp Ala Leu Ser Glu Val Leu Glu
    130                 135                 140

Thr Gly Gln Thr Pro Glu Gly Lys Gly Phe Val Glu Met Leu Cys Lys
145                 150                 155                 160

Gly Leu Ser Gln Pro Thr Ser Asn Leu Val Ala Gly Cys Leu Gln Leu
                165                 170                 175

Gly Pro Gln Ser Val Leu Leu Glu Lys His Glu Asp Lys Ser Pro Ile
            180                 185                 190

Cys Gly Ser Ala Ile Ser Val His Asn Phe Asn Tyr Gln Ser Pro Gly
        195                 200                 205

Leu Pro Ser Pro Pro Tyr Gly His Met Glu Thr His Leu Leu His Leu
    210                 215                 220

Lys Pro Gln Val Phe Lys Ser Leu Gly Glu Ser Ser Phe Gly Ser His
225                 230                 235                 240

Leu Pro Asp Cys Ser Thr Pro Pro Tyr Glu Gly Pro Leu Thr Pro Pro
                245                 250                 255

Leu Ser Ile Ser Gly Asn Phe Ser Leu Lys Gln Asp Gly Ser Pro Asp
            260                 265                 270

Leu Glu Lys Ser Tyr Ser Phe Met Pro His Tyr Pro Ser Ser Ser Leu
        275                 280                 285

Ser Ser Gly His Val His Ser Thr Pro Phe Gln Ala Gly Thr Pro Arg
    290                 295                 300

Tyr Asp Val Pro Ile Asp Met Ser Tyr Asp Ser Tyr Pro His His Gly
305                 310                 315                 320

Ile Gly Thr Gln Leu Asn Thr Val Phe Thr Glu
                325                 330
```

<210> SEQ ID NO 36
<211> LENGTH: 2465
<212> TYPE: DNA
<213> ORGANISM: Homo sapiens

<400> SEQUENCE: 36

```
cttctggcca gggaacgtgg aaggcgcacc gacagggatc cggccaggga gggcgagtga     60

aagaaggaaa tcagaaagga agggagttaa caaaataata aaaacagcct gagccacggc    120

tggagagacc gagacccggc gcaagagagc gcagccttag taggagagga acgcgagacg    180
```

```
cggcagagcg cgttcagcac tgacttttgc tgctgcttct gctttttttt ttcttagaaa    240
caagaaggcg ccagcggcag cctcacacgc gagcgccacg cgaggctccc gaagccaacc    300
cgcgaaggga ggaggggagg gaggaggagg cggcgtgcag ggaggagaaa aagcattttc    360
actttttttg ctcccactct aagaagtctc ccggggattt tgtatatatt ttttaacttc    420
cgtcagggct cccgcttcat atttcctttt ctttccctct ctgttcctgc acccaagttc    480
tctctgtgtc cccctcgcgg gccccgcacc tcgcgtcccg gatcgctctg attccgcgac    540
tccttggccg ccgctgcgca tggaaagctc tgccaagatg gagagcggcg gcgccggcca    600
gcagccccag ccgcagcccc agcagccctt cctgccgccc gcagcctgtt tctttgccac    660
ggccgcagcc gcggcggccg cagccgccgc agcggcagcg cagagcgcgc agcagcagca    720
gcagcagcag cagcagcagc agcaggcgcc gcagctgaga ccggcggccg acggccagcc    780
ctcaggggc ggtcacaagt cagcgcccaa gcaagtcaag cgacagcgct cgtcttcgcc    840
cgaactgatg cgctgcaaac gccggctcaa cttcagcggc tttggctaca gcctgccgca    900
gcagcagccg gccgccgtgg cgcgccgcaa cgagcgcgag cgcaaccgcg tcaagttggt    960
caacctgggc tttgccaccc ttcgggagca cgtccccaac ggcgcggcca acaagaagat   1020
gagtaaggtg gagacactgc gctcggcggt cgagtacatc cgcgcgctgc agcagctgct   1080
ggacgagcat gacgcggtga gcgccgcctt ccaggcaggc gtcctgtcgc ccaccatctc   1140
cccaactac tccaacgact tgaactccat ggccggctcg ccggtctcat cctactcgtc   1200
ggacgagggc tcttacgacc cgctcagccc cgaggagcag gagcttctcg acttcaccaa   1260
ctggttctga ggggctcggc ctggtcaggc cctggtgcga atggactttg gaagcagggt   1320
gatcgcacaa cctgcatctt tagtgctttc ttgtcagtgg cgttgggagg gggagaaaag   1380
gaaaagaaaa aaaaaagaag aagaagaaga aaagagaaga agaaaaaaac gaaaacagtc   1440
aaccaacccc atcgccaact aagcgaggca tgcctgagag acatggcttt cagaaaacgg   1500
gaagcgctca gaacagtatc tttgcactcc aatcattcac ggagatatga agagcaactg   1560
ggacctgagt caatgcgcaa aatgcagctt gtgtgcaaaa gcagtgggct cctggcagaa   1620
gggagcagca cacgcgttat agtaactccc atcacctcta acacgcacag ctgaaagttc   1680
ttgctcgggt cccttcacct cctcgccctt tcttaaagtg cagttcttag ccctctagaa   1740
acgagttggt gtctttcgtc tcagtagccc ccaccccaat aagctgtaga cattggttta   1800
cagtgaaact atgctattct cagccctttg aaactctgct tctcctccag ggcccgattc   1860
ccaaacccca tggcttccct cacactgtct tttctaccat tttcattata gaatgcttcc   1920
aatcttttgt gaatttttta ttataaaaaa tctatttgta tctatcctaa ccagttcggg   1980
gatatattaa gatattttg tacataagag agaaagagag agaaaaattt atagaagttt   2040
tgtacaaatg gtttaaaatg tgtatatctt gatactttaa catgtaatgc tattacctct   2100
gcatatttta gatgtgtagt tcaccttaca actgcaattt tccctatgtg gttttgtaaa   2160
gaactctcct cataggtgag atcaagaggc caccagttgt acttcagcac caatgtgtct   2220
tactttatag aaatgttgtt aatgtattaa tgatgttatt aaatactgtt caagaagaac   2280
aaagtttatg cagctactgt ccaaactcaa agtggcagcc agttggtttt gataggttgc   2340
cttttggaga tttctattac tgcctttttt tttcttactg ttttattaca aacttacaaa   2400
aatatgtata accctgtttt atacaaacta gtttcgtaat aaaacttttt cctttttta    2460
aaatg                                                                2465
```

<210> SEQ ID NO 37

<211> LENGTH: 236
<212> TYPE: PRT
<213> ORGANISM: Homo sapiens

<400> SEQUENCE: 37

```
Met Glu Ser Ser Ala Lys Met Glu Ser Gly Gly Ala Gly Gln Gln Pro
 1               5                  10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe
225                 230                 235
```

<210> SEQ ID NO 38
<211> LENGTH: 1635
<212> TYPE: DNA
<213> ORGANISM: Homo sapiens

<400> SEQUENCE: 38

```
cccgagaccc ggcgcaagag agcgcagcct tagtaggaga ggaacgcgag acgcggcaga      60

gcgcgttcag cactgacttt tgctgctgct tctgcttttt tttttcttag aaacaagaag     120

gcgccagcgg cagcctcaca cgcgagcgcc acgcgaggct cccgaagcca acccgcgaag     180

ggaggagggg agggaggagg aggcggcgtg cagggaggag aaaaagcatt ttcacctttt     240

ttgctcccac tctaagaagt ctcccgggga ttttgtatat attttttaac ttccgtcagg     300

gctcccgctt catatttcct tttctttccc tctctgttcc tgcacccaag ttctctctgt     360

gtcccccctcg cgggccccgc acctcgcgtc ccggatcgct ctgattccgc gactccttgg     420

ccgccgctgc gcatggaaag ctctgccaag atggagagcg gcggcgccgg ccagcagccc     480

cagccgcagc cccagcagcc cttcctgccg cccgcagcct gtttctttgc cacggccgca     540

gccgcggcgg ccgcagccgc cgcagcggca gcgcagagcg cgcagcagca gcagcagcag     600

cagcagcagc agcagcagca gcaggcgccg cagctgagac cggcggccga cggccagccc     660
```

```
tcagggggcg gtcacaagtc agcgcccaag caagtcaagc gacagcgctc gtcttcgccc    720

gaactgatgc gctgcaaacg ccggctcaac ttcagcggct ttggctacag cctgccgcag    780

cagcagccgg ccgccgtggc gcgccgcaac gagcgcgagc gcaaccgcgt caagttggtc    840

aacctgggct ttgccaccct tcgggagcac gtccccaacg gcgcggccaa caagaagatg    900

agtaaggtgg agacactgcg ctcggcggtc gagtacatcc gcgcgctgca gcagctgctg    960

gacgagcatg acgcggtgag cgccgccttc caggcaggcg tcctgtcgcc caccatctcc   1020

cccaactact ccaacgactt gaactccatg gccggctcgc cggtctcatc ctactcgtcg   1080

gacgagggct cttacgaccc gctcagcccc gaggagcagg agcttctcga cttcaccaac   1140

tggttctgag ggctcggcc tggtcaggcc ctggtgcgaa tggactttgg aagcagggtg    1200

atcgcacaac ctgcatcttt agtgctttct tgtcagtggc gttgggaggg ggagaaaagg   1260

aaaagaaaaa aaaagaagaa gaagaagaaa agagaagaag aaaaaaacga aaacagtcaa   1320

ccaaccccat cgccaactaa gcgaggcatg cctgagagac atggctttca gaaaacggga   1380

agcgctcaga acagtatctt tgcactccaa tcattcacgg agatatgaag agcaactggg   1440

acctgagtca atgcgcaaaa tgcagcttgt gtgcaaaagc agtgggctcc tggcagaagg   1500

gagcagcaca cgcgttatag taactcccat cacctctaac acgcacagct gaaagttctt   1560

gctcgggtcc cttcacctcc ccgccctttc ttagagtgca gttcttagcc ctctagaaac   1620

gagttggtgt ctttc                                                    1635


<210> SEQ ID NO 39
<211> LENGTH: 238
<212> TYPE: PRT
<213> ORGANISM: Homo sapiens

<400> SEQUENCE: 39

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Gln Gln
    50                  55                  60

Ala Pro Gln Leu Arg Pro Ala Ala Asp Gly Gln Pro Ser Gly Gly Gly
65                  70                  75                  80

His Lys Ser Ala Pro Lys Gln Val Lys Arg Gln Arg Ser Ser Ser Pro
                85                  90                  95

Glu Leu Met Arg Cys Lys Arg Arg Leu Asn Phe Ser Gly Phe Gly Tyr
            100                 105                 110

Ser Leu Pro Gln Gln Gln Pro Ala Ala Val Ala Arg Arg Asn Glu Arg
        115                 120                 125

Glu Arg Asn Arg Val Lys Leu Val Asn Leu Gly Phe Ala Thr Leu Arg
    130                 135                 140

Glu His Val Pro Asn Gly Ala Ala Asn Lys Lys Met Ser Lys Val Glu
145                 150                 155                 160

Thr Leu Arg Ser Ala Val Glu Tyr Ile Arg Ala Leu Gln Gln Leu Leu
                165                 170                 175

Asp Glu His Asp Ala Val Ser Ala Ala Phe Gln Ala Gly Val Leu Ser
            180                 185                 190

Pro Thr Ile Ser Pro Asn Tyr Ser Asn Asp Leu Asn Ser Met Ala Gly
```

```
        195                 200                 205

Ser Pro Val Ser Ser Tyr Ser Ser Asp Glu Gly Ser Tyr Asp Pro Leu
    210                 215                 220

Ser Pro Glu Glu Gln Glu Leu Leu Asp Phe Thr Asn Trp Phe
225                 230                 235


<210> SEQ ID NO 40
<211> LENGTH: 1830
<212> TYPE: DNA
<213> ORGANISM: Mus musculis

<400> SEQUENCE: 40

gcaaggtgtc ccgaggctcc agggttatga gatcgtcact attcagaacc ttttaacaac      60

aggaagtgga aacatgacca aatcatacag cgagagcggg ctgatgggcg agcctcagcc     120

ccaaggtccc ccaagctgga cagatgagtg tctcagttct caggacgagg aacacgaggc     180

agacaagaaa gaggacgagc ttgaagccat gaatgcagag gaggactctc tgagaaacgg     240

gggagaggag gaggaggaag atgaggatct agaggaagag gaggaagaag aagaggagga     300

ggaggatcaa aagcccaaga gacggggtcc caaaaagaaa aagatgacca aggcgcgcct     360

agaacgtttt aaattaaggc gcatgaaggc caacgcccgc gagcggaacc gcatgcacgg     420

gctgaacgcg gcgctggaca acctgcgcaa ggtggtacct tgctactcca agacccagaa     480

actgtctaaa atagagacac tgcgcttggc caagaactac atctgggctc tgtcagagat     540

cctgcgctca ggcaaaagcc ctgatctggt ctccttcgta cagacgctct gcaaaggttt     600

gtcccagccc actaccaatt tggtcgccgg ctgcctgcag ctcaaccctc ggactttctt     660

gcctgagcag aacccggaca tgcccccgca tctgccaacc gccagcgctt ccttcccggt     720

gcatccctac tcctaccagt cccctggact gcccagcccg ccctacggca ccatggacag     780

ctcccacgtc ttccacgtca agccgccgcc acacgcctac agcgcagctc tggagccctt     840

ctttgaaagc cccctaactg actgcaccag ccccttcctt gacggacccc tcagcccgcc     900

gctcagcatc aatggcaact tctctttcaa acacgaacca tccgccgagt ttgaaaaaaa     960

ttatgccttt accatgcact accctgcagc gacgctggca gggccccaaa gccacggatc    1020

aatcttctct tccggtgccg ctgcccctcg ctgcgagatc cccatagaca acattatgtc    1080

tttcgatagc cattcgcatc atgagcgagt catgagtgcc cagcttaatg ccatctttca    1140

cgattagagg cacgtcagtt tcactattcc cgggaaacga atccactgtg cgtacagtga    1200

ctgtcctgtt tacagaaggc agcccttttg ctaagattgc tgcaaagtgc aaatactcaa    1260

agcttcaagt gatatatgta tttattgtcg ttactgcctt tggaagaaac aggggatcaa    1320

agttcctgtt caccttatgt attgttttct atagctcttc tattttaaaa ataataatac    1380

agtaaagtaa aaaagaaaat gtgtaccacg aatttcgtgt agctgtattc agatcgtatt    1440

aattatctga tcgggataaa aaaaatcaca agcaataatt aggatctatg caatttttaa    1500

actagtaatg ggccaattaa aatatatata aatatatatt tttcaaccag cattttacta    1560

cctgtgacct ttcccatgct gaattatttt gttgtgattt tgtacagaat tttaatgac     1620

tttttataac gtggatttcc tattttaaaa ccatgcagct tcatcaattt ttatacatat    1680

cagaaaagta gaattatatc taatttatac aaaataattt aactaattta aaccagcaga    1740

aaagtgctta gaaagttatt gcgttgcctt agcacttctt tcttctctaa ttgtaaaaaa    1800

aaaaaaaaaa aaaaaaaaaa aaaaaaaaaa                                     1830


<210> SEQ ID NO 41
```

<211> LENGTH: 35
<212> TYPE: DNA
<213> ORGANISM: Artificial Sequence
<220> FEATURE:
<223> OTHER INFORMATION: oligonucleotide

<400> SEQUENCE: 41
ctttgtccgg aatccagctg tgccctgcgg gggag 35

<210> SEQ ID NO 42
<211> LENGTH: 35
<212> TYPE: DNA
<213> ORGANISM: Artificial Sequence
<220> FEATURE:
<223> OTHER INFORMATION: oligonucleotide

<400> SEQUENCE: 42
ctgcttcatc aggccatctg gccccttgtt aataa 35

<210> SEQ ID NO 43
<211> LENGTH: 35
<212> TYPE: DNA
<213> ORGANISM: Artificial Sequence
<220> FEATURE:
<223> OTHER INFORMATION: oligonucleotide

<400> SEQUENCE: 43
tgtataattg tgagcagatg gcgggggctg gcggc 35

<210> SEQ ID NO 44
<211> LENGTH: 35
<212> TYPE: DNA
<213> ORGANISM: Artificial Sequence
<220> FEATURE:
<223> OTHER INFORMATION: oligonucleotide

<400> SEQUENCE: 44
ttattaccgc tgaacatatg gccaatattt tgact 35

<210> SEQ ID NO 45
<211> LENGTH: 37
<212> TYPE: DNA
<213> ORGANISM: Artificial Sequence
<220> FEATURE:
<223> OTHER INFORMATION: oligonucleotide

<400> SEQUENCE: 45
gccctttgtc cggaatctgg ctgtgccctg cggggga 37

<210> SEQ ID NO 46
<211> LENGTH: 60
<212> TYPE: DNA
<213> ORGANISM: Artificial Sequence
<220> FEATURE:
<223> OTHER INFORMATION: oligonucleotide

<400> SEQUENCE: 46
gatcttccgg aatccagctg tgccctgcgg gggaggagcg ggctcgcgtg gcgcggcccg 60

<210> SEQ ID NO 47
<211> LENGTH: 60
<212> TYPE: DNA
<213> ORGANISM: Artificial Sequence
<220> FEATURE:
<223> OTHER INFORMATION: oligonucleotide

<400> SEQUENCE: 47

```
gatcttccgg aatctggctg tgccctgcgg gggaggagcg ggctcgcgtg gcgcggcccg     60


<210> SEQ ID NO 48
<211> LENGTH: 53
<212> TYPE: DNA
<213> ORGANISM: Artificial Sequence
<220> FEATURE:
<223> OTHER INFORMATION: oligonucleotide

<400> SEQUENCE: 48

gatctgtgag cagatggcgg ggtgagcaga tggcggggtg agcagatggc ggg            53


<210> SEQ ID NO 49
<211> LENGTH: 54
<212> TYPE: DNA
<213> ORGANISM: Artificial Sequence
<220> FEATURE:
<223> OTHER INFORMATION: oligonucleotide

<400> SEQUENCE: 49

gatctctgaa catatggcca actgaacata tggccaactg aacatatggc caag           54


<210> SEQ ID NO 50
<211> LENGTH: 54
<212> TYPE: DNA
<213> ORGANISM: Artificial Sequence
<220> FEATURE:
<223> OTHER INFORMATION: oligonucleotide

<400> SEQUENCE: 50

gatctgaatc cagctgtgcc cgaatccagc tgtgcccgaa tccagctgtg cccg           54


<210> SEQ ID NO 51
<211> LENGTH: 6
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: 3, 4
<223> OTHER INFORMATION: n = A,T,C or G

<400> SEQUENCE: 51

canntg                                                                 6


<210> SEQ ID NO 52
<211> LENGTH: 126
<212> TYPE: DNA
<213> ORGANISM: homosapien

<400> SEQUENCE: 52

cgggctcgcg tggcgcggcc ccagggcccc ggcgctgatt ggccggtggc gcgggcagca     60

gccgggcagg cacgctcctg gcccgggcga agcagataaa gcgtgccaag ggcacacga    120

cttgct                                                               126


<210> SEQ ID NO 53
<211> LENGTH: 214
<212> TYPE: PRT
<213> ORGANISM: Rattus norvegicus

<400> SEQUENCE: 53

Met Ala Pro His Pro Leu Asp Ala Pro Thr Ile Gln Val Ser Gln Glu
 1               5                   10                  15

Thr Gln Gln Pro Phe Pro Gly Ala Ser Asp His Glu Val Leu Ser Ser
```

```
            20                  25                  30

Asn Ser Thr Pro Pro Ser Pro Thr Leu Val Pro Arg Asp Cys Ser Glu
        35                  40                  45

Ala Glu Ala Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Ser Gly Asp Trp Gly Ser Ile Tyr Ser Pro Val
                165                 170                 175

Ser Gln Ala Gly Ser Leu Ser Pro Thr Ala Ser Leu Glu Glu Phe Pro
            180                 185                 190

Gly Leu Gln Val Pro Ser Ser Pro Ser Cys Leu Leu Pro Gly Thr Leu
        195                 200                 205

Val Phe Ser Asp Phe Leu
    210


<210> SEQ ID NO 54
<211> LENGTH: 57
<212> TYPE: PRT
<213> ORGANISM: homosapien

<400> SEQUENCE: 54

Arg Ser Arg Arg Lys Lys Ala Asn Asp Arg Glu Arg Asn Arg Met His
 1               5                  10                  15

Asn Leu Asn Ser Ala Leu Asp Ala Leu Arg Gly Val Leu Pro Thr Phe
            20                  25                  30

Pro Asp Asp Ala Lys Leu Thr Lys Ile Glu Thr Leu Arg Phe Ala His
        35                  40                  45

Asn Tyr Ile Trp Ala Leu Thr Gln Thr
    50                  55


<210> SEQ ID NO 55
<211> LENGTH: 57
<212> TYPE: PRT
<213> ORGANISM: Mus musculus

<400> SEQUENCE: 55

Arg Ser Arg Arg Val Lys Ala Asn Asp Arg Glu Arg Asn Arg Met His
 1               5                  10                  15

Asn Leu Asn Ala Ala Leu Asp Ala Leu Arg Ser Val Leu Pro Ser Phe
            20                  25                  30

Pro Asp Asp Thr Lys Leu Thr Lys Ile Glu Thr Leu Arg Phe Ala Tyr
        35                  40                  45

Asn Tyr Ile Trp Ala Leu Ala Glu Thr
    50                  55


<210> SEQ ID NO 56
```

-continued

```
<211> LENGTH: 57
<212> TYPE: PRT
<213> ORGANISM: Mus musculus

<400> SEQUENCE: 56

Lys Thr Arg Arg Leu Lys Ala Asn Asn Arg Glu Arg Asn Arg Met His
 1               5                  10                  15

Asn Leu Asn Ala Ala Leu Asp Ala Leu Arg Glu Val Leu Pro Thr Phe
            20                  25                  30

Pro Glu Asp Ala Lys Leu Thr Lys Ile Glu Thr Leu Arg Phe Ala His
        35                  40                  45

Asn Tyr Ile Trp Ala Leu Thr Glu Thr
    50                  55
```